United States Patent
Jimenez Lozano et al.

(10) Patent No.: US 12,102,557 B2
(45) Date of Patent: Oct. 1, 2024

(54) METHODS, DEVICES, AND SYSTEMS FOR IMPROVING SKIN CHARACTERISTICS

(71) Applicant: Zeltiq Aesthetics, Inc., North Chicago, IL (US)

(72) Inventors: Joel N. Jimenez Lozano, North Chicago, IL (US); Like Zeng, North Chicago, IL (US); Linda Pham, Kensington, CA (US); George Frangineas, Jr., Fremont, CA (US)

(73) Assignee: Zeltiq Aesthetics, Inc., North Chicago, IL (US)

( * ) Notice: Subject to any disclaimer, the term of this patent is extended or adjusted under 35 U.S.C. 154(b) by 73 days.

(21) Appl. No.: 17/873,064

(22) Filed: Jul. 25, 2022

(65) Prior Publication Data

US 2023/0051638 A1    Feb. 16, 2023

Related U.S. Application Data

(63) Continuation of application No. 16/528,249, filed on Jul. 31, 2019, now Pat. No. 11,446,175.

(60) Provisional application No. 62/712,562, filed on Jul. 31, 2018.

(51) Int. Cl.
*A61F 7/00* (2006.01)
(52) U.S. Cl.
CPC ........ *A61F 7/00* (2013.01); *A61F 2007/0052* (2013.01); *A61F 2007/0056* (2013.01)
(58) Field of Classification Search
CPC ............. A61B 90/98; A61F 2007/0052; A61F 2007/0056; A61F 2007/0075; A61F 7/00; A61F 7/007; A61F 7/10
See application file for complete search history.

(56) References Cited

U.S. PATENT DOCUMENTS

| | | | |
|---|---|---|---|
| 681,806 | A | 9/1901 | Mignault |
| 889,810 | A | 6/1908 | Robinson |
| 1,093,868 | A | 4/1914 | Leighty |
| 2,516,491 | A | 7/1950 | Swastek |
| 2,521,780 | A | 9/1950 | Dodd |

(Continued)

FOREIGN PATENT DOCUMENTS

| | | |
|---|---|---|
| AU | 2011253768 A1 | 6/2012 |
| CA | 2441489 A1 | 3/2005 |

(Continued)

OTHER PUBLICATIONS

"ThermaCool Monopolar Capacitive Radiofrequency, The one choice for nonablative tissue tightening and contouring", Thermage, Inc. Tech Brochure, Nov. 30, 2005, 8 pgs.

(Continued)

*Primary Examiner* — Tigist S Demie
(74) *Attorney, Agent, or Firm* — Mintz, Levin, Cohn, Ferris, Glovsky and Popeo, P.C.

(57) ABSTRACT

Provided herein are systems, compositions, and methods for improving one or more skin characteristics in a subject. These systems, compositions, and methods are configured to cool the subject's skin at a target site to a degree that alters adipocyte signaling but does not produce significant destruction of subcutaneous lipid-rich cells. In some embodiments, alteration of adipocyte signaling produces an improvement in one or more skin characteristics.

15 Claims, 23 Drawing Sheets

(56) References Cited

U.S. PATENT DOCUMENTS

| | | |
|---|---|---|
| 2,726,658 A | 12/1955 | Chessey |
| 2,766,619 A | 10/1956 | Tribus et al. |
| 2,851,602 A | 9/1958 | Cramwinckel et al. |
| 3,093,135 A | 6/1963 | Hirschhorn |
| 3,132,688 A | 5/1964 | Nowak |
| 3,133,539 A | 5/1964 | Eidus |
| 3,282,267 A | 11/1966 | Eidus |
| 3,341,230 A | 9/1967 | Wichers |
| 3,502,080 A | 3/1970 | Hirschhorn |
| 3,566,871 A | 3/1971 | Richter et al. |
| 3,587,577 A | 6/1971 | Smirnov et al. |
| 3,591,645 A | 7/1971 | Selwitz |
| 3,692,338 A | 9/1972 | Nick |
| 3,702,114 A | 11/1972 | Zacarian |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Stumpf et al. |
| 3,942,519 A | 3/1976 | Shock |
| 3,948,269 A | 4/1976 | Zimmer |
| 3,986,385 A | 10/1976 | Johnston et al. |
| 3,993,053 A | 11/1976 | Grossan |
| 4,002,221 A | 1/1977 | Buchalter |
| 4,008,910 A | 2/1977 | Roche |
| 4,026,299 A | 5/1977 | Sauder |
| 4,140,130 A | 2/1979 | Storm, III |
| 4,149,529 A | 4/1979 | Copeland et al. |
| 4,178,429 A | 12/1979 | Scheffer |
| 4,202,336 A | 5/1980 | van Gerven |
| 4,266,043 A | 5/1981 | Fujii et al. |
| 4,269,068 A | 5/1981 | Molina |
| D260,173 S | 8/1981 | Wiebe |
| 4,381,009 A | 4/1983 | Del Bon |
| 4,396,011 A | 8/1983 | Mack et al. |
| 4,459,854 A | 7/1984 | Richardson et al. |
| 4,470,263 A | 9/1984 | Lehovec et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt |
| 4,741,338 A | 5/1988 | Miyamae |
| 4,758,217 A | 7/1988 | Gueret |
| 4,764,463 A | 8/1988 | Mason et al. |
| 4,802,475 A | 2/1989 | Weshahy |
| 4,832,022 A | 5/1989 | Tjulkov et al. |
| 4,841,969 A | 6/1989 | Donnerhack et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,905,697 A | 3/1990 | Heggs et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A | 10/1990 | Golden |
| 4,990,144 A | 2/1991 | Blott |
| 5,007,433 A | 4/1991 | Hermsdorffer et al. |
| 5,018,521 A | 5/1991 | Campbell |
| 5,024,650 A | 6/1991 | Hagiwara et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen |
| 5,139,496 A | 8/1992 | Hed |
| 5,143,063 A | 9/1992 | Fellner |
| 5,148,804 A | 9/1992 | Hill et al. |
| 5,158,070 A | 10/1992 | Dory |
| 5,160,312 A | 11/1992 | Voelkel |
| 5,169,384 A | 12/1992 | Bosniak et al. |
| 5,197,466 A | 3/1993 | Marchosky et al. |
| 5,207,674 A | 5/1993 | Hamilton |
| 5,209,227 A | 5/1993 | Deutsch |
| 5,221,726 A | 6/1993 | Dabi et al. |
| 5,264,234 A | 11/1993 | Windhab et al. |
| 5,277,030 A | 1/1994 | Miller |
| 5,288,469 A | 2/1994 | Skalla |
| 5,314,423 A | 5/1994 | Seney |
| 5,327,886 A | 7/1994 | Chiu |
| 5,330,745 A | 7/1994 | McDow |
| 5,333,460 A | 8/1994 | Lewis et al. |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold |
| 5,351,677 A | 10/1994 | Kami et al. |
| 5,358,467 A | 10/1994 | Milstein et al. |
| 5,362,966 A | 11/1994 | Rosenthal et al. |
| 5,363,347 A | 11/1994 | Nguyen |
| 5,372,608 A | 12/1994 | Johnson |
| 5,386,837 A | 2/1995 | Sterzer |
| 5,411,541 A | 5/1995 | Bell et al. |
| 5,427,772 A | 6/1995 | Hagan |
| 5,433,717 A | 7/1995 | Rubinsky et al. |
| D362,091 S | 9/1995 | Tomasiak et al. |
| 5,456,703 A | 10/1995 | Beeuwkes, III |
| 5,472,416 A | 12/1995 | Blugerman et al. |
| 5,486,207 A | 1/1996 | Mahawili |
| 5,497,596 A | 3/1996 | Zatkulak |
| 5,501,655 A | 3/1996 | Rolt et al. |
| 5,505,726 A | 4/1996 | Meserol |
| 5,505,730 A | 4/1996 | Edwards |
| 5,507,790 A | 4/1996 | Weiss |
| 5,513,629 A | 5/1996 | Johnson |
| 5,514,105 A | 5/1996 | Goodman, Jr. et al. |
| 5,514,170 A | 5/1996 | Mauch |
| 5,516,505 A | 5/1996 | McDow |
| 5,531,742 A | 7/1996 | Barken |
| 5,558,376 A | 9/1996 | Woehl |
| 5,562,604 A | 10/1996 | Yablon et al. |
| 5,571,801 A | 11/1996 | Segall et al. |
| 5,575,812 A | 11/1996 | Owens |
| 5,603,221 A | 2/1997 | Maytal |
| 5,628,769 A | 5/1997 | Saringer |
| 5,634,890 A | 6/1997 | Morris |
| 5,634,940 A | 6/1997 | Panyard |
| 5,647,051 A | 7/1997 | Neer |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay |
| 5,660,836 A | 8/1997 | Knowlton |
| 5,665,053 A | 9/1997 | Jacobs |
| 5,672,172 A | 9/1997 | Zupkas |
| 5,700,284 A | 12/1997 | Owens |
| 5,725,483 A | 3/1998 | Podolsky |
| 5,733,280 A | 3/1998 | Avitall |
| 5,741,248 A | 4/1998 | Stern et al. |
| 5,746,702 A | 5/1998 | Gelfgat et al. |
| 5,746,736 A | 5/1998 | Tankovich |
| 5,755,663 A | 5/1998 | Larsen et al. |
| 5,755,753 A | 5/1998 | Knowlton |
| 5,755,755 A | 5/1998 | Panyard |
| 5,759,182 A | 6/1998 | Varney et al. |
| 5,759,764 A | 6/1998 | Polovina |
| 5,764,794 A | 6/1998 | Perlin |
| 5,769,879 A | 6/1998 | Richards et al. |
| 5,785,955 A | 7/1998 | Fischer |
| 5,792,080 A | 8/1998 | Ookawa et al. |
| 5,800,490 A | 9/1998 | Patz et al. |
| 5,802,865 A | 9/1998 | Strauss |
| 5,814,040 A | 9/1998 | Nelson et al. |
| D399,493 S | 10/1998 | Nakajima et al. |
| 5,817,050 A | 10/1998 | Klein |

(56) References Cited

U.S. PATENT DOCUMENTS

| | | |
|---|---|---|
| 5,817,145 A | 10/1998 | Augustine et al. |
| 5,817,149 A | 10/1998 | Owens |
| 5,817,150 A | 10/1998 | Owens |
| 5,830,208 A | 11/1998 | Muller |
| 5,833,685 A | 11/1998 | Tortal et al. |
| 5,844,013 A | 12/1998 | Kenndoff et al. |
| 5,853,364 A | 12/1998 | Baker, Jr. et al. |
| 5,865,841 A | 2/1999 | Kolen et al. |
| 5,871,524 A | 2/1999 | Knowlton |
| 5,871,526 A | 2/1999 | Gibbs et al. |
| 5,885,211 A | 3/1999 | Eppstein et al. |
| 5,891,617 A | 4/1999 | Watson et al. |
| 5,895,418 A | 4/1999 | Saringer |
| 5,901,707 A | 5/1999 | Gonçalves |
| 5,902,256 A | 5/1999 | Benaron |
| 5,919,219 A | 7/1999 | Knowlton |
| 5,944,748 A | 8/1999 | Mager et al. |
| 5,948,011 A | 9/1999 | Knowlton |
| 5,952,168 A | 9/1999 | Wowk et al. |
| 5,954,680 A | 9/1999 | Augustine |
| 5,962,477 A | 10/1999 | Mak |
| 5,964,092 A | 10/1999 | Tozuka et al. |
| 5,964,749 A | 10/1999 | Eckhouse et al. |
| 5,967,976 A | 10/1999 | Larsen et al. |
| 5,980,561 A | 11/1999 | Kolen et al. |
| 5,986,167 A | 11/1999 | Arteman et al. |
| 5,989,286 A | 11/1999 | Owens |
| 5,992,158 A | 11/1999 | Goddard et al. |
| 5,997,530 A | 12/1999 | Nelson et al. |
| 6,017,337 A | 1/2000 | Pira |
| 6,023,932 A | 2/2000 | Johnston |
| 6,031,525 A | 2/2000 | Perlin |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | McClure et al. |
| 6,049,927 A | 4/2000 | Thomas et al. |
| 6,051,159 A | 4/2000 | Hao |
| D424,699 S | 5/2000 | Allen |
| 6,071,239 A | 6/2000 | Cribbs et al. |
| 6,074,415 A | 6/2000 | Der Ovanesian |
| 6,093,230 A | 7/2000 | Johnson, III et al. |
| 6,102,885 A | 8/2000 | Bass |
| 6,104,952 A | 8/2000 | Tu et al. |
| 6,104,959 A | 8/2000 | Spertell |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,139,545 A | 10/2000 | Utley et al. |
| 6,150,148 A | 11/2000 | Nanda et al. |
| 6,151,735 A | 11/2000 | Koby et al. |
| 6,152,952 A | 11/2000 | Owens |
| 6,171,301 B1 | 1/2001 | Nelson et al. |
| 6,176,869 B1 | 1/2001 | Mason et al. |
| 6,180,867 B1 | 1/2001 | Hedengren et al. |
| 6,224,617 B1 | 5/2001 | Saadat et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung |
| 6,312,453 B1 | 11/2001 | Stefanile et al. |
| 6,319,510 B1 | 11/2001 | Yates |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,395,467 B1 | 5/2002 | Fahy et al. |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak, III et al. |
| 6,494,844 B1 | 12/2002 | Van Bladel et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| D471,982 S | 3/2003 | Cheng |
| 6,527,765 B2 | 3/2003 | Kelman et al. |
| 6,527,798 B2 | 3/2003 | Ginsburg et al. |
| 6,544,248 B2 | 4/2003 | Bass |
| 6,547,811 B1 | 4/2003 | Becker et al. |
| 6,548,297 B1 | 4/2003 | Kuri-Harcuch et al. |
| 6,551,255 B2 | 4/2003 | Van Bladel et al. |
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,607,498 B2 | 8/2003 | Eshel |
| 6,620,187 B2 | 9/2003 | Carson et al. |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,524 B1 | 1/2004 | Elbrecht et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chomenky et al. |
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |
| 6,743,222 B2 | 6/2004 | Durkin et al. |
| 6,746,474 B2 | 6/2004 | Saadat |
| 6,749,624 B2 | 6/2004 | Knowlton |
| 6,753,182 B1 | 6/2004 | Kadkade et al. |
| 6,764,493 B1 | 7/2004 | Weber et al. |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | McHale et al. |
| 6,840,955 B2 | 1/2005 | Ein |
| 6,849,075 B2 | 2/2005 | Bertolero et al. |

(56) References Cited

U.S. PATENT DOCUMENTS

| | | |
|---|---|---|
| 6,878,144 B2 | 4/2005 | Altshuler et al. |
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries, Jr. et al. |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee |
| 7,054,685 B2 | 5/2006 | Dimmer et al. |
| 7,060,061 B2 | 6/2006 | Altshuler et al. |
| D525,592 S | 7/2006 | Nguyen |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| D546,949 S | 7/2007 | Green |
| 7,258,674 B2 | 8/2007 | Cribbs et al. |
| D550,362 S | 9/2007 | Olivera et al. |
| 7,267,675 B2 | 9/2007 | Stern et al. |
| 7,276,058 B2 | 10/2007 | Altshuler et al. |
| 7,318,821 B2 | 1/2008 | Lalonde et al. |
| 7,331,951 B2 | 2/2008 | Eshel et al. |
| 7,347,855 B2 | 3/2008 | Eshel et al. |
| D568,258 S | 5/2008 | Adam |
| 7,367,341 B2 | 5/2008 | Anderson et al. |
| 7,532,201 B2 | 5/2009 | Quistgaard et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,959,657 B1 | 6/2011 | Harsy |
| 7,963,959 B2 | 6/2011 | Da Silva et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,247,221 B2 | 8/2012 | Fawcett |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,372,130 B2 | 2/2013 | Young |
| 8,387,631 B1 | 3/2013 | Thonghara et al. |
| 8,397,518 B1 | 3/2013 | Vistakula |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | Slayton et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,676,338 B2 | 3/2014 | Levinson |
| D702,848 S | 4/2014 | Mendoza et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 8,764,693 B1 | 7/2014 | Graham |
| 8,834,547 B2 | 9/2014 | Anderson et al. |
| 9,132,031 B2 | 9/2015 | Levinson et al. |
| 9,149,322 B2 | 10/2015 | Knowlton |
| 9,314,368 B2 | 4/2016 | Allison et al. |
| 9,375,345 B2 | 6/2016 | Levinson et al. |
| 9,408,745 B2 | 8/2016 | Levinson et al. |
| D777,338 S | 1/2017 | Coakley et al. |
| 9,545,523 B2 | 1/2017 | Nanda |
| 9,581,942 B1 | 2/2017 | Shippert |
| 9,655,770 B2 | 5/2017 | Levinson et al. |
| 9,737,434 B2 | 8/2017 | Allison |
| 9,752,856 B2 | 9/2017 | Rashad |
| 9,844,460 B2 | 12/2017 | Weber et al. |
| 9,844,461 B2 | 12/2017 | Levinson et al. |
| 9,855,166 B2 | 1/2018 | Anderson et al. |
| 9,861,421 B2 | 1/2018 | O'Neil et al. |
| 9,861,520 B2 | 1/2018 | Baker et al. |
| 10,092,346 B2 | 10/2018 | Levinson |
| 10,201,380 B2 | 2/2019 | DeBenedictis et al. |
| 10,292,859 B2 | 5/2019 | Levinson et al. |
| 10,383,787 B2 | 8/2019 | Rosen et al. |
| 10,471,269 B1 | 11/2019 | Schwarz et al. |
| 10,524,956 B2 | 1/2020 | DeBenedictis et al. |
| 10,555,831 B2 | 2/2020 | Jimenez Lozano et al. |
| 10,568,759 B2 | 2/2020 | Yee et al. |
| 10,575,890 B2 | 3/2020 | DeBenedictis et al. |
| 10,675,176 B1 | 6/2020 | Coakley et al. |
| 10,765,552 B2 | 9/2020 | Root et al. |
| 10,806,500 B2 | 10/2020 | DeBenedictis et al. |
| 10,912,599 B2 | 2/2021 | O'Neil et al. |
| 10,952,891 B1 | 3/2021 | Yee et al. |
| D921,211 S | 6/2021 | Jeong et al. |
| D921,911 S | 6/2021 | Jeong et al. |
| 11,179,269 B2 | 11/2021 | Levinson et al. |
| 11,219,549 B2 | 1/2022 | Levinson et al. |
| 11,452,634 B2 | 9/2022 | Baker et al. |
| 2001/0005791 A1 | 6/2001 | Ginsburg et al. |
| 2001/0007952 A1 | 7/2001 | Shimizu |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0045104 A1 | 11/2001 | Bailey et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0042607 A1 | 4/2002 | Palmer et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0068874 A1 | 6/2002 | Zuckerwar et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |

(56) References Cited

U.S. PATENT DOCUMENTS

| | | |
|---|---|---|
| 2002/0151887 A1 | 10/2002 | Stern et al. |
| 2002/0156509 A1 | 10/2002 | Cheung |
| 2002/0161357 A1 | 10/2002 | Anderson et al. |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0062040 A1 | 4/2003 | Lurie et al. |
| 2003/0069618 A1 | 4/2003 | Smith et al. |
| 2003/0077326 A1 | 4/2003 | Newton et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0109912 A1 | 6/2003 | Joye et al. |
| 2003/0114885 A1 | 6/2003 | Nova et al. |
| 2003/0120268 A1 | 6/2003 | Bertolero et al. |
| 2003/0125649 A1 | 7/2003 | McIntosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220594 A1 | 11/2003 | Halvorson et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Ella et al. |
| 2004/0082886 A1 | 4/2004 | Timpson |
| 2004/0093042 A1 | 5/2004 | Altshuler et al. |
| 2004/0102768 A1 | 5/2004 | Cluzeau et al. |
| 2004/0104012 A1 | 6/2004 | Zhou et al. |
| 2004/0106867 A1 | 6/2004 | Eshel et al. |
| 2004/0116866 A1 | 6/2004 | Gorman et al. |
| 2004/0133251 A1 | 7/2004 | Altshuler et al. |
| 2004/0159109 A1 | 8/2004 | Harvie |
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2004/0267339 A1 | 12/2004 | Yon et al. |
| 2005/0010197 A1 | 1/2005 | Lau et al. |
| 2005/0033957 A1 | 2/2005 | Enokida |
| 2005/0038422 A1 | 2/2005 | Maurice |
| 2005/0049526 A1 | 3/2005 | Baer |
| 2005/0049543 A1 | 3/2005 | Anderson et al. |
| 2005/0049661 A1 | 3/2005 | Koffroth |
| 2005/0065531 A1 | 3/2005 | Cohen |
| 2005/0113725 A1 | 5/2005 | Masuda |
| 2005/0143781 A1 | 6/2005 | Carbunaru et al. |
| 2005/0145372 A1 | 7/2005 | Noel |
| 2005/0149153 A1 | 7/2005 | Nakase |
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0177075 A1 | 8/2005 | Meunier |
| 2005/0182462 A1 | 8/2005 | Chornenky et al. |
| 2005/0187495 A1 | 8/2005 | Quistgaard et al. |
| 2005/0187502 A1 | 8/2005 | Krempel et al. |
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1 | 11/2005 | Anderson et al. |
| 2005/0261753 A1 | 11/2005 | Littrup et al. |
| 2005/0277859 A1 | 12/2005 | Carlsmith |
| 2005/0281789 A1 | 12/2005 | Rao et al. |
| 2005/0283144 A1 | 12/2005 | Shiono et al. |
| 2006/0030778 A1 | 2/2006 | Mendlein et al. |
| 2006/0035380 A1 | 2/2006 | Saint-Leger |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0111613 A1 | 5/2006 | Boutillette et al. |
| 2006/0122509 A1 | 6/2006 | Desilets |
| 2006/0188832 A1 | 8/2006 | McCarren |
| 2006/0189964 A1 | 8/2006 | Anderson et al. |
| 2006/0195168 A1 | 8/2006 | Dunbar et al. |
| 2006/0200063 A1 | 9/2006 | Munro et al. |
| 2006/0206040 A1 | 9/2006 | Greenberg |
| 2006/0206110 A1 | 9/2006 | Knowlton et al. |
| 2006/0234899 A1 | 10/2006 | Nekmard et al. |
| 2006/0259102 A1 | 11/2006 | Slatkine |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | DeLonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0073367 A1 | 3/2007 | Jones et al. |
| 2007/0078502 A1 | 4/2007 | Weber et al. |
| 2007/0088413 A1 | 4/2007 | Weber et al. |
| 2007/0100398 A1 | 5/2007 | Sloan |
| 2007/0106342 A1 | 5/2007 | Schumann |
| 2007/0123962 A1 | 5/2007 | Grahn et al. |
| 2007/0129441 A1 | 6/2007 | Koulen |
| 2007/0129714 A1 | 6/2007 | Elkins et al. |
| 2007/0135876 A1 | 6/2007 | Weber |
| 2007/0141265 A1 | 6/2007 | Thomson |
| 2007/0179482 A1 | 8/2007 | Anderson |
| 2007/0193278 A1 | 8/2007 | Polacek et al. |
| 2007/0198071 A1 | 8/2007 | Ting et al. |
| 2007/0219540 A1 | 9/2007 | Masotti et al. |
| 2007/0233226 A1 | 10/2007 | Kochamba et al. |
| 2007/0239062 A1 | 10/2007 | Chopra et al. |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1 | 11/2007 | Levinson et al. |
| 2007/0265585 A1 | 11/2007 | Joshi et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0097207 A1 | 4/2008 | Cai |

(56) References Cited

U.S. PATENT DOCUMENTS

| | | |
|---|---|---|
| 2008/0114348 A1 | 5/2008 | Vancelette et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0154254 A1 | 6/2008 | Burger et al. |
| 2008/0160480 A1 | 7/2008 | Ruddle et al. |
| 2008/0161892 A1 | 7/2008 | Mercuro et al. |
| 2008/0183164 A1 | 7/2008 | Elkins et al. |
| 2008/0188915 A1 | 8/2008 | Mills et al. |
| 2008/0195036 A1 | 8/2008 | Merchant et al. |
| 2008/0208181 A1 | 8/2008 | Toubia et al. |
| 2008/0248554 A1 | 10/2008 | Merchant et al. |
| 2008/0269851 A1 | 10/2008 | Deem et al. |
| 2008/0287839 A1 | 11/2008 | Rosen et al. |
| 2008/0300529 A1 | 12/2008 | Reinstein |
| 2008/0312651 A1 | 12/2008 | Pope et al. |
| 2009/0012434 A1 | 1/2009 | Anderson |
| 2009/0016980 A1 | 1/2009 | Tsivkin et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0054882 A1 | 2/2009 | Hansen et al. |
| 2009/0076488 A1 | 3/2009 | Welches et al. |
| 2009/0112134 A1 | 4/2009 | Avni |
| 2009/0118684 A1 | 5/2009 | Da Silva et al. |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0171253 A1 | 7/2009 | Davenport |
| 2009/0171334 A1 | 7/2009 | Elkins et al. |
| 2009/0209886 A1 | 8/2009 | Tudico |
| 2009/0221938 A1 | 9/2009 | Rosenberg et al. |
| 2009/0226424 A1 | 9/2009 | Hsu |
| 2009/0276018 A1 | 11/2009 | Brader |
| 2009/0281464 A1 | 11/2009 | Cioanta et al. |
| 2009/0299234 A1 | 12/2009 | Cho |
| 2009/0306749 A1 | 12/2009 | Mulindwa |
| 2009/0312676 A1 | 12/2009 | Rousso et al. |
| 2009/0312693 A1 | 12/2009 | Thapliyal et al. |
| 2009/0318851 A1 | 12/2009 | Schenck |
| 2009/0326621 A1 | 12/2009 | El-Galley |
| 2010/0015190 A1 | 1/2010 | Hassler |
| 2010/0028432 A1 | 2/2010 | Gasco |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0042087 A1 | 2/2010 | Goldboss et al. |
| 2010/0047360 A1 | 2/2010 | Klaveness et al. |
| 2010/0049178 A1 | 2/2010 | Deem et al. |
| 2010/0081971 A1 | 4/2010 | Allison |
| 2010/0087806 A1 | 4/2010 | Da Silva et al. |
| 2010/0106230 A1 | 4/2010 | Buchanan et al. |
| 2010/0152824 A1 | 6/2010 | Allison |
| 2010/0168726 A1 | 7/2010 | Brookman |
| 2010/0179531 A1 | 7/2010 | Nebrigic et al. |
| 2010/0198064 A1 | 8/2010 | Perl et al. |
| 2010/0198204 A1 | 8/2010 | Rogers |
| 2010/0217349 A1 | 8/2010 | Fahey |
| 2010/0217357 A1 | 8/2010 | Da Silva et al. |
| 2010/0241023 A1 | 9/2010 | Gilbert |
| 2010/0268220 A1 | 10/2010 | Johnson et al. |
| 2010/0280582 A1 | 11/2010 | Baker et al. |
| 2011/0009860 A1 | 1/2011 | Chornenky et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0060242 A1 | 3/2011 | Hausman et al. |
| 2011/0060323 A1 | 3/2011 | Baust et al. |
| 2011/0066083 A1 | 3/2011 | Tosaya et al. |
| 2011/0066216 A1 | 3/2011 | Ting et al. |
| 2011/0077557 A1 | 3/2011 | Wing et al. |
| 2011/0077723 A1 | 3/2011 | Parish et al. |
| 2011/0112405 A1 | 5/2011 | Barthe et al. |
| 2011/0112520 A1 | 5/2011 | Michael |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Mnozil et al. |
| 2011/0202048 A1 | 8/2011 | Nebrigic |
| 2011/0238050 A1 | 9/2011 | Allison et al. |
| 2011/0238051 A1 | 9/2011 | Levinson et al. |
| 2011/0257642 A1 | 10/2011 | Griggs, III |
| 2011/0288537 A1 | 11/2011 | Halaka |
| 2011/0300079 A1 | 12/2011 | Martens et al. |
| 2011/0301585 A1 | 12/2011 | Goulko |
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1 | 1/2012 | Levinson |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0041525 A1 | 2/2012 | Karni |
| 2012/0046547 A1 | 2/2012 | Barthe et al. |
| 2012/0053458 A1 | 3/2012 | Barthe et al. |
| 2012/0065629 A1 | 3/2012 | Elkins et al. |
| 2012/0083862 A1 | 4/2012 | Altshuler et al. |
| 2012/0089211 A1 | 4/2012 | Curtis et al. |
| 2012/0101549 A1 | 4/2012 | Schumann |
| 2012/0109041 A1 | 5/2012 | Munz |
| 2012/0158100 A1 | 6/2012 | Schomacker |
| 2012/0209363 A1 | 8/2012 | Williams, III et al. |
| 2012/0233736 A1 | 9/2012 | Tepper et al. |
| 2012/0238901 A1 | 9/2012 | Augustine |
| 2012/0239123 A1 | 9/2012 | Weber et al. |
| 2012/0253416 A1 | 10/2012 | Erez et al. |
| 2012/0259322 A1 | 10/2012 | Fourkas et al. |
| 2012/0277674 A1 | 11/2012 | Clark, IIIii et al. |
| 2012/0303104 A1 | 11/2012 | Levy |
| 2012/0310232 A1 | 12/2012 | Erez |
| 2013/0018236 A1 | 1/2013 | Altshuler et al. |
| 2013/0019374 A1 | 1/2013 | Schwartz |
| 2013/0035680 A1 | 2/2013 | Ben-Haim et al. |
| 2013/0066309 A1 | 3/2013 | Levinson |
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0150844 A1 | 6/2013 | Deem et al. |
| 2013/0158440 A1 | 6/2013 | Allison |
| 2013/0158636 A1 | 6/2013 | Ting et al. |
| 2013/0166003 A1 | 6/2013 | Johnson et al. |
| 2013/0185440 A1 | 7/2013 | Blau et al. |
| 2013/0190744 A1 | 7/2013 | Avram et al. |
| 2013/0238062 A1 | 9/2013 | Ron Edoute et al. |
| 2013/0245507 A1 | 9/2013 | Khorassani Zadeh |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0303904 A1 | 11/2013 | Barthe et al. |
| 2013/0303905 A1 | 11/2013 | Barthe et al. |
| 2013/0315924 A1 | 11/2013 | Hsu et al. |
| 2013/0315999 A1 | 11/2013 | Paithankar et al. |
| 2013/0331914 A1 | 12/2013 | Lee et al. |
| 2013/0345701 A1 | 12/2013 | Allen, IV et al. |
| 2014/0005759 A1 | 1/2014 | Fahey et al. |
| 2014/0005760 A1 | 1/2014 | Levinson et al. |
| 2014/0067025 A1 | 3/2014 | Levinson et al. |
| 2014/0142469 A1 | 5/2014 | Britva et al. |
| 2014/0163582 A1 | 6/2014 | Austen et al. |
| 2014/0200487 A1 | 7/2014 | Ramdas et al. |
| 2014/0200488 A1 | 7/2014 | Seo et al. |
| 2014/0222121 A1 | 8/2014 | Spence et al. |
| 2014/0228718 A1 | 8/2014 | Diller et al. |
| 2014/0277219 A1 | 9/2014 | Nanda |
| 2014/0277302 A1 | 9/2014 | Weber et al. |

(56) References Cited

U.S. PATENT DOCUMENTS

| | | |
|---|---|---|
| 2014/0277303 A1 | 9/2014 | Biser et al. |
| 2014/0303697 A1 | 10/2014 | Anderson et al. |
| 2014/0316393 A1 | 10/2014 | Levinson |
| 2015/0005760 A1 | 1/2015 | Poulsen |
| 2015/0112412 A1 | 4/2015 | Anderson et al. |
| 2015/0141797 A1 | 5/2015 | Turnquist et al. |
| 2015/0209174 A1 | 7/2015 | Abreu |
| 2015/0216719 A1* | 8/2015 | DeBenedictis ...... A61K 31/045 607/108 |
| 2015/0216720 A1 | 8/2015 | DeBenedictis et al. |
| 2015/0216816 A1 | 8/2015 | O'Neil et al. |
| 2015/0223975 A1 | 8/2015 | Anderson et al. |
| 2015/0283022 A1 | 10/2015 | Lee et al. |
| 2015/0328077 A1 | 11/2015 | Levinson |
| 2015/0328478 A1 | 11/2015 | Mcdaniel |
| 2015/0335468 A1 | 11/2015 | Rose et al. |
| 2015/0342780 A1 | 12/2015 | Levinson et al. |
| 2016/0045755 A1 | 2/2016 | Chun et al. |
| 2016/0051308 A1 | 2/2016 | Pennybacker et al. |
| 2016/0051401 A1 | 2/2016 | Yee et al. |
| 2016/0089550 A1 | 3/2016 | DeBenedictis et al. |
| 2016/0114088 A1 | 4/2016 | Minskoff et al. |
| 2016/0135985 A1 | 5/2016 | Anderson et al. |
| 2016/0143771 A1* | 5/2016 | Swyer ................. A61F 7/0085 607/104 |
| 2016/0220849 A1 | 8/2016 | Knowlton |
| 2016/0296269 A1 | 10/2016 | Rubinsky et al. |
| 2016/0317346 A1 | 11/2016 | Kovach |
| 2016/0324684 A1 | 11/2016 | Levinson et al. |
| 2017/0007309 A1 | 1/2017 | DeBenedictis et al. |
| 2017/0035492 A1 | 2/2017 | Longoria |
| 2017/0065323 A1 | 3/2017 | Rosen et al. |
| 2017/0079641 A1 | 3/2017 | Overmyer et al. |
| 2017/0079833 A1 | 3/2017 | Frangineas, Jr. et al. |
| 2017/0105869 A1 | 4/2017 | Frangineas, Jr. |
| 2017/0165105 A1* | 6/2017 | Anderson ................. A61F 7/02 |
| 2017/0196731 A1 | 7/2017 | DeBenedictis et al. |
| 2017/0224528 A1 | 8/2017 | Berg et al. |
| 2017/0239079 A1 | 8/2017 | Root et al. |
| 2017/0319378 A1 | 11/2017 | Anderson et al. |
| 2017/0325992 A1 | 11/2017 | DeBenedictis et al. |
| 2017/0325993 A1 | 11/2017 | Jimenez Lozano et al. |
| 2017/0326042 A1 | 11/2017 | Zeng et al. |
| 2017/0326346 A1 | 11/2017 | Jimenez Lozano et al. |
| 2017/0340380 A1 | 11/2017 | Scheller et al. |
| 2017/0354465 A1 | 12/2017 | Rink et al. |
| 2018/0001107 A1 | 1/2018 | Schwarz et al. |
| 2018/0161197 A1 | 6/2018 | Baker et al. |
| 2018/0185081 A1 | 7/2018 | O'Neil et al. |
| 2018/0185189 A1 | 7/2018 | Weber et al. |
| 2018/0263677 A1 | 9/2018 | Hilton et al. |
| 2018/0271767 A1 | 9/2018 | Jimenez Lozano et al. |
| 2018/0310950 A1 | 11/2018 | Yee et al. |
| 2019/0000663 A1 | 1/2019 | Anderson et al. |
| 2019/0110828 A1 | 4/2019 | Despatie |
| 2019/0111252 A1 | 4/2019 | Kang |
| 2019/0117220 A1 | 4/2019 | Nativ et al. |
| 2019/0125424 A1 | 5/2019 | DeBenedictis et al. |
| 2019/0133642 A1 | 5/2019 | Ignon et al. |
| 2019/0142493 A1 | 5/2019 | DeBenedictis et al. |
| 2019/0201706 A1 | 7/2019 | Schwarz et al. |
| 2019/0224042 A1 | 7/2019 | Ting et al. |
| 2019/0365595 A1 | 12/2019 | Rosen et al. |
| 2020/0038234 A1 | 2/2020 | Jimenez Lozano et al. |
| 2020/0069458 A1 | 3/2020 | Pham |
| 2020/0100935 A1 | 4/2020 | DeBenedictis et al. |
| 2020/0138501 A1 | 5/2020 | DeBenedictis et al. |
| 2020/0155215 A1 | 5/2020 | Levinson et al. |
| 2020/0297526 A1 | 9/2020 | Yee et al. |
| 2022/0047315 A1 | 2/2022 | Baker et al. |
| 2022/0249857 A1 | 8/2022 | Schwarz et al. |
| 2023/0218915 A1 | 7/2023 | Casalino et al. |

FOREIGN PATENT DOCUMENTS

| | | |
|---|---|---|
| CA | 2585214 A1 | 10/2007 |
| CH | 333982 A | 11/1958 |
| CN | 86200604 U | 10/1987 |
| CN | 2514795 Y | 10/2002 |
| CN | 2514811 Y | 10/2002 |
| CN | 2617189 Y | 5/2004 |
| CN | 1511503 A | 7/2004 |
| CN | 1520276 A | 8/2004 |
| CN | 1741777 A | 3/2006 |
| CN | 1817990 A | 8/2006 |
| CN | 2843367 Y | 12/2006 |
| CN | 2850584 Y | 12/2006 |
| CN | 2850585 Y | 12/2006 |
| CN | 200970265 Y | 11/2007 |
| CN | 101259329 A | 9/2008 |
| CN | 101309657 A | 11/2008 |
| CN | 101351167 A | 1/2009 |
| CN | 101489541 A | 7/2009 |
| CN | 101909603 A | 12/2010 |
| CN | 102026596 A | 4/2011 |
| CN | 104127279 A | 11/2014 |
| CN | 104394813 A | 3/2015 |
| CN | 105473087 A | 4/2016 |
| DE | 532976 C | 9/1931 |
| DE | 2851602 A1 | 6/1980 |
| DE | 4213584 A1 | 11/1992 |
| DE | 4224595 A1 | 1/1994 |
| DE | 4238291 A1 | 5/1994 |
| DE | 4445627 A1 | 6/1996 |
| DE | 19800416 A1 | 7/1999 |
| EP | 263069 A2 | 4/1988 |
| EP | 397043 A1 | 11/1990 |
| EP | 406244 A1 | 1/1991 |
| EP | 560309 A1 | 9/1993 |
| EP | 598824 A1 | 6/1994 |
| EP | 1030611 A1 | 8/2000 |
| EP | 1201266 A1 | 5/2002 |
| EP | 0573576 B2 | 7/2003 |
| EP | 1568395 A1 | 8/2005 |
| EP | 2260801 A2 | 12/2010 |
| EP | 2289598 A1 | 3/2011 |
| EP | 2527005 A1 | 11/2012 |
| EP | 2904986 A1 | 8/2015 |
| FR | 854937 A | 4/1940 |
| FR | 2744358 A1 | 8/1997 |
| FR | 2745935 A1 | 9/1997 |
| FR | 2767476 A1 | 2/1999 |
| FR | 2776920 A1 | 10/1999 |
| FR | 2779893 A1 | 8/2000 |
| FR | 2805989 A1 | 9/2001 |
| GB | 387960 A | 2/1933 |
| GB | 578157 A | 6/1946 |
| GB | 2120944 A | 12/1983 |
| GB | 2202447 A | 9/1988 |
| GB | 2248183 A | 4/1992 |
| GB | 2263872 A | 8/1993 |
| GB | 2286660 A | 8/1995 |
| GB | 2323659 A | 9/1998 |
| GB | 2565139 A | 2/2019 |
| JP | S50-33039 Y2 | 9/1975 |
| JP | 58187454 A | 11/1983 |
| JP | S6094113 A | 5/1985 |
| JP | 62082977 A | 4/1987 |
| JP | 63076895 A | 4/1988 |
| JP | 01223961 A | 9/1989 |
| JP | 03051964 A | 3/1991 |
| JP | 03259975 A | 11/1991 |
| JP | 4093597 A | 3/1992 |
| JP | 6261933 A | 9/1994 |
| JP | 7194666 A | 8/1995 |
| JP | 7268274 A | 10/1995 |
| JP | 9164163 A | 6/1997 |
| JP | 10216169 A | 8/1998 |
| JP | 10223961 A | 8/1998 |
| JP | 3051964 U | 9/1998 |
| JP | 3065657 U | 2/2000 |
| JP | 2000503154 A | 3/2000 |

(56) References Cited

FOREIGN PATENT DOCUMENTS

| | | |
|---|---|---|
| JP | 2001046416 A | 2/2001 |
| JP | 2002125993 A | 5/2002 |
| JP | 2002224051 A | 8/2002 |
| JP | 2002282295 A | 10/2002 |
| JP | 2002290397 A | 10/2002 |
| JP | 2002543668 A | 12/2002 |
| JP | 2003190201 A | 7/2003 |
| JP | 2004013600 A | 1/2004 |
| JP | 2004073812 A | 3/2004 |
| JP | 2004159666 A | 6/2004 |
| JP | 2005039790 A | 2/2005 |
| JP | 2005065984 A | 3/2005 |
| JP | 2005110755 A | 4/2005 |
| JP | 2005509977 A | 4/2005 |
| JP | 3655820 B2 | 6/2005 |
| JP | 2005520608 A | 7/2005 |
| JP | 2005237908 A | 9/2005 |
| JP | 2005323716 A | 11/2005 |
| JP | 2006026001 A | 2/2006 |
| JP | 2006130055 A | 5/2006 |
| JP | 2006520949 A | 9/2006 |
| JP | 2007270459 A | 10/2007 |
| JP | 2008532591 A | 8/2008 |
| JP | 2009515232 A | 4/2009 |
| JP | 2009189757 A | 8/2009 |
| KR | 20-0173222 Y1 | 3/2000 |
| KR | 20040094508 A | 11/2004 |
| KR | 20090000258 U | 1/2009 |
| KR | 20130043299 A | 4/2013 |
| KR | 20140038165 A | 3/2014 |
| RU | 2036667 C1 | 6/1995 |
| RU | 2491337 C2 | 8/2013 |
| SU | 532976 A1 | 11/1978 |
| TW | 476644 B | 2/2002 |
| WO | WO-85/03216 A1 | 8/1985 |
| WO | WO-91/14417 A1 | 10/1991 |
| WO | WO-93/00807 A1 | 1/1993 |
| WO | WO-94/04116 A1 | 3/1994 |
| WO | WO-96/23447 A1 | 8/1996 |
| WO | WO-96/26693 A1 | 9/1996 |
| WO | WO-96/36293 A1 | 11/1996 |
| WO | WO-96/37158 A1 | 11/1996 |
| WO | WO-97/04832 A1 | 2/1997 |
| WO | WO-97/05828 A1 | 2/1997 |
| WO | WO-97/22262 A2 | 6/1997 |
| WO | WO-97/24088 A1 | 7/1997 |
| WO | WO-97/25798 A1 | 7/1997 |
| WO | WO-97/48440 A1 | 12/1997 |
| WO | WO-98/29134 A2 | 7/1998 |
| WO | WO-98/31321 A1 | 7/1998 |
| WO | WO-98/41156 A1 | 9/1998 |
| WO | WO-98/41157 A1 | 9/1998 |
| WO | WO-99/09928 A1 | 3/1999 |
| WO | WO-99/16502 A1 | 4/1999 |
| WO | WO-99/38469 A1 | 8/1999 |
| WO | WO-99/49937 A1 | 10/1999 |
| WO | WO-00/44346 A1 | 8/2000 |
| WO | WO-00/44349 A1 | 8/2000 |
| WO | WO-00/65770 A1 | 11/2000 |
| WO | WO-00/67685 A1 | 11/2000 |
| WO | WO-01/00269 A1 | 1/2001 |
| WO | WO-01/13989 A1 | 3/2001 |
| WO | WO-01/14012 A1 | 3/2001 |
| WO | WO-01/34048 A1 | 5/2001 |
| WO | WO-02/05736 A2 | 1/2002 |
| WO | WO-02/102921 A1 | 12/2002 |
| WO | WO-03/07859 A1 | 1/2003 |
| WO | WO-03/078596 A2 | 9/2003 |
| WO | WO-03/079916 A1 | 10/2003 |
| WO | WO-2004/000098 A2 | 12/2003 |
| WO | WO-2004/080279 A2 | 9/2004 |
| WO | WO-2004/090939 A2 | 10/2004 |
| WO | WO-2005/018433 A2 | 3/2005 |
| WO | WO-2005/023200 A2 | 3/2005 |
| WO | WO-2005/033957 A1 | 4/2005 |
| WO | WO-2005/046540 A1 | 5/2005 |
| WO | WO-2005/060354 A2 | 7/2005 |
| WO | WO-2005/096979 A1 | 10/2005 |
| WO | WO-2005/112815 A1 | 12/2005 |
| WO | WO-2006/066226 A1 | 6/2006 |
| WO | WO-2006/094348 A1 | 9/2006 |
| WO | WO-2006/106836 A1 | 10/2006 |
| WO | WO-2006/116603 A2 | 11/2006 |
| WO | WO-2006/127467 A2 | 11/2006 |
| WO | WO-2007/012083 A2 | 1/2007 |
| WO | WO-2007/028975 A1 | 3/2007 |
| WO | WO-2007/041642 A2 | 4/2007 |
| WO | WO-2007/101039 A1 | 9/2007 |
| WO | WO-2007/127924 A2 | 11/2007 |
| WO | WO-2007/145422 A1 | 11/2007 |
| WO | WO-2007/145421 A1 | 12/2007 |
| WO | WO-2008/006018 A2 | 1/2008 |
| WO | WO-2008/039556 A1 | 4/2008 |
| WO | WO-2008/039557 A1 | 4/2008 |
| WO | WO-2008/055243 A2 | 5/2008 |
| WO | WO-2008/143678 A1 | 11/2008 |
| WO | WO-2009/011708 A1 | 1/2009 |
| WO | WO-2009/026471 A1 | 2/2009 |
| WO | WO-2010/077841 A1 | 7/2010 |
| WO | WO-2010/127315 A2 | 11/2010 |
| WO | WO-2012/012296 A1 | 1/2012 |
| WO | WO-2012/103242 A1 | 8/2012 |
| WO | WO-2013/013059 A1 | 1/2013 |
| WO | WO-2013/075006 A1 | 5/2013 |
| WO | WO-2013/075016 A1 | 5/2013 |
| WO | WO-2013/190337 A1 | 12/2013 |
| WO | WO-2014/151872 A3 | 12/2014 |
| WO | WO-2014/191263 A1 | 12/2014 |
| WO | WO-2015/088368 A1 | 6/2015 |
| WO | WO-2015/117001 A1 | 8/2015 |
| WO | WO-2015/117005 A1 | 8/2015 |
| WO | WO-2015/117026 A2 | 8/2015 |
| WO | WO-2015/117032 A1 | 8/2015 |
| WO | WO-2015/117036 A2 | 8/2015 |
| WO | WO-2016/028796 A1 | 2/2016 |
| WO | WO-2016/048721 A1 | 3/2016 |

OTHER PUBLICATIONS

Aguilar et al., "Modeling Cryogenic Spray Temperature and Evaporation Rate Based on Single-Droplet Analysis," Eighth International Conference on Liquid Atomization and Spray Systems, Pasadena, CA, USA, Jul. 2000, 7 pages.

Al-Sakere, B. et al. "Tumor Ablation with Irreversible Electroporation," PLoS One, Issue 11, Nov. 2007, 8 pages.

Alster, T. et al., "Cellulite Treatment Using a Novel Combination Radiofrequency, Infrared Light, and Mechanical Tissue Manipulation Device," Journal of Cosmetic and Laser Therapy, vol. 7, 2005, pp. 81-85.

Ardevol, A. et al., "Cooling Rates of Tissue Samples During Freezing with Liquid Nitrogen," Journal of Biochemical and Biophysical Methods, vol. 27, 1993, pp. 77-86.

Arena, C. B. et al., "High-Frequency Irreversible Electroporation (H-FIRE) for Non-Thermal Ablation Without Muscle Contraction," BioMedical Engineering OnLine 2011, 10:102, Nov. 21, 2011, 21 pgs.

Becker, S. M. et al. "Local Temperature Rises Influence In Vivo Electroporation Pore Development: A Numerical Stratum Corneum Lipid Phase Transition Model," Journal of Biomechanical Engineering, vol. 129, Oct. 2007, pp. 712-721.

Bohm, T. et al., "Saline-Enhanced Radiofrequency Ablation of Breast Tissue: an in Vitro Feasibility Study," Investigative Radiology, vol. 35 (3), 2000, pp. 149-157.

Bondei, E. et al., "Disorders of Subcutaneous Tissue (Cold Panniculitis)," Dermatology in General Medicine, Fourth Edition, vol. 1, Chapter 108, 1993, Section 16, pp. 1333-1334.

Burge, S.M. et al., "Hair Follicle Destruction and Regeneration in Guinea Pig Skin after Cutaneous Freeze Injury," Cryobiology, 27(2), 1990, pp. 153-163.

(56) References Cited

OTHER PUBLICATIONS

Coban, Y. K. et al., "Ischemia-Reperfusion Injury of Adipofascial Tissue: An Experimental Study Evaluating Early Histologic and Biochemical Alterations in Rats," Mediators of Inflammation, 2005, 5, pp. 304-308.
Del Pino, M. E. et al. "Effect of Controlled Volumetric Tissue Heating with Radiofrequency on Cellulite and the Subcutaneous Tissue of the Buttocks and Thighs," Journal of Drugs in Dermatology, vol. 5, Issue 8, Sep. 2006, pp. 714-722.
Disclosure re: "Method and Apparatus for Regional Fat Reduction Using Controlled and Sustained Cooling of Skin Surface." Oct. 12, 2006. 7 pages.
Donski, P. K. et al., "The Effects of Cooling no Experimental Free Flap Survival," British Journal of Plastic Surgery, vol. 33, 1980, pp. 353-360.
Duck, F. A., Physical Properties of Tissue, Academic Press Ltd., chapters 4 & 5, 1990, pp. 73-165.
Duncan, W. C. et al., "Cold Panniculitis," Archives of Dermatology, vol. 94, Issue 6, Dec. 1966, pp. 722-724.
Epstein, E. H. et al., "Popsicle Panniculitis," The New England Journal of Medicine, 282(17), Apr. 23, 1970, pp. 966-967.
Fournier, L. et al. "Lattice Model for the Kinetics of Rupture of Fluid Bilayer Membranes," Physical Review, vol. 67, 2003, pp. 051908-1-051908-11.
Gabriel, S. et al., "The Dielectric Properties Of Biological Tissues: II. Measurements in the Frequency Range 10 Hz to 20 GHZ," Physics in Medicine and Biology, vol. 41, 1996, pp. 2251-2269.
Gage, A. "Current Progress in Cryosurgery," Cryobiology 25, 1988, pp. 483-486.
Gao, D. "A Study of Physical and Biological Mechanisms of Cryoinjury and Cryoprotection of Human Erythrocytes in Freezing Preservation" Department of Mechanical Engineering Thesis, Concordia University, Mar. 1991. 253 pages.
Gatto, H. "Effects of Thermal Shocks on Interleukin-1 Levels and Heat Shock Protein 72 (HSP72) Expression in Normal Human Keratinocytes," PubMed, Archives of Dermatological Research, vol. 284, Issue 7, 1992: pp. 414-417. [Abstract].
Golstein, P. et al. (2007). "Cell death by necrosis: Towards a molecular definition." Trends Biochem Sci. 32:1 37-43.
Groenendaal, et al., Quantifying the Composition of Human Skin for Glucose Sensor Development, Journal of Diabetes Science and Technology, vol. 4, Issue 5, Sep. 2010, pp. 1032-1040.
Hale, H. B. et al., "Influence of Chronic Heat Exposure and Prolonged Food Deprivation on Excretion of Magnesium, Phosphorus, Calcium, Hydrogen Ion & Ketones," Aerospace Medicine, vol. 39—No. 9, Sep. 1968, pp. 919-926.
Heller Page, E. et al., "Temperature-dependent skin disorders," Journal of the American Academy of Dermatology, vol. 18, No. 5, Pt 1, May 1988, pp. 1003-1019.
Hemmingsson, A. et al. "Attenuation in Human Muscle and Fat Tissue in Vivo and in Vitro," Acra Radiologica Diagnosis, vol. 23, No. 2, 1982, pp. 149-151.
Henry, F. et al., "Les Dermatoses Hivernales," Rev Med Liege, 54:11, 1999, pp. 864-866. [French Language and English Language Abstract Attached].
Hernan, P. et al., "Study for the evaluation of the efficacy of Lipocryolysis (EEEL)", Nov. 30, 2011. 8 pages.
Hernan, R. P., "A Study to Evaluate the Action of Lipocryolysis", 33(3) CryoLellers, 2012, pp. 176-180.
Holland, DB.et al. "Cold shock induces the synthesis of stress proteins in human keratinocytes," PubMed Journal of Investigative Dermatology; 101(2): Aug. 1993, pp. 196-199.
Holman, W. L. et al., "Variation in Cryolesion Penetration Due to Probe Size and Tissue Thermal Conductivity," The Annals of Thoracic Surgery, vol. 53, 1992, pp. 123-126.
Hong, J.S. et al., "Patterns of Ice Formation in Normal and Malignant Breast Tissue," Cryobiology 31, 1994, pp. 109-120.
Huang et al. "Comparative Proteomic Profiling of Murine Skin," Journal of Investigative Dermatology, vol. 121(1), Jul. 2003, pp. 51-64.
Isambert, H. "Understanding the Electroporation of Cells and Artificial Bilayer Membranes," Physical Review Letters, vol. 80, No. 15, 1998, pp. 3404-3707.
Jalian, H. R. et al., "Cryolipolysis: A Historical Perspective and Current Clinical Practice", 32(1) Semin. Cutan. Med. Surg., 2013, pp. 31-34.
Karch, J. et al. (2015). "Regulated Necrotic Cell Death." Circulation Research, 116: 1800-1809.
Kellum, R. E. et al., "Sclerema Neonatorum: Report of Case and Analysis of Subcutaneous and Epidermal-Dermal Lipids by Chromatographic Methods," Archives of Dermatology, vol. 97, Apr. 1968, pp. 372-380.
Koska, J. et al., "Endocrine Regulation of Subcutaneous Fat Metabolism During Cold Exposure in Humans," Annals of the New York Academy of Sciences, vol. 967, 2002, pp. 500-505.
Kundu, S. K. et al., "Breath Acetone Analyzer: Diagnostic Tool to Monitor Dietary Fat Loss," Clinical Chemistry, vol. 39, Issue (1), 1993, pp. 87-92.
Kundu, S. K. et al., "Novel Solid-Phase Assay of Ketone Bodies in Urine," Clinical Chemistry, vol. 37, Issue (9), 1991, pp. 1565-1569.
Kuroda, S. et al. "Thermal Distribution of Radio-Frequency Inductive Hyperthermia Using an Inductive Aperture-Type Applicator: Evaluation of the Effect of Tumor Size and Depth", Medical and Biological Engineering and Computing, vol. 37, 1999, pp. 285-290.
L'Vova, S.P. "Lipid Levels and Lipid Peroxidation in Frog Tissues During Hypothermia and Hibernation" Ukrainskii Biokhimicheskii Zhurnal, vol. 62, Issue 1, 1990, pp. 65-70. [English language summary—p. 69].
Laugier, P. et al., "In Vivo Results with a New Device for Ultrasonic Monitoring of Pig Skin Cryosurgery: The Echographic Cryprobe," The Society for Investigative Dermatology, Inc., vol. 111, No. 2, Aug. 1998, pp. 314-319.
Levchenko et al., "Effect of Dehydration on Lipid Metabolism" Ukrainskii Biokhimicheskii Zhurnal, vol. 50, Issue 1, 1978, pp. 95-97. [English language summary—p. 97].
Lidagoster, MD et al., "Comparison of Autologous Fat Transfer in Fresh, Refrigerated, and Frozen Specimens: An Animal Model," Annals of Plastic Surgery, vol. 44, No. 5, May 2000, pp. 512-515.
Liu, A. Y.-C. et al., "Transient Cold Shock Induces the Heat Shock Response upon Recovery at 37 C in Human Cells," Journal of Biological Chemistry, 269(20), May 20, 1994, pp. 14768-14775.
Maize, J.C. "Panniculitis," Cutaneous Pathology, Chapter 13, 1998, 327-344.
Malcolm, G. T. et al., "Fatty Acid Composition of Adipose Tissue in Humans: Differences between Subcutaneous Sites," The American Journal of Clinical Nutrition, vol. 50, 1989, pp. 288-291.
Manstein, D. et al. "A Novel Cryotherapy Method of Non-Invasive, Selective Lipolysis," LasersSurg. Med 40:S20, 2008, p. 104.
Manstein, D. et al. "Selective Cryolysis: A Novel Method of Non-Invasive Fat Removal," Lasers in Surgery and Medicine: The Official Journal of the ASLMS, vol. 40, No. 9, Nov. 2008, pp. 595-604.
Mayoral, "Case Reports: Skin Tightening with a Combined Unipolar and Bipolar Radiofrequency Device," Journal of Drugs in Dermatology, 2007, pp. 212-215.
Mazur, P. "Cryobiology: The Freezing of Biological Systems," Science, 68, 1970, pp. 939-949.
Merrill, T. "A Chill to the Heart: A System to Deliver Local Hypothermia Could One Day Improve the Lives of Heart-Attack Patients," Mechanical Engineering Magazine, Oct. 2010, 10 pages.
Miklavcic, D. et al. "Electroporation-Based Technologies and Treatments," The Journal of Membrane Biology (2010) 236:1-2, 2 pgs.
Moschella, S. L. et al., "Diseases of the Subcutaneous Tissue," in Dermatology, Second Edition, vol. 2, 1985 Chapter 19, Section II (W.B. Saunders Company, 1980) pp. 1169-1181.
Murphy, J. V. et al., "Frostbite: Pathogenesis and Treatment" The Journal of Trauma: Injury, Infection, and Critical Care, vol. 48, No. 1, Jan. 2000, pp. 171-178.
Nagao, T. et al., "Dietary Diacylglycerol Suppresses Accumulation of Body Fat Compared to Triacylglycerol in Men a Double-Blind Controlled Trial," The Journal of Nutrition, vol. 130, Issue (4), 2000, pp. 792-797.

(56) References Cited

OTHER PUBLICATIONS

Nagle, W. A. et al. "Cultured Chinese Hamster Cells Undergo Apoptosis After Exposure to Cold but Nonfreezing Temperatures," Cryobiology 27, 1990, pp. 439-451.
Nagore, E. et al., "Lipoatrophia Semicircularis-a Traumatic Panniculitis: Report of Seven Cases and Review of the Literature," Journal of the American Academy of Dermatology, vol. 39, Nov. 1998, pp. 879-881.
Nanda, G.S. et al., "Studies on electroporation of thermally and chemically treated human erythrocytes," Bioelectrochemistry and Bioenergetics, 34, 1994, pp. 129-134, 6 pgs.
Narins, D.J. et al. "Non-Surgical Radiofrequency Facelift", The Journal of Drugs in Dermatology, vol. 2, Issue 5, 2003, pp. 495-500.
Nielsen, B. "Thermoregulation in Rest and Exercise," Acta Physiologica Scandinavica Supplementum, vol. 323 (Copenhagen 1969), pp. 7-74.
Nishikawa, H. et al. "Ultrastructural Changes and Lipid Peroxidation in Rat Adipomusculocutaneous Flap Isotransplants after Normothermic Storage and Reperfusion," Transplantation, vol. 54, No. 5, 1992, pp. 795-801.
Nurnberger, F. "So-Called Cellulite: An Invented Disease," Journal of Dermatologic Surgery and Oncology, Mar. 1978, pp. 221-229.
Pease, G. R. et al., "An Integrated Probe for Magnetic Resonance Imaging Monitored Skin Cryosurgery," Journal of Biomedical Engineering, vol. 117, Feb. 1995, pp. 59-63.
Pech, P. et al., "Attenuation Values, vol. Changes and Artifacts in Tissue Due to Freezing," Acta Radiologica, vol. 28, Issue 6, 1987, pp. 779-782.
Peterson, L. J. et al., "Bilateral Fat Necrosis of the Scrotum," Journal of Urology, vol. 116, 1976, pp. 825-826.
Phinney, S. D. et al., "Human Subcutaneous Adipose Tissue Shows Site-Specific Differences in Fatty Acid Composition," The American Journal of Clinical Nutrition, vol. 60, 1994, pp. 725-729.
Pierard, G.E. et al., "Cellulite: From Standing Fat Herniation to Hypodermal Stretch Marks," The American Journal of Dermatology, vol. 22, Issue 1, 2000, pp. 34-37, [Abstract].
Pope, K. et al. "Selective Fibrous Septae Heating: An Additional Mechanism of Action for Capacitively Coupled Monopolar Radiofrequency" Thermage, Inc. Article, Feb. 2005, 6 pgs.
Quinn, P. J. "A Lipid-Phase Separation Model of Low-Temperature Damage to Biological Membranes," Cryobiology, 22, 1985, 128-146.
Rabi, T. et al., "Metabolic Adaptations in Brown Adipose Tissue of the Hamster in Extreme Ambient Temperatures," American Journal of Physiology, vol. 231, Issue 1, Jul. 1976, pp. 153-160.
Renold, A.E. et al. "Adipose Tissue" in Handbook of Physiology, Chapter 15, (Washington, D.C., 1965) pp. 169-176.
Ribeiro, A.S. et al. (2015). "Main Benefits and Applicability of Plant Extracts in Skin Care Products." Cosmetics 2(2): 48-65. cosmetics2020048.
Rock, K. L. et al. (2008). "The Inflammatory Response to Cell Death" Annual Review Pathology 3:1, 99-126.
Rossi, A. B. R. et al. "Cellulite: a Review," European Academy of Dermatology and Venercology, 2000, pp. 251-262, 12 pgs.
Rubinsky, B. "Principles of Low Temperature Cell Preservation," Heart Failure Reviews, vol. 8, 2003, pp. 277-284.
Rubinsky, B. et al., "Cryosurgery: Advances in the Application of Low Temperatures to Medicine," International Journal of Refrigeration, vol. 14, Jul. 1991, pp. 190-199.
Saleh, K.Y. et al., "Two-Dimensional Ultrasound Phased Array Design for Tissue Ablation for Treatment of Benign Prostatic Hyperplasia," International Journal of Hyperthermia, vol. 20, No. 1, Feb. 2004, pp. 7-31.
Schmidt, B. A., et al., "Intradermal adipocytes mediate fibroblast recruitment during skin wound healing," (2013) Development (Cambridge), 140 (7), pp. 1517-1527.
Schoning, P. et al., "Experimental Frostbite: Freezing Times, Rewarming Times, and Lowest Temperatures of Pig Skin Exposed to Chilled Air," Cryobiology 27, 1990, pp. 189-193.
Shephard, R. J. "Adaptation to Exercise in the Cold," Sports Medicine, vol. 2, 1985, pp. 59-71.
Sigma-Aldrich "Poly(ethylene glycol) and Poly(ethylene oxide)," http://www.sigmaaldrich.com/materials-science/materialscience-;products.htmi?TablePage=2020411 0, accessed Oct. 19, 2012. 1 page.
Smalls, L. K. et al. "Quantitative Model of Cellulite: Three-Dimensional Skin Surface Topography, Biophysical Characterization, and Relationship to Human Perception," International Journal of Cosmetic Science, vol. 27, Issue 5, Oct. 2005, 17 pgs.
Thermage, News Release, "Study Published in Facial Plastic Surgery Journal Finds Selective Heating of Fibrous Septae Key to Success and Safety of Thermage ThermaCool System," Jun. 20, 2005, 2 pages.
Vallerand et al. "Cold Stress Increases Lipolysis, FFA Ra and TG/FFA Cycling in Humans," Aviation, Space, and Environmental Medicine 70(1), 1999, pp. 42-50.
Wang, X. et al., "Cryopreservation of Cell/Hydrogel Constructs Based on a new Cell-Assembling Technique," Sep. 5, 2009, 40 pages.
Wharton, D. A. et al., "Cold Acclimation and Cryoprotectants in a Freeze-Tolerant Antarctic Nematode, Panagrolaimus Davidi,", Journal of Comparative Physiology, vol. 170, No. 4, Mar. 2000, 2 pages.
Winkler, C. et al., "Gene Transfer in Laboratory Fish: Model Organisms for the Analysis of Gene Function," in Transgenic Animals, Generation and Use (The Netherlands 1997), pp. 387-395.
Young, H. E. et al. "Isolation of Embryonic Chick Myosatellite and Pluripotent Stem Cells" The Journal of Tissue Culture Methods, vol. 14, Issue 2, 1992, pp. 85-92.
Zelickson, B. et al. "Cryolipolysis for Noninvasive Fat Cell Destruction: Initial Results from a Pig Model", 35 Dermatol. Surg., 2009, pp. 1-9.
Zouboulis, C. C. et al., "Current Developments and Uses of Cryosurgery in the Treatment of Keloids and Hypertrophic Scars," Wound Repair and Regeneration, vol. 10, No. 2, 2002, pp. 98-102.
Cohen, ML. (1977). "Measurement of The Thermal Properties of Human Skin. A review." J. Invest. Dermatol. 69, pp. 333-338.
Jimenez Lozano, J.N. et al. (2013). "Effect of Fibrous Septa in Radiofrequency Heating of Cutaneous and Subcutaneous Tissues: Computational Study," Lasers in Surgery and Medicine, 45 (5), pp. 326-338.
Beise, R.D. et al. (Jan. 1, 1998). "Psychophysical study of stinging pain evoked by brief freezing of superficial skin and ensuing short-lasting changes in sensations of cool and cold pain." Pain, vol. 74, Jan. 1, 1998 (Jan. 1, 1998), pp. 275-286, XP055620108, DOI: 10.1016/S0304-3959(97)00179-6.

* cited by examiner

METHODS, DEVICES, AND SYSTEMS FOR IMPROVING SKIN CHARACTERISTICS

CROSS-REFERENCE TO RELATED APPLICATIONS

The present application is a continuation of U.S. patent application Ser. No. 16/528,249, filed Jul. 31, 2019, now U.S. Pat. No. 11,446,175, issued Sep. 20, 2022, which claims the benefit of and priority to U.S. Provisional Patent Application No. 62/712,562, filed Jul. 31, 2018, which are incorporated herein by reference in their entirety.

BACKGROUND

Skin is made up of a surface epidermis layer and a thicker dermal layer immediately below the epidermis. A hypodermis area, also known as a subcutaneous layer, lies immediately below the dermis. This subcutaneous fat layer stores fat and serves to anchor the dermis to underlying muscles and bones.

Cryolipolysis is a non-invasive method for destroying lipid-rich cells (e.g., adipocytes) in subcutaneous fat by cooling target tissue in a controlled manner to reduce a volume of the fat and result in a slimmer aesthetically pleasing appearance. Cold temperatures are applied to the epidermis to cool the subcutaneous layer to a target temperature for a period of time sufficient to damage lipid-rich cells (e.g., adipocytes). These cells are then degraded and the lipids are removed over time by the body.

Cryolipolytic fat removal requires the temperature of the subcutaneous fat layer to be lowered to a sufficiently low temperature for a sufficiently long period of time to damage significant numbers of fat cells. A variety of specific protocols have been developed for achieving this. Generally, lipid-rich target tissue (e.g., subcutaneous fat) is lowered from a temperature of about 10° C. to about −25° C. for an interval of about 10 seconds to 30 minutes (see, e.g., U.S. Pat. No. 7,367,341). In certain protocols, multiple cooling cycles are utilized over the course of a single treatment session, with cooling cycles separated by non-cooling cycles. Treatment sessions may be repeated several times over the course of days, weeks, or months.

Cold treatment can affect and damage fat cells and non-fat cells under certain conditions. Therefore, one factor limiting the application of cryolipolysis is the potential for damage to the surrounding epidermis due to overexposure to cold temperatures. For this reason, fat removal protocols generally seek to limit exposure time and/or keep temperatures above certain thresholds to prevent or minimize damage to non-fat cells.

SUMMARY

Provided herein in certain embodiments are methods of improving one or more skin characteristics in a subject comprising cooling the subject's skin at a target site to a degree that alters adipocyte signaling but does not produce significant destruction of subcutaneous lipid-rich cells, wherein said alteration of adipocyte signaling produces an improvement in one or more skin characteristics. In certain embodiments, less than 10% of the subcutaneous lipid-rich cells are destroyed. In certain embodiments, less than 1%, 2%, 3%, 4%, 5%, or 7% of the subcutaneous lipid-rich cells are destroyed. In some embodiments, said cooling does not produce any adverse skin effects. In certain embodiments, said adverse effects are selected from the group consisting of hyper-pigmentation, hypo-pigmentation, unwanted blistering, unwanted scarring, permanent undesirable alterations, and disfiguring scars. In certain embodiments, said alteration in adipocyte signaling results in an increase in expression of one or more cytokines selected from the group consisting of TGF-β, TNF-α, IL-1β, IL-6, MCP-1, leptin, adiponectin, resistin, acylation-stimulating protein, alpha 1 acid glycoprotein, pentraxin-3, IL-1 receptor antagonist, macrophage migration inhibitor factor, and SAA3. In some embodiments, said increase in expression occurs in the dermal layer, the subcutaneous layer, or both. In certain embodiments, said alteration in adipocyte signaling results in an increase in one or more extracellular matrix components selected from the group consisting of collagen, elastin, proteoglycans (e.g., heparan sulfate, keratin sulfate, and chondroitin sulfate), fibrinogen, laminin, fibrin, fibronectin, hyaluronan, hyaluronic acid, versican, aggrecan, lumican, decorin, glypican, tenascins, syndecans, integrins, discoidin domain receptors, perlecan, N-CAM, ICAM, VCAM, focal adhesion kinases, matrix metalloproteases, and Rho-kinases. In some embodiments, increase in one or more extracellular matrix components occurs in the epidermal layer, dermal layer, the subcutaneous layer, or combinations thereof. In certain embodiments, said one or more improved skin characteristics are selected from the group consisting of increased skin thickness, increased new collagen content, increased skin firmness, increased skin smoothness, skin tightening, increased dermal/epidermal hydration, dermal remodeling, and fibrous septae thickening.

Provided herein in certain embodiments are methods of improving one or more skin characteristics in a subject comprising cooling the subject's skin at a target site to a degree that alters adipocyte signaling but does not produce significant destruction of subcutaneous lipid-rich cells, wherein said alteration of adipocyte signaling produces an improvement in one or more skin characteristics. In certain embodiments, said cooling is performed by applying a treatment unit proximal to the target site. In certain embodiments, the temperature of said treatment unit is about −18° C. to about 0° C. In some embodiments, said cooling lowers the temperature of the epidermis at the target site to about −15° C. to about 5° C. In certain embodiments, said cooling is discontinued after the temperature of the epidermis at the target site has been at a temperature of about −15° C. to about 5° C. for about 10 minutes to about 25 minutes. In certain embodiments, said cooling does not lower the temperature of the subcutaneous fat layer 7 mm below the target site below about 3° C. In some embodiments, said cooling lowers the temperature of the subcutaneous fat layer 7 mm below the target site to about 3° C. to about 30° C. In certain embodiments, said cooling is discontinued after the temperature of the subcutaneous fat layer 7 mm below the target site has been at a temperature of about 3° C. to about 30° C. for about 10 minutes to about 25 minutes. In some embodiments, said cooling is discontinued before the temperature of the subcutaneous fat layer 7 mm below the target site falls below 3° C. In certain embodiments, said cooling is repeated two or more times separated by re-warming periods during a single treatment session.

Provided herein in certain embodiments are methods of improving one or more skin characteristics in a subject comprising applying a cooling element proximal to a target site on the subject's skin for a period of time sufficient to cool the epidermis at the target site to about −15° C. to about 5° C., wherein said cooling results in an alteration of one or more adipocyte signaling events; and removing the cooling element before the temperature of the subcutaneous fat layer about 7 mm below the target site decreases below a temperature of +3C. In certain embodiments, the temperature of the subcutaneous fat layer about 7 mm below the target site is decreased to about 3° C. to about 15° C. during application of the cooling element. In certain embodiments, less than 10% of the subcutaneous lipid-rich cells in the entire subcutaneous fat layer are destroyed. In some embodiments, less than either 1%, 2%, 3%, 4%, 5%, or 7% of the subcutaneous lipid-rich cells are destroyed.

Provided herein in certain embodiments are methods of improving one or more skin characteristics in a subject comprising applying a cooling element proximal to a target site on the subject's skin for a period of time sufficient to cool the epidermis at the target site to about −15° C. to about 5° C., wherein said cooling results in an alteration of one or more adipocyte signaling events; and removing the cooling element before the temperature of the entire subcutaneous fat layer beneath the target site is decreased to a level that produces significant destruction of subcutaneous lipid-rich cells therein. In certain embodiments, the temperature of the subcutaneous fat layer about 7 mm below the target site is decreased to about 3° C. to about 15° C. during application of the cooling element. In certain embodiments, less than 10% of the subcutaneous lipid-rich cells in the entire subcutaneous fat layer are destroyed. In some embodiments, less than either 1%, 2%, 3%, 4%, 5%, or 7% of the subcutaneous lipid-rich cells are destroyed.

Provided herein in certain embodiments are methods of increasing new collagen formation in a subject comprising cooling the subject's skin at a target site to a degree that alters adipocyte signaling but does not produce significant destruction of subcutaneous lipid-rich cells, wherein said alteration of adipocyte signaling increases new collagen formation. Also provided herein in certain embodiments are methods of increasing new collagen formation in a subject comprising applying a cooling element proximal to a target site on the subject's skin for a period of time sufficient to cool the epidermis at the target site to about −15° C. to about 5° C., wherein said cooling results in an alteration of one or more adipocyte signaling events and an increase in new collagen formation; and removing the cooling element before the temperature of the subcutaneous fat layer about 7 mm below the target site decreases below a temperature of +3C. Further provided herein in certain embodiments are methods of increasing new collagen formation in a subject comprising applying a cooling element proximal to a target site on the subject's skin for a period of time sufficient to cool the epidermis at the target site to about −15° C. to about 5° C., wherein said cooling results in alteration of adipocyte signaling and an increase in new collagen formation; and removing the cooling element before the temperature of the entire subcutaneous fat layer beneath the target site is decreased to a level that produces significant destruction of subcutaneous lipid-rich cells therein. In certain embodiments, collagen formation is increased in the dermal fat layer. In certain embodiments, collagen formation is increased in the basal epidermal junction (e.g., attaches the basal lamina to the dermis), dermis, and fibrous septae.

Provided herein in certain embodiments are methods of decreasing skin laxity in a subject comprising cooling the subject's skin at a target site to a degree that alters adipocyte signaling but does not produce significant destruction of subcutaneous lipid-rich cells, wherein said alteration of adipocyte signaling decreases skin laxity. Also provided herein in certain embodiments are methods of decreasing skin laxity in a subject comprising applying a cooling element proximal to a target site on the subject's skin for a period of time sufficient to cool the epidermis at the target site to about −15° C. to about 5° C., wherein said cooling results in an alteration of one or more adipocyte signaling events and a decrease in skin laxity; and removing the cooling element before the temperature of the subcutaneous fat layer about 7 mm below the target site decreases below a temperature of +3C. Further provided herein in certain embodiments are methods of decreasing skin laxity in a subject comprising applying a cooling element proximal to a target site on the subject's skin for a period of time sufficient to cool the epidermis at the target site to about −15° C. to about 5° C., wherein said cooling results in an alteration of one or more adipocyte signaling events and a decrease in skin laxity; and removing the cooling element before the temperature of the entire subcutaneous fat layer beneath the target site is decreased to a level that produces significant destruction of subcutaneous lipid-rich cells therein.

Provided herein in certain embodiments are methods of increasing skin thickness comprising cooling the subject's skin at a target site to a degree that alters adipocyte signaling but does not produce significant destruction of subcutaneous lipid-rich cells, wherein said alteration of adipocyte signaling produces an increase in skin thickness. Also provided herein in certain embodiments are methods of increasing skin thickness in a subject comprising applying a cooling element proximal to a target site on the subject's skin for a period of time sufficient to cool the epidermis at the target site to about −15° C. to about 5° C., wherein said cooling results in an alteration of one or more adipocyte signaling events and an increase in skin thickness; and removing the cooling element before the temperature of the subcutaneous fat layer about 7 mm below the target site decreases below a temperature of +3C. Further provided herein in certain embodiments are methods of increasing skin thickness in a subject comprising applying a cooling element proximal to a target site on the subject's skin for a period of time sufficient to cool the epidermis at the target site to about −15° C. to about 5° C., wherein said cooling results in an alteration of one or more adipocyte signaling events and an increase in skin thickness; and removing the cooling element before the temperature of the entire subcutaneous fat layer beneath the target site is decreased to a level that produces significant destruction of subcutaneous lipid-rich cells therein.

Provided herein in certain embodiments are systems for use in the methods disclosed herein. Also provided herein in some embodiments are systems for improving one or more skin characteristics in a subject, comprising a treatment unit; and an applicator having a cooling unit in communication with the treatment unit, wherein the applicator is configured to cool the subject's skin at a target site to a degree that alters adipocyte signaling but does not produce significant destruction of subcutaneous lipid-rich cells. In some embodiments, a temperature of said treatment unit is about −18° C. to about 0° C. In certain embodiments, when said applicator cools the subject's skin, said cooling lowers the temperature of an epidermis at the target site to about −15° C. to about 5° C. In certain embodiments, when said applicator cools the subject's skin, said cooling is discontinued after the temperature of the epidermis at the target site has been at a temperature of about −15° C. to about 5° C. for about 10 minutes to about 25 minutes. In some embodiments, when said applicator cools the subject's skin, said cooling does not lower the temperature of the subcutaneous fat layer 7 mm below the target site below about 3° C. In certain embodiments, when said applicator cools the subject's skin, said cooling lowers the temperature of the subcutaneous fat layer 7 mm below the target site to about 3° C. to about 30° C. In certain embodiments, when said applicator cools the subject's skin, said cooling is discontinued after the temperature of the subcutaneous fat layer 7 mm below the target site has been at a temperature of about 3° C. to about 30° C. for about 10 minutes to about 25 minutes. In some embodiments, when said applicator cools the subject's skin, said cooling is discontinued before the temperature of the subcutaneous fat layer 7 mm below the target site falls below 3° C. In certain embodiments, when said applicator cools the subject's skin, said cooling is repeated two or more times separated by re-warming periods during a single treatment session. In some embodiments, when the applicator alters adipocyte signaling, an improvement in one or more skin characteristics is produced.

Provided herein in some embodiments are systems for improving one or more skin characteristics in a subject, comprising a treatment unit; and an applicator having a cooling unit in communication with the treatment unit, wherein the applicator is configured to cool the subject's skin at a target site to a degree that alters adipocyte signaling but does not produce significant destruction of subcutaneous lipid-rich cells. In some embodiments, less than 10% of the subcutaneous lipid-rich cells are destroyed. In certain embodiments, less than 1%, 2%, 3%, 4%, 5%, or 7% of the subcutaneous lipid-rich cells are destroyed. In certain embodiments, when the applicator cools the subject's skin at the target site, the cooling does not produce any adverse skin effects. In some embodiments, said adverse effects are selected from the group consisting of hyper-pigmentation, hypo-pigmentation, unwanted blistering, unwanted scarring, permanent undesirable alterations, and disfiguring scars. In certain embodiments, when the applicator alters adipocyte signaling, said alteration results in an increase in expression of one or more cytokines selected from the group consisting of TGF-β, TNF-α, IL-1β, IL-6, MCP-1, leptin, adiponectin, resistin, acylation-stimulating protein, alpha 1 acid glycoprotein, pentraxin-3, IL-1 receptor antagonist, macrophage migration inhibitor factor, and SAA3. In some embodiments, when the applicator alters adipocyte signaling, said increase in expression occurs in the dermal layer, the subcutaneous layer, or both. In certain embodiments, when the applicator alters adipocyte signaling, said alteration results in an increase in one or more extracellular matrix components selected from the group consisting of collagen, elastin, proteoglycans (e.g., heparan sulfate, keratin sulfate, and chondroitin sulfate), fibrinogen, laminin, fibrin, fibronectin, hyaluronan, hyaluronic acid, versican, aggrecan, lumican, decorin, glypican, tenascins, syndecans, integrins, discoidin domain receptors, perlecan, N-CAM, ICAM, VCAM, focal adhesion kinases, matrix metalloproteases, and Rho-kinases. In certain embodiments, when the applicator alters adipocyte signaling, said increase in one or more extracellular matrix components occurs in the epidermal layer, dermal layer, the subcutaneous layer, or combinations thereof. In certain embodiments, when the applicator alters adipocyte signaling, said one or more improved skin characteristics are selected from the group consisting of increased skin thickness, increased new collagen content, increased skin firmness, increased skin smoothness, skin tightening, increased dermal/epidermal hydration, dermal remodeling, and fibrous septae thickening.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, identical reference numbers identify similar elements or acts. The sizes and relative positions of elements in the drawings are not necessarily drawn to scale. For example, the shapes of various elements and angles may not be drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

DETAILED DESCRIPTION

Figure 1A:
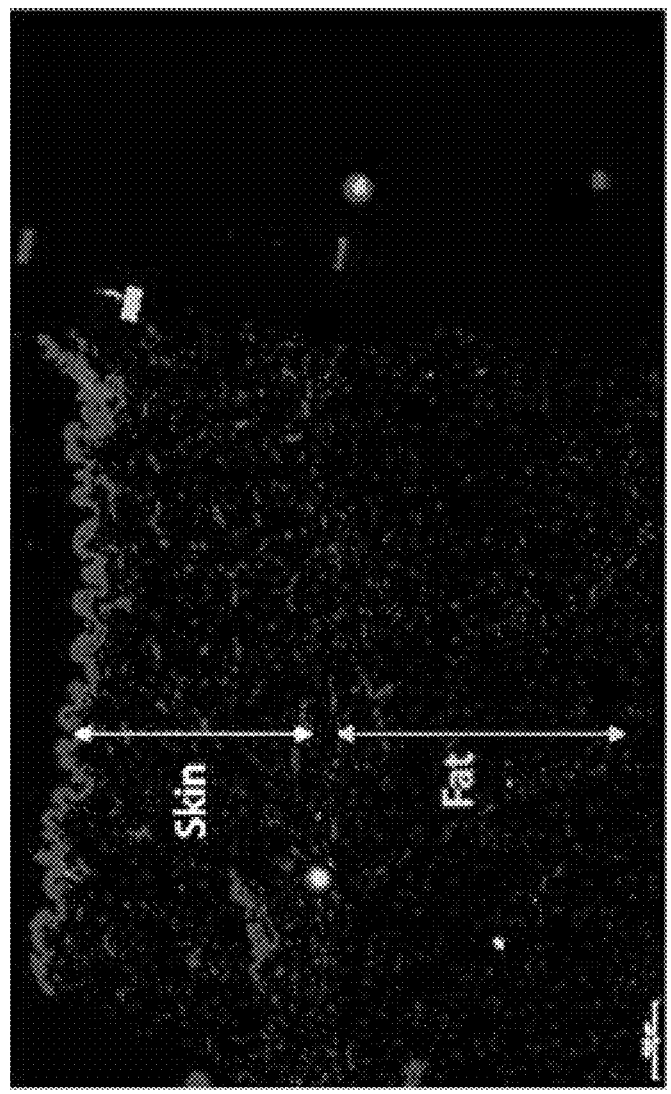
FIGS. 1A-1D: Representative tissue sections showing the effect of controlled epidermal cooling on TGF-β mRNA expression in skin and adipose tissue visualized by in situ hybridization. Fluorescence pseudocolor: TGF-β mRNA mRNA=Cy5, yellow. Nucleus=TRITC, blue. 1A: Control (untreated tissue) with no change in TGF-β mRNA expression in skin and fat tissue. 1B-1D: 3 weeks post-treatment. 1B: Slide showing a strong signal of Cy5 representing elevated expression of TGF-β mRNA in dermal and subcutaneous adipose tissue post-treatment. 1C and 1D: Magnifications of dermal and subcutaneous fat, respectively, showing elevated expression of TGF-β mRNA around adipocytes (arrows).

The following description of the invention is merely intended to illustrate various embodiments of the invention. As such, the specific modifications discussed herein are not to be construed as limitations on the scope of the invention. It will be apparent to one skilled in the art that various equivalents, changes, and modifications may be made without departing from the scope of the invention, and it is understood that such equivalent embodiments are to be included herein.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, stages, or characteristics may be combined in any suitable manner in one or more examples of the technology. The headings provided herein are for convenience only and are not intended to limit or interpret the scope or meaning of the technology.

The methods, systems, and devices provided herein are based on the unexpected finding that epidermal cooling performed at a temperature and for a time that is insufficient to cause significant damage to underlying subcutaneous lipid-rich cells activates one or more adipocyte signaling pathways in epidermal, dermal and subcutaneous fat sufficient to cause various beneficial effects in the adjacent dermal and epidermal layers, including improvements in skin appearance that might otherwise occur when epidermal cooling is performed at a temperature and for a time sufficient to cause significant damage (e.g., damage in excess of 20%) to the underlying subcutaneous lipid-rich cells. In some embodiments, the beneficial effects on the dermal and epidermal layers (e.g., skin) occur in response to activation of the one or more adipocyte signaling pathways which result in changes to the subject's subcutaneous layer. For example, increased production of collagen in the subject's subcutaneous layer, dermal and/or epidermal layer can result in improved skin appearance.

These unexpected findings are illustrated by the experimental examples set forth below, which show that administration of controlled epidermal cooling performed at a temperature and for a time to produce a significant increase in TGF-β mRNA expression in both dermal and subcutaneous fat, with the effect on subcutaneous fat being most pronounced. As used herein, the terms "controlled cooling" or "controlled epidermal cooling" may be used interchangeably and refer to cooling of a subject's epidermis that is performed at a temperature and for a time that is insufficient to cause significant damage to underlying subcutaneous lipid-rich cells. Controlled cooling performed also produced a significant increase in collagen COL1A1 mRNA expression in fat, with a concomitant increase in collagen synthesis near treated fat tissue, such as in the subcutaneous layer and dermal and/or epidermal layers. Increased collagen production is associated with a host of beneficial aesthetic effects, including, for example, tighter, smoother skin with fewer visible lines and wrinkles or less pronounced lines and wrinkles. Based on these results, the effects of controlled epidermal cooling on skin thickness was evaluated in human subjects. Subjects exhibited a significant increase in thigh skin thickness 12 weeks following their last treatment.

The terms "controlled sub-cryolipolytic cooling" and "sub-cryolipolysis" as used herein refer to controlled cooling of the epidermis, and any concomitant cooling of the adjacent dermal and subcutaneous layers that lie beneath the epidermis being cooled, that does not result in significant damage to or destruction of subcutaneous fat cells. In other words, it does not result in damaging 20% or more of the subcutaneous fat cells.

Although certain beneficial skin effects have been observed previously in conjunction with cryolipolytic fat removal procedures, it had been assumed that these benefits were the result of significant damage to and/or destruction of subcutaneous lipid-rich cells throughout the subcutaneous layer. The results disclosed herein provide the first indication that beneficial skin effects may also be obtained using sub-cryolipolytic cooling protocols that do not damage, or that minimally damage, lipid-rich cells in the subcutaneous layer (e.g., controlled cooling). Without intending to be bound by any particular theory, it is thought that certain signaling events which occur during cryolipolysis (e.g., cooling treatments delivered by a skin surface applicator which has a temperature of about −11° C. and is applied to skin for about 35 minutes) are also induced during use of sub-cryolipolytic cooling protocols. However, unlike cryolipolysis, which causes significant damage to and/or destruction of subcutaneous lipid-rich cells throughout the subject's subcutaneous layer, sub-cryolipolytic cooling protocols do not cause the same or generally similar significant damage and/or destruction. While the upper third or about the upper third of the subject's subcutaneous layer is being treated to and/or using the same, similar, or generally similar temperatures with cryolipolysis and sub-cryolipolysis, a duration of the temperature applied to the upper third of the subject's subcutaneous layer is shorter during sub-cryolipolysis compared to cryolipolysis. It is thought that the shorter durations of temperature used during sub-cryolipolysis result in reduced damage to the subject and fewer fat cells being destroyed and/or damaged compared to cryolipolysis while maintaining the same, similar, or generally similar level, amount, type, and/or degree of signaling events in the subject following sub-cryolipolytic or cryolipolytic therapy.

Provided herein in certain embodiments are methods for altering adipocyte signaling in a subject comprising cooling the subject's skin at a target site to a degree that alters adipocyte signaling but does not produce significant damage to subcutaneous lipid-rich cells. In certain embodiments, these methods result in improvements to one or more skin characteristics. Accordingly, also provided herein are methods of improving one or more skin characteristics in a subject comprising cooling the subject's skin at a target site to a degree that alters adipocyte signaling but does not produce significant damage to subcutaneous lipid-rich cells. Examples of skin characteristics that may be improved using these methods including, but are not limited to, thickness, firmness, smoothness, tightness, dermal/epidermal hydration, and collagen content. Accordingly, provided herein in certain embodiments are methods of increasing skin and/or fibrous septae thickness, increasing collagen production, increasing collagen content, increasing skin firmness, increasing skin smoothness, increasing skin tightness, and increasing dermal and/or epidermal hydration in a subject. In certain embodiments, the methods provided herein may be used for dermal remodeling, regenerative remodeling, healing skin (e.g., wound healing), or enhancing a skin healing response.

A "target site" as used herein refers to a portion of a subject's epidermis (e.g., an outer surface of the subject's skin) that is subjected to controlled cooling. In those embodiments where controlled cooling is carried out using a treatment unit (e.g., cooling unit) placed in direct contact with a subject's skin, the target site includes at least that portion of the skin that is in direct contact with the treatment unit and the skin therebeneath.

In certain of these embodiments, application of controlled cooling to the target site may generate a "treatment site" which includes the target site and a portion of the subject's body which extends radially inward from the area of contact, for example, the portion of the subject's body which comprises at least a portion of the treatment site radially extends at least about 1 mm, at least about 2 mm, at least about 3 mm, at least about 5 mm, at least about 10 mm, at least about 15 mm, at least about 20 mm, at least about 30 mm, at least about 40 mm, or at least about 50 mm from the portion of the skin that is in direct contact with the treatment unit. In other embodiments, the treatment site can include the subject's body or at least a large portion of the subject's body. In these embodiments, controlled cooling applied to the target site can activate one or more signaling pathways in the subject that may result in one or more systemic signaling events, or generally systemic signaling events.

In some embodiments, the subject's epidermis can be controllably cooled to a target temperature within a temperature range of about −40° C. to about 10° C., or to a target temperature within temperature ranges of about −25° C. to about 5° C., about −20° C. to about 5° C., or about −15° C. to about 5° C. In certain embodiments, the subject's subcutaneous layer can be cooled to the target temperature within any of the aforementioned target temperatures about 15 mm, about 10 mm, about 9 mm, about 8 mm, about 7 mm, about 6 mm, about 5 mm, about 4 mm, about 3 mm, about 2 mm, about 1 mm, or less than about 1 mm below the subject's skin (e.g., lower surface of the subject's skin). Without intending to be bound by any particular theory, it is thought that controlled cooling (e.g., sub-cryolipolytic cooling) can be achieved at any of the aforementioned depths thereby inducing one or more signaling events in the tissue that has been sub-cryolipolytically cooled. In these embodiments, one or more signaling events are not induced in tissue further below the surface of the subject's skin than any of the aforementioned depths. In some embodiments, the subject's epidermis (e.g., epidermal layer) is cooled to at least about 5° C. during sub-cryolipolysis and/or cryolipolysis.

In addition to cooling the subject's epidermis to certain temperatures, the present technology can also be used to cool the subject's subcutaneous layer (e.g., subcutaneous fat layer) about 1 mm to about 20 mm below the subject's dermal layer. In some embodiments, the subject's subcutaneous layer can be cooled to about −25° C. to about 20° C., or to about −15° C. to about 15° C., or to about 0° C. to about 15° C. about 1 mm, about 2 mm, about 3 mm, about 4 mm, about 5 mm, about 6 mm, about 7 mm, about 9 mm, about 14 mm, about 18 mm, or about 20 mm below the subject's dermal layer. Prior to application of controlled cooling, the subject's subcutaneous layer at any of the above depths can be about 35° C. to about 40° C., such as about 37° C. Methods of the present disclosure can, in some embodiments, include determining a subject's baseline subcutaneous temperature to at least about 20 mm below the subject's dermal layer using known technologies useful for determining subcutaneous temperature at the aforementioned depths.

Without intending to be limiting to the types of methods or parameters of the disclosed methods, example methods for determining temperatures (e.g., dermal, epidermal, and/or subcutaneous temperatures) include indirect measurements (e.g., heat transfer equations) specific for certain tissues (e.g., skin, fat, muscle), and compositions thereof, and direct measurements. In some embodiments, direct measurements are performed using one or more systems and/or devices configured to directly measure and/or determine temperatures, such as those configured to perform electrical impedance, optical, and/or crystallization measurements. Such systems can include a detector configured to extract, inter alia, temperature information from the epidermis, dermis, and/or fat cells as feedback to a control unit. The detected temperature information can be analyzed by control unit based on inputted properties and/or parameters. For example, the temperature of fat cells may be determined by calculation based on the temperature of the epidermis detected by detector. Thus, the treatment system may non-invasively measure the temperature of one or more fat cells. This information may then be used by a control unit for continuous feedback control of a treatment unit, for example, by adjusting the energy/temperature of a cooling/heating element and a treatment interface, thus maintaining optimal treatment temperature of target fat cells while controlling the treatment temperature and time so as to result in the surrounding epidermis and dermis not being unduly damaged. In some embodiments, the cooling/heating element can provide adjustable temperatures in the range of about −10° C. up to 42° C. An automated temperature measurement and control sequence can be repeated to maintain such temperature ranges until a procedure is complete.

It is noted that adipose tissue reduction by cooling lipid-rich cells may be even more effective when tissue cooling is accompanied by physical manipulation (e.g., massaging) of the target tissue. In accordance with an embodiment of the present invention, a treatment unit can include a tissue massaging device, such as a vibrating device and the like. Alternatively, a piezoelectric transducer can be used within the treatment unit in order to provide mechanical oscillation or movement of the cooling/heating element. The detector can include feedback devices for detecting changes in skin viscosity to monitor the effectiveness of treatment and/or to prevent any damage to surrounding tissue. For example, a vibration detecting device can be used to detect any change in the resonant frequency of the target tissue or surrounding tissue, which can indicate a change in tissue viscosity, being mechanically moved or vibrated by a vibrating device contained in the treatment unit.

To further ensure that the epidermis and/or the dermis is not damaged by cooling treatment, an optical detector/feedback device can be used to monitor the change of optical properties of the epidermis (enhanced scattering if ice formations occur); an electrical feedback device can be used to monitor the change of electric impedance of the epidermis caused by ice formation in the epidermis; and/or an ultrasound feedback device may be used for monitoring ice formation (actually to avoid) in the skin. Any such device may include signaling control unit to stop or adjust treatment to prevent or minimize skin damage.

In accordance with an embodiment of the invention, the treatment system may include a number of configurations and instruments. Algorithms that are designed for different types of procedures, configurations and/or instruments may be included for the control unit. The treatment system may include a probe controller and a probe for minimal invasive temperature measurement of fat cells. Advantageously, the probe may be capable of measuring a more accurate temperature of fat cells, thereby improving the control of the treatment unit and the effectiveness of treatment.

Controlled cooling can occur over a period of time inversely proportional to the temperature to avoid causing damage to the treatment site. For example, in some embodiments, the treatment unit is placed on the target site and cooling is applied for a time within a time range of about 10 seconds to about 2 hours. In these embodiments, a shorter time (e.g., about 10 seconds) is used when the target temperature is, for example, about −40° C. and a longer time (e.g., about 2 hours) is used when the target temperature is, for example, about 10° C. In some embodiments, the target temperature is within a temperature range of about −15° C. to about 0° C. and the cooling is applied for about 10 minutes to about 25 minutes. In other embodiments, the target temperature is within a temperature range of about −40° C. to about 0° C. and the cooling is applied for about 10 seconds to about 25 minutes. The epidermal temperature can be continuously or intermittently monitored before, during, and/or after controlled cooling treatment is applied using standard temperature measurement devices, systems, and/or methods.

"Destruction" of subcutaneous lipid-rich cells and "damage" to subcutaneous lipid-rich cells are used interchangeably herein and refer to cell killing, cell disruption, and/or cell crystallization. "Significant destruction" and "significant damage" are used interchangeably herein with regard to subcutaneous lipid-rich cells and refer to destruction of less than about 20%, less than about 19%, less than about 18%, less than about 17%, less than about 16%, less than about 15%, less than about 10%, less than about 8%, less than about 7%, less than about 5%, less than about 3%, less than about 2%, less than about 1%, less than about 0.5%, or less than about 0.1% of subcutaneous lipid-rich cells in a particular population of subcutaneous lipid-rich cells (e.g., all subcutaneous lipid-rich cells within a certain distance of a target site and/or at a specific depth below the target site and/or in a specific volume of the subcutaneous lipid-rich cells beneath the target site, such as throughout the entire volume, or throughout a specific fraction of the entire volume beneath the target site). In some embodiments, controlled cooling is insufficient to cause crystallization in subcutaneous lipid-rich cells but may still cause damage or significant damage to subcutaneous lipid-rich cells.

"Adipocyte signaling" as used herein refers to any signaling pathway that is initiated by an adipocyte, involves an adipocyte, or otherwise elicits a response from an adipocyte that the adipocyte would have not otherwise elicited or been involved in had it not been a part of the signaling pathway. In addition, adipocyte signaling also refers to a passive or active cascade of events that can remain passive or active, or some combination thereof, including intermittently passive and/or intermittently active, until homeostatic conditions return. Adipocyte signaling therefore includes one or more events where, after an adipocyte has been injured, one or more chemokines or cytokines are released which attract immune cells and/or inflammatory cells (e.g., macrophages) which can ultimately release TGF-β or other cytokines. Adipocyte signaling involves one or more molecules selected from the group consisting of cytokines, chemokines, adipokines, peptides, transcription factors (e.g., transcription factors associated with expression of or one or more signaling events involving TGF-β) nucleic acids, saccharides or other sugar or carbohydrate-based molecules, and lipids. These molecules can also include salts, bases, phosphates, esters, ethers, alkyls, or any other derivatives thereof. Cytokines and other molecules involved in adipocyte signaling are sometimes referred to herein as adipocyte signaling molecules.

"Altering" adipocyte signaling as used herein means increasing or decreasing the level of one or more adipocyte signaling molecules from a pre-treatment baseline level. The increases or decreases in adipocyte signaling molecules may be observed in the dermal layer, subcutaneous fat layer, or both layers.

In certain embodiments, an alteration in adipocyte signaling may be an increase in one or more adipocyte signaling molecules (e.g., an increase in expression (a nucleic acid encoding the molecule or the molecule itself), production, and/or secretion of one or more adipocyte signaling molecules). This increase may represent a signal being "turned on," i.e., activation of a previously inactive or nearly inactive adipocyte signal, or it may simply represent a signal being upregulated versus pre-treatment levels.

In certain embodiments, an alteration in adipocyte signaling may be a decrease in one or more adipocyte signaling molecules (e.g., a decrease in expression (a nucleic acid encoding the molecule or the molecule itself), production, and/or secretion of one or more adipocyte signaling molecules). This decrease may represent a signal being "turned off" entirely (i.e., deactivation of a previously active adipocyte signal), or it may simply represent a signal being downregulated versus pre-treatment levels.

In certain embodiments, an alteration in adipocyte signaling may be an increase in one or more adipocyte signaling molecules and a simultaneous decrease in one or more different adipocyte signaling molecules.

In certain embodiments of the methods disclosed herein, one or more of the adipocyte signaling molecules being increased or decreased by a direct and/or indirect response to cooling are cytokines, adipokines, and chemokines. For example, in certain embodiments, the methods provided herein may cause an increase in expression of tumor growth factor beta ("TGF-β"), tumor necrosis factor alpha ("TNF-α"), interleukin 1 beta ("IL-1β"), interleukin 6 ("IL-6"), and monocyte chemoattractant protein 1 ("MCP-1"), leptin, adiponectin, resistin, acylation-stimulating protein, alpha 1 acid glycoprotein, pentraxin-3, IL-1 receptor antagonist, macrophage migration inhibitor factor, and serum amyloid A3 ("SAA3"). In certain embodiments, the increase or decrease in cytokine levels occurs in the subject's dermal layer, subcutaneous fat layer, or both layers. In some embodiments, one or more of the adipocyte signaling molecules is expressed, released, induced, silenced, degraded, or otherwise modified in response to one or more extrinsic processes. When hypoxic, the adipocyte can increase expression of and/or release one or more cytokines. For example, an extrinsic process includes an adipocyte in hypoxic conditions caused to or otherwise affected by a change in the subject's oxygen and/or nutrient supply, such as that provided by the subject's blood microcirculation, or due to prolonged blood vasoconstriction. Accordingly, provided herein in certain embodiments are methods of increasing cytokine (e.g., TGF-β) levels in a subject, including increasing TGF-β levels in the subject's dermal layer, subcutaneous fat layer, or both, by cooling the subject's skin at a target site to a degree sufficient to increase TGF-β levels but insufficient to produce significant destruction of subcutaneous lipid-rich cells.

In certain embodiments of the methods provided herein, one or more of the adipocyte signaling molecules being increased or decreased by a direct and/or indirect response to cooling are extracellular matrix components. For example, in certain embodiments, the methods provided herein may cause an increase in collagen, elastin, proteoglycans (e.g., heparan sulfate, keratin sulfate, and chondroitin sulfate), fibrinogen, laminin, fibrin, fibronectin, hyaluronan, hyaluronic acid, versican, aggrecan, lumican, decorin, glypican, tenascins, syndecans, integrins, discoidin domain receptors, perlecan, and/or any molecules binding thereto, such as but not limited to, cell adhesion molecules (e.g., N-CAM, ICAM, VCAM), focal adhesion kinases, matrix metalloproteases, and Rho-kinases). In certain embodiments, these increases result in increased collagen production and/or content in the subject's dermal layer, subcutaneous fat layer, or both. In some embodiments, one or more alterations to one or more extracellular matrix components (e.g., ECM remodeling) are associated with the subject's fat cells. These alterations can result in the subject's skin feeling or have a perceived feeling of being more rigid, stiff, firm, or the like compared to how the subject's skin felt prior to treatment. However, these changes may not affect the skin itself directly but rather affect one or more structures directly or indirectly coupled to the subject's skin. In certain embodiments, ECM remodeling can have a threshold where the remodeling ends and results in a collagen matrix that is more robust (e.g., greater density, strength, and or length of collagen fibers) collagen matrix compared to the subject's collagen matrix prior to treatment.

Accordingly, provided herein in certain embodiments are methods of increasing collagen production and/or increasing collagen content in a subject by cooling the subject's skin at a target site to a degree sufficient to increase collagen production and/or increase collagen content but insufficient to produce significant destruction of subcutaneous lipid-rich cells. These methods may produce increased collagen production and/or collagen content in the dermal layer, the subcutaneous fat layer, or both.

In certain embodiments of the methods provided herein, adipocyte signaling is altered during the course of treatment only (i.e., signaling returns to around pre-treatment baseline levels at or around the time that cooling is discontinued). In other embodiments, adipocyte signaling remains altered for some period of time after cooling is discontinued. For example, adipocyte signaling may remain altered for 2 minutes, 15 minutes, 30 minutes, 1 hour, 2 hours, 3 hours, 5 hours, 8 hours, 12 hours, 16 hours, 24 hours, 36 hours, 48 hours, 3 days, 5 days, 7 days, 10 days, 15 days, 30 days, 60 days, 90 days, 120 days, 150 days, or more than 150 days after cooling is discontinued.

Also provided herein in certain embodiments are devices and systems for carrying out the disclosed methods. In certain embodiments, the methods provided herein utilize a treatment unit that is applied proximal to a target site on a subject's skin. Provided herein in certain embodiments are devices and systems comprising such a treatment unit, such as those described in greater detail with respect to FIG. 19.

In certain embodiments of the methods disclosed herein, the absence of significant destruction of subcutaneous lipid-rich cells following epidermal cooling may be a result of the subcutaneous layer not being cooled to a low enough temperature for a long enough period of time to trigger significant fat cell destruction. This may be a result of using a higher temperature for epidermal cooling than would normally be used for cryolipolysis procedures, a shorter duration of cooling than would normally be used for cryolipolysis procedures, or a combination thereof.

In certain embodiments of the methods disclosed herein, the absence of significant destruction of subcutaneous lipid-rich cells following epidermal cooling is a result of the subcutaneous layer not being cooled for a sufficient period of time to trigger fat cell destruction. In these embodiments, the subcutaneous layer may be cooled to a temperature that would result in significant destruction of subcutaneous lipid-rich cells over a long enough duration, but with cooling discontinued before said significant destruction occurs.

In certain embodiments of the methods, systems, and devices provided herein, epidermal cooling is performed by applying a treatment unit proximal to the epidermis at a target site, wherein the treatment unit does not cool the underlying tissue to a depth necessary for cryolipolysis but does so to achieve controlled sub-cryolipolytic cooling.

In certain embodiments of the methods, systems, and devices provided herein, epidermal cooling performed by applying a treatment unit proximal to the epidermis at a target site, wherein the treatment unit is set at a temperature that is insufficiently low to produce significant subcutaneous lipid-rich cell destruction. In these embodiments, the temperature of the treatment unit is higher than a temperature that would be used for cryolipolytic procedures. Because of this relatively higher temperature, application of the treatment unit does not lower the temperature of the subcutaneous layer to a degree that would result in significant subcutaneous lipid-rich cell destruction.

As described in detail above, epidermal cooling (e.g., controlled cooling) is performed by applying a treatment unit proximal to the epidermis at a target site for a period of time that is insufficient to produce significant subcutaneous lipid-rich cell destruction. In these embodiments, the period of time that the treatment unit is proximal to the epidermis is shorter than a period of time that would be used for cryolipolysis. In certain embodiments, this relatively shorter exposure time means that the treatment unit does not lower the temperature of the subcutaneous layer to a degree that results in significant subcutaneous lipid-rich cell destruction. In other embodiments, this relatively shorter exposure time means that the treatment unit lowers the temperature of the subcutaneous layer to a degree that could result in significant subcutaneous lipid-rich cell destruction, but does so for a period too short to produce said destruction. In certain embodiments, the treatment unit may be applied proximal to the epidermis for a period of time that is (e.g., ½, ¼, ⅛, or ⅒ the time that would be used for cryolipolysis).

As described in detail above, in certain embodiments of the methods, systems, and devices provided herein where the treatment unit is applied proximal to the epidermis for a period of time insufficient to produce significant subcutaneous lipid-rich cell destruction, the treatment unit is set at or near a temperature that may be used for cryolipolysis. In other embodiments, the treatment unit is set at a temperature higher than a temperature that may be used for cryolipolysis (i.e., cooling is performed at both a higher temperature and for a shorter time period than would be used for cryolipolysis).

In certain embodiments of the methods, systems, and devices provided herein, multiple (i.e., two or more) cooling cycles may be utilized over the course of a single treatment session, with successive cooling cycles separated by non-cooling cycles, and preferably cycles of active re-warming. For example, in certain embodiments, a treatment unit may be applied proximal to the epidermis at a target site for a first cooling cycle, removed for a first non-cooling cycle, and then re-applied for a second cooling cycle. This process may be repeated for as many cycles as necessary to achieve a desired result. Alternatively, the treatment unit can remain applied proximal to the epidermis at the target site for all the cooling and warming/re-warming cycles, with the treatment unit having a cooling/heating element that can be precisely controlled. For example, a thermoelectric cooler could be used to cool, and then to re-warm, by simply reversing a voltage across the thermoelectric cooler. In certain embodiments, the non-cooling cycles may be a predetermined time period. In other embodiments, the non-cooling cycles may be variable. For example, in certain embodiments, the non-cooling cycle may be a time period sufficient for the temperature of the subcutaneous layer, dermal layer, or epidermis to increase back to a target temperature (e.g., back to a pre-treatment baseline temperature). In certain embodiments, the non-cooling cycles may utilize passive warming (i.e., the skin is allowed to naturally warm back to a baseline or other predetermined temperature without any intervention). In other embodiments, the non-cooling cycles may utilize activate warming to bring the epidermal temperature back to a baseline or other predetermined temperature.

In certain embodiments of the methods, systems, and devices provided herein, multiple (i.e., two or more) treatment sessions may be performed. For example, treatment sessions may be repeated as necessary to achieve or maintain a desired result. In certain embodiments, treatment sessions may be repeated at predetermined intervals (e.g., about every 2 days, about every 5 days, about every week, about every month, about every 2, 3, or 4 months) for a fixed period of time. Alternatively, treatment sessions may be repeated on an as-needed basis.

In some embodiments of the methods, systems, and devices provided herein, a temperature can be ramped from a first temperature, to a second temperature, to a third temperature, to a fourth temperature, and so on, during application of the epidermal cooling treatment to the target site. The temperature can be ramped-up (e.g., the first temperature is lower than the second temperature, which is lower than the third temperature, which is lower than the fourth temperature, and so on) or the temperature can be ramped-down (e.g., the first temperature is greater than the second temperature, which is greater than the third temperature, which is greater than the fourth temperature, and so on). In these embodiments, the temperature can be ramped over a portion of the treatment duration or across the entire treatment.

In certain embodiments of the methods disclosed herein, epidermal cooling does not significantly lower the temperature of the subcutaneous fat layer beneath a target site. In other embodiments, epidermal cooling may lower the temperature of the underlying subcutaneous fat layer, but only to a certain depth as described above. For example, in certain embodiments, the epidermal cooling does not significantly decrease the temperature of subcutaneous tissue at or below about 1 mm, about 2 mm, about 3 mm, about 4 mm, about 5 mm, 6 mm, 7 mm, about 9 mm, about 14 mm, about 18 mm, or about 20 mm below the subject's dermal layer. In one embodiment, the epidermal cooling may decrease the temperature of the underlying subcutaneous fat layer at about 5 mm to about 7 mm below the skin surface from a pre-treatment baseline temperature, while the underlying subcutaneous fat layer at about 7 mm or deeper is not cooled sufficiently from baseline. In these embodiments, the degree of cooling and/or the duration of cooling of the subcutaneous fat layer below about 5 mm to about 7 mm is insufficient to produce significant destruction of subcutaneous lipid-rich cells in these deeper layers. As described above, methods of the present disclosure include cooling the surface of the target area to about −40° C. to about 10° C. for about 5 minutes to about 2 hours by placing the treatment unit on the target site and applying sub-cryolipolytic cooling. In some embodiments, the target temperature is within a temperature range of about −15° C. to about 0° C. and the cooling is applied for about 10 minutes to about 25 minutes. In other embodiments, the target temperature is within a temperature range of about −40° C. to about 0° C. and the cooling is applied for about 10 seconds to about 25 minutes. In certain embodiments, a significant decrease in the temperature of subcutaneous tissue refers to a decrease of about 1° C. or more from a baseline temperature. The baseline temperature may be determined for an individual subject before the application of controlled cooling. Accordingly, in certain embodiments, the methods provided herein comprise a step of determining a baseline temperature of subcutaneous tissue at one or more specified depths.

In certain embodiments, sub-cryolipolytic controlled cooling maintains the temperature of subcutaneous tissue located at least about 5 mm to about 10 mm below the skin surface at or above a predetermined minimum temperature. For example, sub-cryolipolytic controlled cooling may maintain the temperature of subcutaneous tissue located at least about 5 mm to about 10 mm below the skin surface at or above a predetermined minimum temperature of about 20° C., about 15° C., about 10° C., about 5° C., about 4° C., about 3° C., about 2° C., about 1° C., about 0° C., or about −5° C.

In certain embodiments of the methods, systems, and devices provided herein, controlled sub-cryolipolytic cooling cools the epidermal and/or dermal layer to a lesser degree than would be associated with cryolipolytic fat removal.

Controlled sub-cryolipolytic cooling is expected to reduce the risk of adverse effects associated with cryolipolytic fat removal. For example, due to the higher temperatures and/or shorter exposure times, controlled sub-cryolipolytic cooling is expected to reduce the risk of epidermal damage, including hypo- or hyper-pigmentation.

In certain embodiments, a treatment unit for use in the methods, systems, and devices provided herein is the same as or similar to a treatment unit that would be used for cryolipolytic fat removal. In these embodiments, the treatment unit is capable of cooling the subcutaneous fat layer to a degree that would result in fat removal, but it is not used in this manner. For example, the treatment unit may be set at a higher temperature (i.e., cooled to a lesser degree) than would be used for fat removal, or it may be applied for shorter time periods or for fewer cooling cycles. An advantage of such treatment units is that they can be used for either cryolipolytic fat removal or for the sub-cryolipolytic methods provided herein.

In certain embodiments, a treatment unit for use in the methods, systems, and devices provided herein is different than a treatment unit that would be used for cryolipolytic fat removal. In certain of these embodiments, the treatment unit may be incapable of cooling the subcutaneous layer to the degree required for cryolipolytic fat removal. For example, the treatment unit may be designed such that it cannot be cooled to a degree necessary to significantly cool the subcutaneous layer. Alternatively, the treatment unit may incorporate a feedback mechanism whereby its temperature is increased when a target level of dermal cooling is reached, or when the subcutaneous layer begins to exhibit cooling. An advantage of such treatment units is that they reduce the risk of inadvertent over-cooling of the subcutaneous layer, and therefore may reduce the risk of one or more adverse events associated with low temperature cooling (e.g., hyperpigmentation, hypopigmentation, unwanted blistering, unwanted scarring, permanent undesirable alterations, skin freeze, loss of sensation (e.g., permanent and/or temporary) and disfiguring scars). In certain embodiments, the treatment methods, systems, and devices disclosed herein cause edema. In other embodiments, the treatment methods, systems, and devices disclosed herein induce a therapeutic amount of edema (e.g., an amount of edema which contributes to one or more desirable and/or beneficial effects on the subject). However, in some embodiments, the treatment methods, systems, and devices disclosed herein may cause transient local redness, bruising, and/or numbness.

In other embodiments, the treatment methods, systems, and devices disclosed herein can promote wound healing as intradermal adipocytes are known to mediate fibroblast recruitment during skin wound healing (Schmidt, B. A., Horsley, V. Intradermal adipocytes mediate fibroblast recruitment during skin wound healing (2013) Development (Cambridge), 140 (7), pp. 1517-1527). Without intending to be bound by any particular theory, restoration of the extracellular matrix associated with the subject's skin is expected to induce, promote, improve, or otherwise mediate wound healing at, within, or in tissue surrounding or otherwise associated with the subject's skin.

In addition to increased collagen production, the controlled non-cryolipolytic cooling methods provided herein may increase one or more additional components of the skin extracellular matrix, including, for example, one or more of elastin fibers, glycoproteins, and protein-polysaccharides. In those embodiments wherein the methods provided herein promote elastin formation, breakdown, and de novo synthesis (remodeling) and/or restoration of native elastin, these changes may be mediated by upregulation of tropoelastin expression in or near treated fat tissue.

Without being bound by any hypothesis, the observed changes in collagen production and skin thickness following controlled sub-cryolipolytic cooling may be a result of injured or stimulated cells (e.g., preadipocytes, adipocytes, local fibroblasts, inflammatory cells, stem cells) in subcutaneous fat releasing cytokines/growth factors (e.g., TGF-β, PDGF, bFGF, IGF), which in turn stimulate neighboring connective tissue cells in the dermal fat and skin (e.g., fibroblasts, myofibroblasts) to synthesize extracellular matrix components (e.g., collagen, elastin).

For example, TGF-β is known to be a key mediator of the expression of several connective tissue genes. TGF-β signaling is induced by ligand binding to its cognate cell membrane receptors, which are serine/threonine protein kinases. The cell membrane receptors are classed as type I or II receptors (TGFβRI and TGFβRII). The type II receptors are constitutively active. Upon ligand binding, they are brought into close proximity to type I receptors to phosphorylate and activate them. In the canonical signaling, receptor activation induces the C-terminal phosphorylation of a group of transcription factors (TFs) known as SMADs. The phosphorylated SMADs then form a complex with a co-mediator SMAD, SMAD4, that is translocated to the nucleus where it binds to gene promoters. In co-operation with different TFs and co-factors, these complexes control the transcription of hundreds of genes. By this, or other similar pathways, upon tissue controlled sub-cryolipolytic cooling and release of TGF-β, nearby fibroblasts and/or other reparative cells can proliferate and synthetize extracellular matrix components. Evidence of the regulation of collagen and elastin synthesis by skin cells in the presence of TGF-β has been studied widely [1-10].

One of ordinary skill in the art will recognize that the various embodiments described herein can be combined. For example, steps from the various methods of treatment disclosed herein may be combined in order to achieve a satisfactory or improved level of treatment.

The term "about" as used herein means within 10% of a stated value or range of values.

Figure 15:
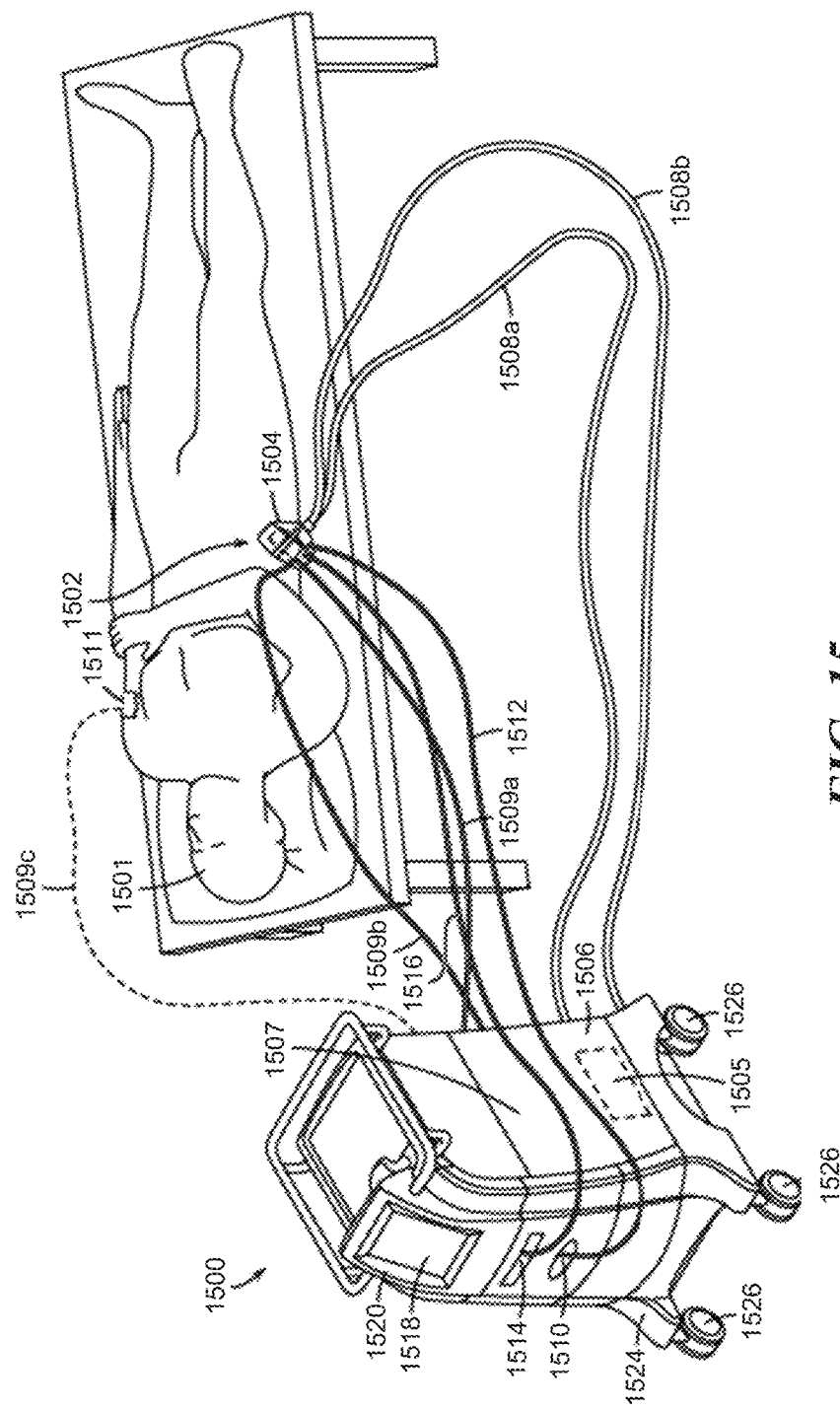
FIG. 15 is a partially schematic, isometric view of a treatment system for non-invasively removing heat from subcutaneous lipid-rich target areas of a subject in accordance with an embodiment of the technology.

Referring to FIG. 15, the illustration is a partially schematic, isometric view showing one example of the treatment system 1500 for non-invasively removing heat from subcutaneous lipid-rich target areas of the patient or subject 1501, such as an abdominal area 1502 or another suitable area. The applicator 1504 can engage the target area of the subject 1501 and a treatment unit 1506 that operate together to cool or otherwise remove heat from the subcutaneous lipid-rich cells of the subject 1501. The applicator 1504 can be part of an application system, and the applicator 1504 can have various configurations, shapes, and sizes suitable for different body parts such that heat can be removed from any cutaneous or subcutaneous lipid-rich target area of the subject 1501. For example, various types of applicators may be applied during treatment, such as a vacuum applicator, a belt applicator (either of which may be used in combination with a massage or vibrating capability), and so forth. Each applicator 1504 may be designed to treat identified portions of the patient's body, such as chin, cheeks, arms, pectoral areas, thighs, calves, buttocks, abdomen, "love handles", back, breast, and so forth. For example, the vacuum applicator may be applied at the back region, and the belt applicator can be applied around the thigh region, either with or without massage or vibration. Exemplary applicators and their configurations usable or adaptable for use with the treatment system 100 variously are described in (e.g., commonly assigned U.S. Pat. No. 7,854,754 and U.S. Patent Publication Nos. 2008/0077201, 2008/0077211 and 2008/0287839, incorporated herein by reference in their entirety). In further embodiments, the system 1500 may also include a patient protection device (not shown) incorporated into or configured for use with the applicator 1504 that prevents the applicator from directly contacting a patient's skin and thereby reducing the likelihood of cross-contamination between patients, minimizing cleaning requirements for the applicator. The patient protection device may also include or incorporate various storage, computing, and communications devices, such as a radio frequency identification (RFID) component, allowing, for example, use to be monitored and/or metered. Exemplary patient protection devices are described in commonly assigned U.S. Patent Publication No. 2008/0077201 incorporated herein by reference in its entirety.

In the present example, the system 1500 can also include the treatment unit 1506 and supply and return fluid lines 1508*a-b* between the applicator 1504 and the treatment unit 1506. A treatment unit 1506 is a device that can increase or decrease the temperature at a connected applicator 1504 that is configured to engage the subject and/or the target region of the subject. The treatment unit 1506 can remove heat from a circulating coolant to a heat sink and provide a chilled coolant to the applicator 1504 via the fluid lines 1508*a-b*. Alternatively, the treatment unit 1506 can circulate warm coolant to the applicator 1504 during periods of warming. In further embodiments, the treatment unit 1506 can circulate coolant through the applicator 1504 and increase or decrease the temperature of the applicator by controlling power delivery to one or more Peltier-type thermoelectric elements incorporated within the applicator. Examples of the circulating coolant include water, glycol, synthetic heat transfer fluid, oil, a refrigerant, and/or any other suitable heat conducting fluid. The fluid lines 1508*a-b* can be hoses or other conduits constructed from polyethylene, polyvinyl chloride, polyurethane, and/or other materials that can accommodate the particular circulating coolant. The treatment unit 1506 can be a refrigeration unit, a cooling tower, a thermoelectric chiller, or any other device capable of removing heat from a coolant. In one embodiment, the treatment unit 1506 can include a fluid chamber 1505 configured to house and provide the coolant. Alternatively, a municipal water supply (e.g., tap water) can be used in place of or in conjunction with the treatment unit 1506. In a further embodiment, the applicator 1504 can be a fluid-cooled applicator capable of achieving a desired temperature profile such as those described in U.S. patent application Ser. No. 13/830,027, incorporated herein by reference in its entirety. One skilled in the art will recognize that there are a number of other cooling technologies that could be used such that the treatment unit, chiller, and/or applicator need not be limited to those described herein.

The system 1500 can optionally include an energy-generating unit 1507 for applying energy to the target region, for example, to further interrogate cooled lipid-rich cells in cutaneous or subcutaneous layers via power lines 1509*a-b* between the applicator 1504 and the energy-generating unit 1507. In one embodiment, the energy-generating unit 1507 can be an electroporation pulse generator, such as a high voltage or low voltage pulse generator, capable of generating and delivering a high or low voltage current, respectively, through the power lines 1509*a*, 1509*b* to one or more electrodes (e.g., cathode, anode) in the applicator 1504. In other embodiments, the energy-generating unit 1507 can include a variable powered RF generator capable of generating and delivering RF energy, such as RF pulses, through the power lines 1509*a*, 1509*b* or to other power lines (not shown). In a further embodiment, the energy-generating unit 1507 can include a microwave pulse generator, an ultrasound pulse laser generator, or high frequency ultrasound (HIFU) phased signal generator, or other energy generator suitable for applying energy, for example, to further interrogate cooled lipid-rich cells in cutaneous or subcutaneous layers. In some embodiments (e.g., RF return electrode, voltage return when using a monopolar configuration, etc.), the system 1500 can include a return electrode 1511 located separately from the applicator 1504; power line 1509*c* (shown in dotted line) can electrically connect the return electrode 1511, if present, and the energy-generating unit 1507. In additional embodiments, the system 1500 can include more than one energy generator unit 1507 such as any one of a combination of the energy modality generating units described herein. Systems having energy-generating units and applicators having one or more electrodes are described in commonly assigned U.S. Patent Publication No. 2012/0022518 and U.S. patent application Ser. No. 13/830,413.

In the illustrated example, the applicator 1504 is associated with at least one treatment unit 1506. The applicator 1504 can provide mechanical energy to create a vibratory, massage, and/or pulsatile effect. The applicator 1504 can include one or more actuators, such as motors with eccentric weight, or other vibratory motors such as hydraulic motors, electric motors, pneumatic motors, solenoids, other mechanical motors, piezoelectric shakers, and so on, to provide vibratory energy or other mechanical energy to the treatment site. Further examples include a plurality of actuators for use in connection with a single applicator 1504 in any desired combination. For example, an eccentric weight actuator can be associated with one section of an applicator 1504, while a pneumatic motor can be associated with another section of the same applicator 1504. This, for example, would give the operator of the treatment system 1500 options for differential treatment of lipid-rich cells within a single region or among multiple regions of the subject 1501. The use of one or more actuators and actuator types in various combinations and configurations with an applicator 1501 may be possible.

The applicator 1504 can include one or more heat-exchanging units. Each heat-exchanging unit can include or be associated with one or more Peltier-type thermoelectric elements, and the applicator 104 can have multiple individually controlled heat-exchanging zones (e.g., between 1 and 50, between 10 and 45, between 15 and 21, approximately 100, etc.) to create a custom spatial cooling profile and/or a time-varying cooling profile. Each custom treatment profile can include one or more segments, and each segment can include a specified duration, a target temperature, and control parameters for features such as vibration, massage, vacuum, and other treatment modes. Applicators having multiple individually controlled heat-exchanging units are described in commonly assigned U.S. Patent Publication Nos. 2008/0077211 and 2011/0238051, incorporated herein by reference in their entirety.

The system 1500 can further include a power supply 1510 and a controller 1514 operatively coupled to the applicator 1504. In one embodiment, the power supply 1510 can provide a direct current voltage to the applicator 1504 to remove heat from the subject 1501. The controller 1514 can monitor process parameters via sensors (not shown) placed proximate to the applicator 1504 via a control line 1516 to, among other things, adjust the heat removal rate and/or energy delivery rate based on the process parameters. The controller 1514 can further monitor process parameters to adjust the applicator 1514 based on treatment parameters, such as treatment parameters defined in a custom treatment profile or patient-specific treatment plan, such as those described, for example, in commonly assigned U.S. Pat. No. 8,275,442, incorporated herein by reference in its entirety.

The controller 1514 can exchange data with the applicator 1504 via an electrical line 1512 or, alternatively, via a wireless or an optical communication link. Note that control line 1516 and electrical line 1512 are shown in FIG. 15 without any support structure. Alternatively, control line 1516 and electrical line 1512 (and other lines including, but not limited to, fluid lines 108*a*-*b* and power lines 1509*a*-*b*) may be bundled into or otherwise accompanied by a conduit or the like to protect such lines, enhance ergonomic comfort, minimize unwanted motion (and thus potential inefficient removal of heat from and/or delivery of energy to subject 1501), and to provide an aesthetic appearance to the system 1500. Examples of such a conduit include a flexible polymeric, fabric, or composite sheath, an adjustable arm, etc. Such a conduit (not shown) may be designed (via adjustable joints, etc.) to "set" the conduit in place for the treatment of the subject 1501.

The controller 1514 can include any processor, Programmable Logic Controller, Distributed Control System, secure processor, and the like. A secure processor can be implemented as an integrated circuit with access-controlled physical interfaces; tamper resistant containment; means of detecting and responding to physical tampering; secure storage; and shielded execution of computer-executable instructions. Some secure processors also provide cryptographic accelerator circuitry. Secure storage may also be implemented as a secure flash memory, secure serial EEPROM, secure field programmable gate array, or secure application-specific integrated circuit.

In another aspect, the controller 1514 can receive data from an input device 1518 (shown as a touch screen), transmit data to an output device 1520 (not shown), and/or exchange data with a control panel (not shown). The input device 1518 can include a keyboard, a mouse, a stylus, a touch screen, a push button, a switch, a potentiometer, a scanner, an audio component such as a microphone, or any other device suitable for accepting user input. The output device 1520 can include a display or touch screen, a printer, a video monitor, a medium reader, an audio device such as a speaker, any combination thereof, and any other device or devices suitable for providing user feedback.

In the embodiment of FIG. 15, the output device 1520 is a touch screen that functions as both an input device 1518 and an output device 1520. The control panel can include visual indicator devices or controls (e.g., indicator lights, numerical displays, etc.) and/or audio indicator devices or controls. The control panel may be a component separate from the input device 1518 and/or output device 1520, may be integrated with one or more of the devices, may be partially integrated with one or more of the devices, may be in another location, and so on. In alternative examples, the control panel, input device 1518, output device 1520, or parts thereof (described herein) may be contained in, attached to, or integrated with the applicator 1504. In this example, the controller 1514, power supply 1510, control panel, treatment unit 1506, input device 1518, and output device 1520 are carried by a rack 1524 with wheels 1526 for portability. In alternative embodiments, the controller 1514 can be contained in, attached to, or integrated with the multi-modality applicator 1504 and/or the patient protection device described above. In yet other embodiments, the various components can be fixedly installed at a treatment site. Further details with respect to components and/or operation of applicators 1504, treatment units 1506, and other components may be found in commonly assigned U.S. Patent Publication No. 2008/0287839.

In operation, and upon receiving input to start a treatment protocol, the controller 1514 can cause one or more power supplies 1510, one or more treatment units 1506, and one or more applicators 1504 to cycle through each segment of a prescribed treatment plan. In so doing, power supply 1510 and treatment unit 1506 provide coolant and power to one or more functional components of the applicator 1504, such as thermoelectric coolers (e.g., TEC "zones"), to begin a cooling cycle and, for example, activate features or modes such as vibration, massage, vacuum, etc.

Using temperature sensors (not shown) proximate to the one or more applicators 1504, the patient's skin, a patient protection device, or other locations or combinations thereof, the controller 1514 can determine whether a temperature or heat flux is sufficiently close to the target temperature or heat flux. It will be appreciated that while a region of the body (e.g., adipose tissue) has been cooled or heated to the target temperature, in actuality that region of the body may be close but not equal to the target temperature, e.g., because of the body's natural heating and cooling variations. Thus, although the system may attempt to heat or cool the tissue to the target temperature or to provide a target heat flux, a sensor may measure a sufficiently close temperature or heat flux. If the target temperature has not been reached, power can be increased or decreased to change heat flux to maintain the target temperature or "set-point" selectively to affect lipid-rich subcutaneous adipose tissue.

When the prescribed segment duration expires, the controller 1514 may apply the temperature and duration indicated in the next treatment profile segment. In some embodiments, temperature can be controlled using a variable other than or in addition to power.

In some embodiments, heat flux measurements can indicate other changes or anomalies that can occur during treatment administration. For example, an increase in temperature detected by a heat flux sensor can indicate a freezing event at the skin or underlying tissue (i.e., dermal tissue). An increase in temperature as detected by the heat flux sensors can also indicate movement associated with the applicator, causing the applicator to contact a warmer area of the skin, for example. Methods and systems for collection of feedback data and monitoring of temperature measurements are described in commonly assigned U.S. Pat. No. 8,285,390.

The applicators 1504 may also include additional sensors to detect process treatment feedback. Additional sensors may be included for measuring tissue impedance, treatment application force, tissue contact with the applicator and energy interaction with the skin of the subject 1501 among other process parameters.

In one embodiment, feedback data associated that heat removal from lipid-rich cells in the cutaneous or subcutaneous layer can be collected in real-time. Real-time collection and processing of such feedback data can be used in concert with treatment administration to ensure that the process parameters used to alter or reduce subcutaneous adipose tissue are administered correctly and efficaciously.

Examples of the system 1500 may provide the applicator 1504, which damages, injures, disrupts, or otherwise reduces lipid-rich cells generally without collateral damage to non-lipid-rich cells in the treatment region. In general, it is believed that lipid-rich cells selectively can be affected (e.g., damaged, injured, or disrupted) by exposing such cells to low temperatures that do not so affect non-lipid-rich cells. Moreover, as discussed above, a cryoprotectant can be administered topically to the skin of the subject 1501 at the treatment site and/or used with the applicator 1504 to, among other advantages, assist in preventing freezing of the non-lipid-rich tissue (e.g., in the dermal and epidermal skin layers) during treatment to selectively interrogate lipid-rich cells in the treatment region so as to beneficially and cosmetically alter subcutaneous adipose tissue, treat sweat glands, and/or reduce sebum secretion. As a result, lipid-rich cells, such as subcutaneous adipose tissue and glandular epithelial cells, can be damaged while other non-lipid-rich cells (e.g., dermal and epidermal skin cells) in the same region are generally not damaged, even though the non-lipid-rich cells at the surface may be subject to even lower temperatures. In some embodiments, the mechanical energy provided by the applicator 104 may further enhance the effect on lipid-rich cells by mechanically disrupting the affected lipid-rich cells. In one mode of operation, the applicator 1504 may be configured to be a handheld device such as the device disclosed in commonly assigned U.S. Pat. No. 7,854,754, incorporated herein by reference in its entirety.

Applying the applicator 1504 with pressure or with a vacuum type force to the subject's skin or pressing against the skin can be advantageous to achieve efficient treatment. In general, the subject 1501 has an internal body temperature of about 37° C., and the blood circulation is one mechanism for maintaining a constant body temperature. As a result, blood flow through the skin and subcutaneous layer of the region to be treated can be viewed as a heat source that counteracts the cooling of the subdermal fat. As such, cooling the tissue of interest requires not only removing the heat from such tissue but also that of the blood circulating through this tissue. Thus, temporarily reducing or eliminating blood flow through the treatment region, by means such as, e.g., applying the applicator with pressure, can improve the efficiency of tissue cooling and avoid excessive heat loss through the dermis and epidermis. Additionally, a vacuum can pull skin away from the body which can assist in cooling targeted underlying tissue.

The system 1500 (FIG. 15) can be used to perform several pre-treatment and treatment methods. Although specific examples of methods are described herein, one skilled in the art is capable of identifying other methods that the system could perform. Moreover, the methods described herein can be altered in various ways. As examples, the order of illustrated logic may be rearranged, sub-stages may be performed in parallel, illustrated logic may be omitted, other logic may be included, etc.

Figure 16:
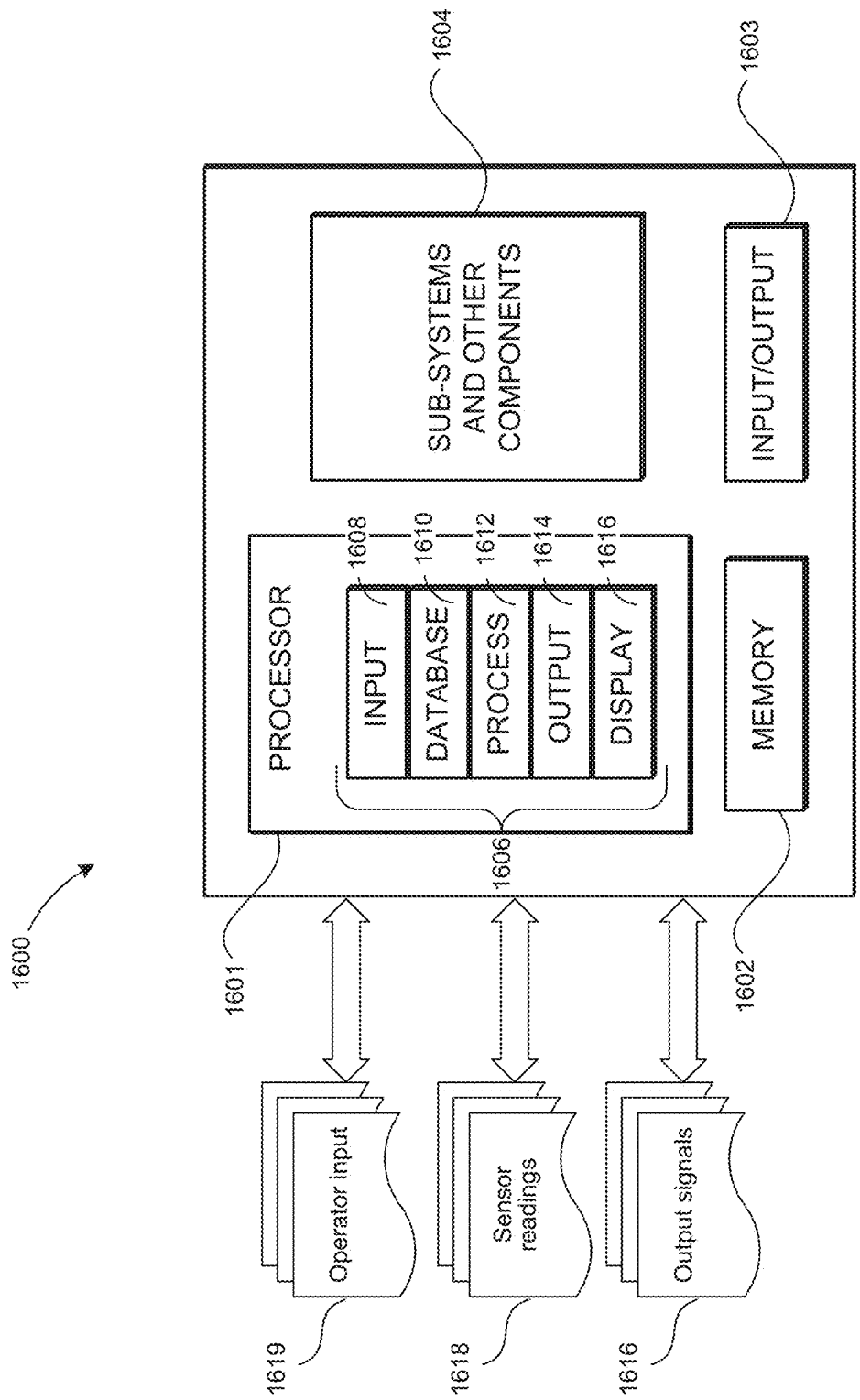
FIG. 16 is a schematic block diagram illustrating computing system software modules and subcomponents of a computing device suitable to be used in the system of FIG. 15 in accordance with an embodiment of the technology.

FIG. 16 is a schematic block diagram illustrating sub-components of a computing device 1600 in accordance with an embodiment of the disclosure. The computing device 1600 can include a processor 1601, a memory 1602 (e.g., SRAM, DRAM, flash, or other memory devices), input/output devices 1603, and/or subsystems and other components 1604. The computing device 1600 can perform any of a wide variety of computing processing, storage, sensing, imaging, and/or other functions. Components of the computing device 1600 may be housed in a single unit or distributed over multiple, interconnected units (e.g., through a communications network). The components of the computing device 1600 can accordingly include local and/or remote memory storage devices and any of a wide variety of computer-readable media.

As illustrated in FIG. 16, the processor 1601 can include a plurality of functional modules 1606, such as software modules, for execution by the processor 1601. The various implementations of source code (i.e., in a conventional programming language) can be stored on a computer-readable storage medium or can be embodied on a transmission medium in a carrier wave. The modules 1606 of the processor can include an input module 808, a database module 1610, a process module 1612, an output module 1614, and, optionally, a display module 1616.

In operation, the input module 1608 accepts an operator input 1619 via the one or more input devices described above with respect to FIG. 15, and communicates the accepted information or selections to other components for further processing. The database module 1610 organizes records, including patient records, treatment data sets, treatment profiles and operating records and other operator activities, and facilitates storing and retrieving of these records to and from a data storage device (e.g., internal memory 1602, an external database, etc.). Any type of database organization can be utilized, including a flat file system, hierarchical database, relational database, distributed database, etc.

In the illustrated example, the process module 1612 can generate control variables based on sensor readings 1618 from sensors (e.g., temperature measurement components) and/or other data sources, and the output module 1614 can communicate operator input to external computing devices and control variables to the controller 1914 (FIG. 15). The display module 1616 can be configured to convert and transmit processing parameters, sensor readings 1618, output signals 1618, input data, treatment profiles and pre-scribed operational parameters through one or more connected display devices, such as a display screen, printer, speaker system, etc. A suitable display module 1616 may include a video driver that enables the controller 1614 to display the sensor readings 1618 or other status of treatment progression on the output device 1620 (FIG. 15).

In various embodiments, the processor 1601 can be a standard central processing unit or a secure processor. Secure processors can be special-purpose processors (e.g., reduced instruction set processor) that can withstand sophisticated attacks that attempt to extract data or programming logic. The secure processors may not have debugging pins that enable an external debugger to monitor the secure processor's execution or registers. In other embodiments, the system may employ a secure field programmable gate array, a smartcard, or other secure devices.

The memory 1602 can be standard memory, secure memory, or a combination of both memory types. By employing a secure processor and/or secure memory, the system can ensure that data and instructions are both highly secure and sensitive operations such as decryption are shielded from observation.

Suitable computing environments and other computing devices and user interfaces are described in commonly assigned U.S. Pat. No. 8,275,442, entitled "TREATMENT PLANNING SYSTEMS AND METHODS FOR BODY CONTOURING APPLICATIONS," which is incorporated herein in its entirety by reference.

EXAMPLES

Example 1: Effect of Controlled Cryolipolytic Cooling on TGF-β Expression

A commercially available CoolAdvantage Petite™ treatment unit, available from Zeltiq Aesthetics, Inc., the assignee of the invention, was set to controlled cooling temperature of −11° C. and was applied proximal to a target site on human subject's skin for a treatment duration of 35 minutes.

The effect of epidermal cooling on TGF-β mRNA expression in skin and fat layers was evaluated by RNA in situ hybridization (RNA-ISH) staining of formalin-fixed paraffin-embedded (FFPE) tissue samples using the Invitrogen viewRNA™ ISH assay protocol. The probe was human TGF-β1 gene (Thermofisher, # VA6-17264).

Figures 1C, 1D:
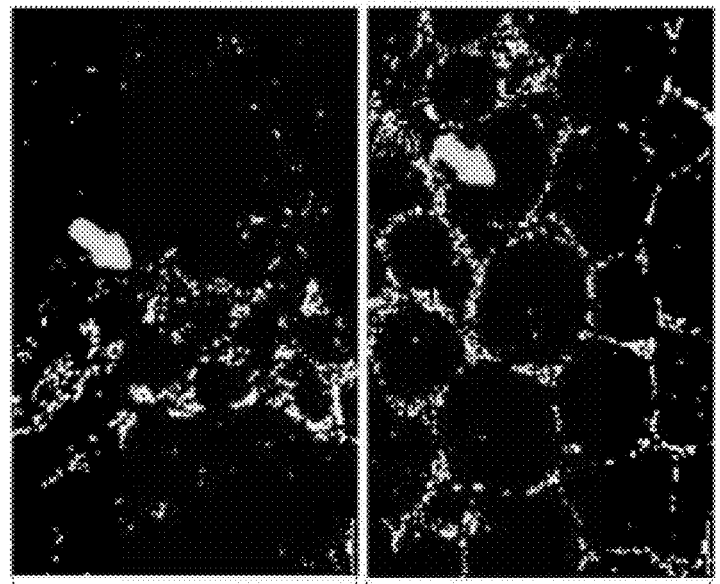
Figure 1B:
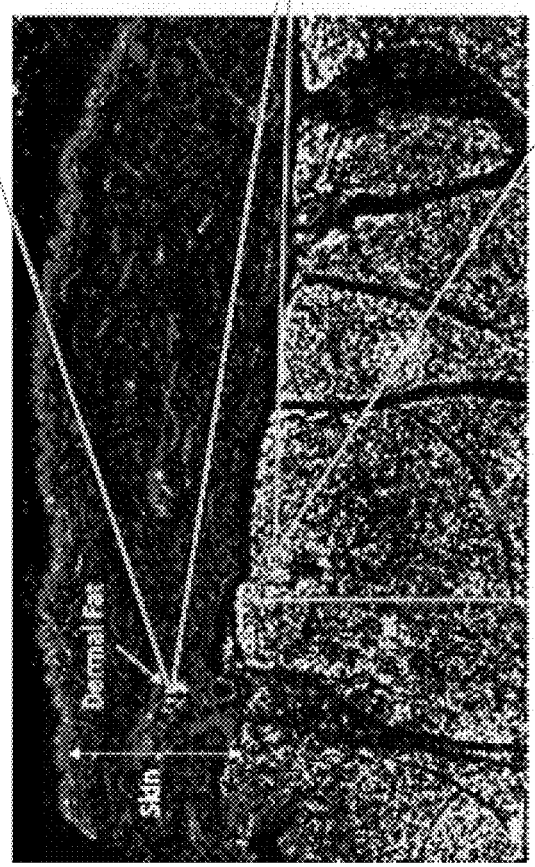

Three weeks after treatment, subjects exhibited a significant increase in TGF-β mRNA expression in fat (FIGS. 1B-1D), with little or no change in skin TGF-β mRNA levels. This increase was observed in both dermal and interfacial subcutaneous fat around adipocytes (FIGS. 1C and 1D), with higher expression in the subcutaneous layer (FIG. 1B). Untreated tissue (controls) showed no expression of TGF-β mRNA in either skin or subcutaneous fat (FIG. 1A).

Example 2: Effect of Controlled Cryolipolytic Cooling on Collagen Expression A CoolAdvantage Petite treatment unit set to −11° C. was applied proximal to a target site on human subjects' skin for 35 minutes.

The effect of epidermal cooling on collagen expression in skin and fat layers was evaluated by RNA-ISH staining of formalin-fixed paraffin-embedded (FFPE) tissue samples using the Invitrogen viewRNA™ ISH assay protocol. The probe was human COL1A1 (Thermofisher, # VA6-18298).

Figure 2A:
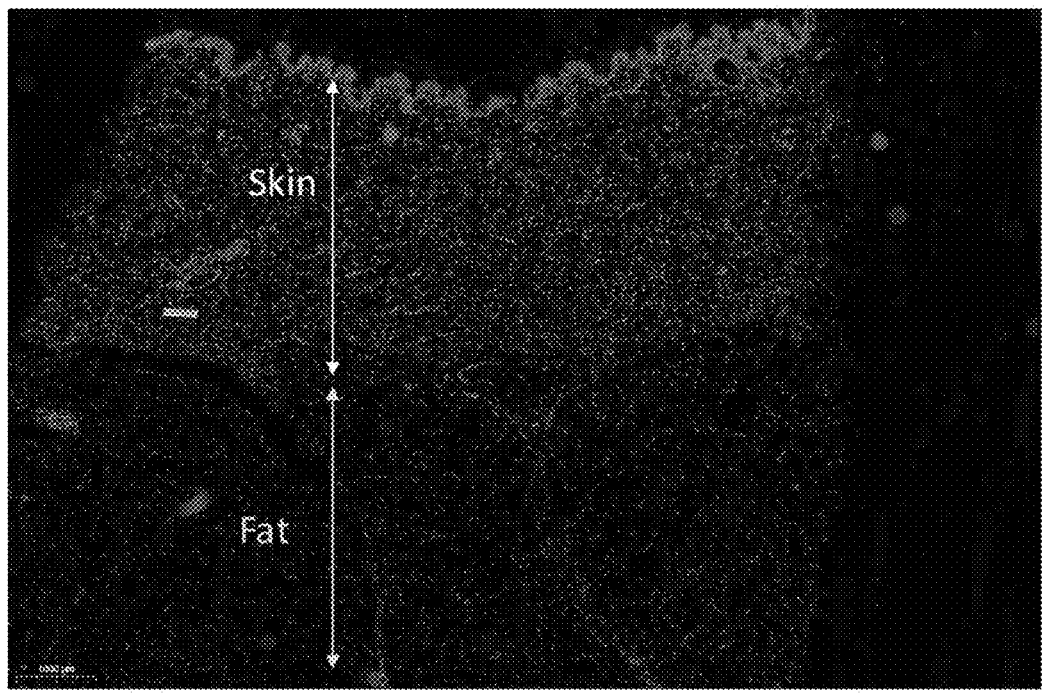
FIGS. 2A-2B: Representative tissue sections showing the effect of controlled epidermal cooling on collagen COL1A1 mRNA expression in skin and adipose tissue visualized by in situ hybridization. Fluorescence pseudocolor: COL1A1 mRNA=Cy5, red. Nucleus=TRITC, blue. 2A: Control (untreated tissue), showing positive signal for Cy5 only in skin and collagenous structures representing expression of COL1A1 mRNA. 2B: 3 weeks post-treatment sample showing an elevated signal of COL1A1 mRNA expression in subcutaneous adipose tissue.
Figure 2B:
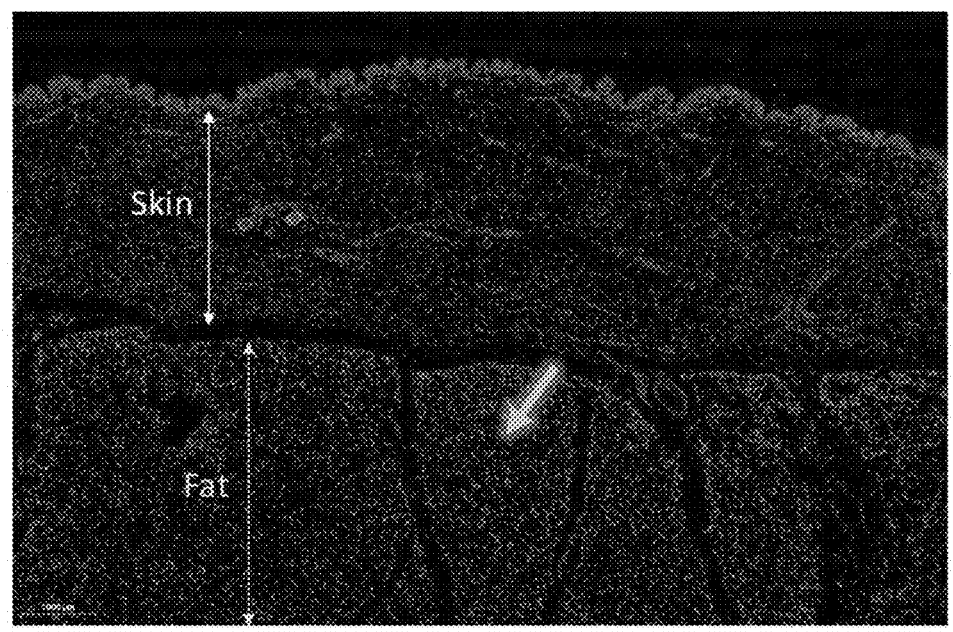

Three weeks after treatment subjects exhibited a significant increase in collagen, COL1A1 mRNA levels in subcutaneous fat tissue (compare FIGS. 2A (untreated) vs. 2B (treated)). Subcutaneous fat tissue of the untreated site showed no change or elevated signal of COL1A1 mRNA, FIG. 2A.

Figure 3A:
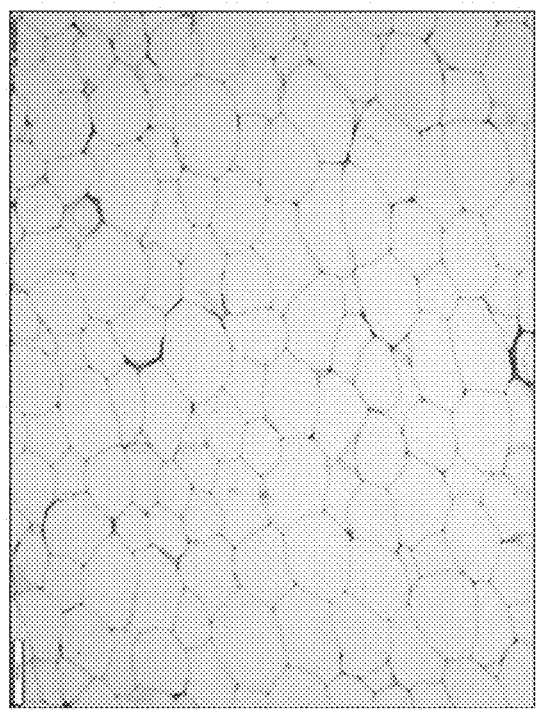
FIGS. 3A-3D: Representative adipose tissue sections showing collagen synthesis near adipocytes following controlled epidermal cooling. Collagen=Masson's Trichrome, blue. 3A: Control (untreated), showing no collagen staining around adipocytes. 3B: 1-week post-treatment, no collagen staining around adipocytes. 3C: 3 weeks post-treatment showing positive collagen staining (newly synthetized collagen) around adipocytes. 3D: Magnification of the 3 weeks post-treatment sample showing the newly synthetized collagen (arrows).
Figure 3B:
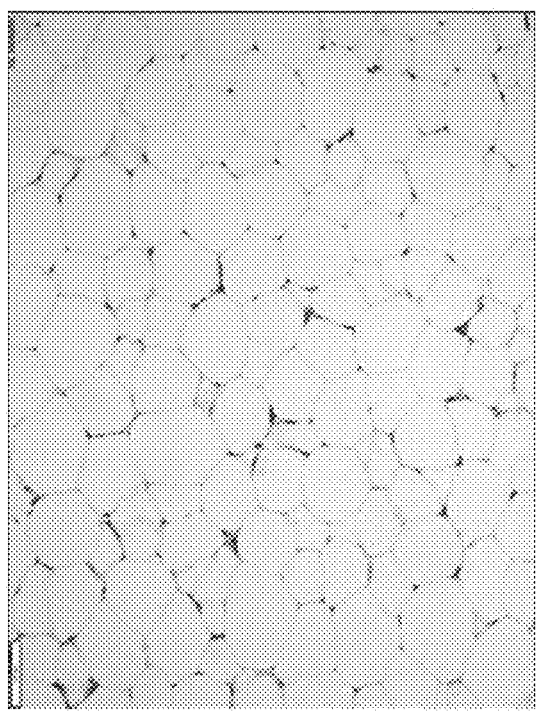
Figure 3C:
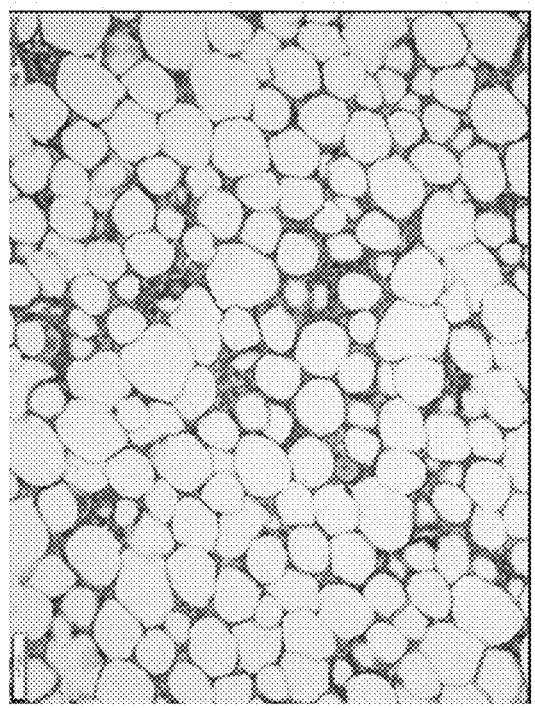
Figure 3D:
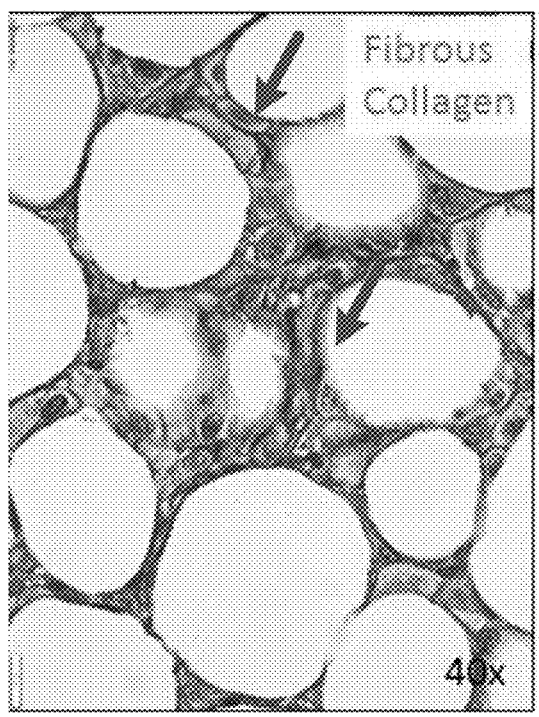

Upregulation of collagen mRNA is crucial for neocollagen synthesis (mRNA to protein central dogma). To ascertain whether collagen synthesis was indeed present due to mRNA upregulation following controlled sub-cryolipolytic cooling, tissue samples were stained with Masson's Trichrome (blue stain=collagen). A significant increase in fibrous collagen levels around treated adipocytes was observed following controlled sub-cryolipolytic cooling, compare FIGS. 3A (untreated) and 3B (1-week after treatment) vs. 3A (untreated) and 3C (three-weeks after treatment). A magnification of the collagen around treated adipocytes is shown in FIG. 3D. This evidence confirms the formation of neocollagen in the presence of COL1A1 and TGF-β mRNA following controlled sub-cryolipolytic cooling.

Example 3: Effect of Controlled Sub-Cryolipolytic Cooling on Skin Thickness

A shallow surface prototype applicator (designed to conform to the thigh curvature, available from Zeltiq Aesthetics, Inc) treatment unit set to −14° C. was applied proximal to a target site on 20 human subjects' skin for 20 minutes per treatment.

The effect of epidermal cooling on skin thickness was evaluated by measuring thigh skin thickness. Ultrasound were performed using a 50-MHz (DermaScan, Cortex Technology) which produces images representing the cross-section of the skin. Skin is shown as a heterogeneous echogenic band at the center of the images. Image description, layers left-to-right: Bright thin layer is the ultrasound liner (thin hyper-echoic layer), a water-based coupling transmission gel (markedly hypoechoic layer), the skin epidermis/dermis (heterogeneous echogenic band) and subcutaneous fat (markedly hypoechoic layer). Imaging was used to measure skin thickness in-vivo using manufacturer's analysis software. Baseline skin thickness measurements were obtained prior to treatment. Post-treatment skin thickness measurements were obtained at 12 weeks after the final treatment.

Figure 4:
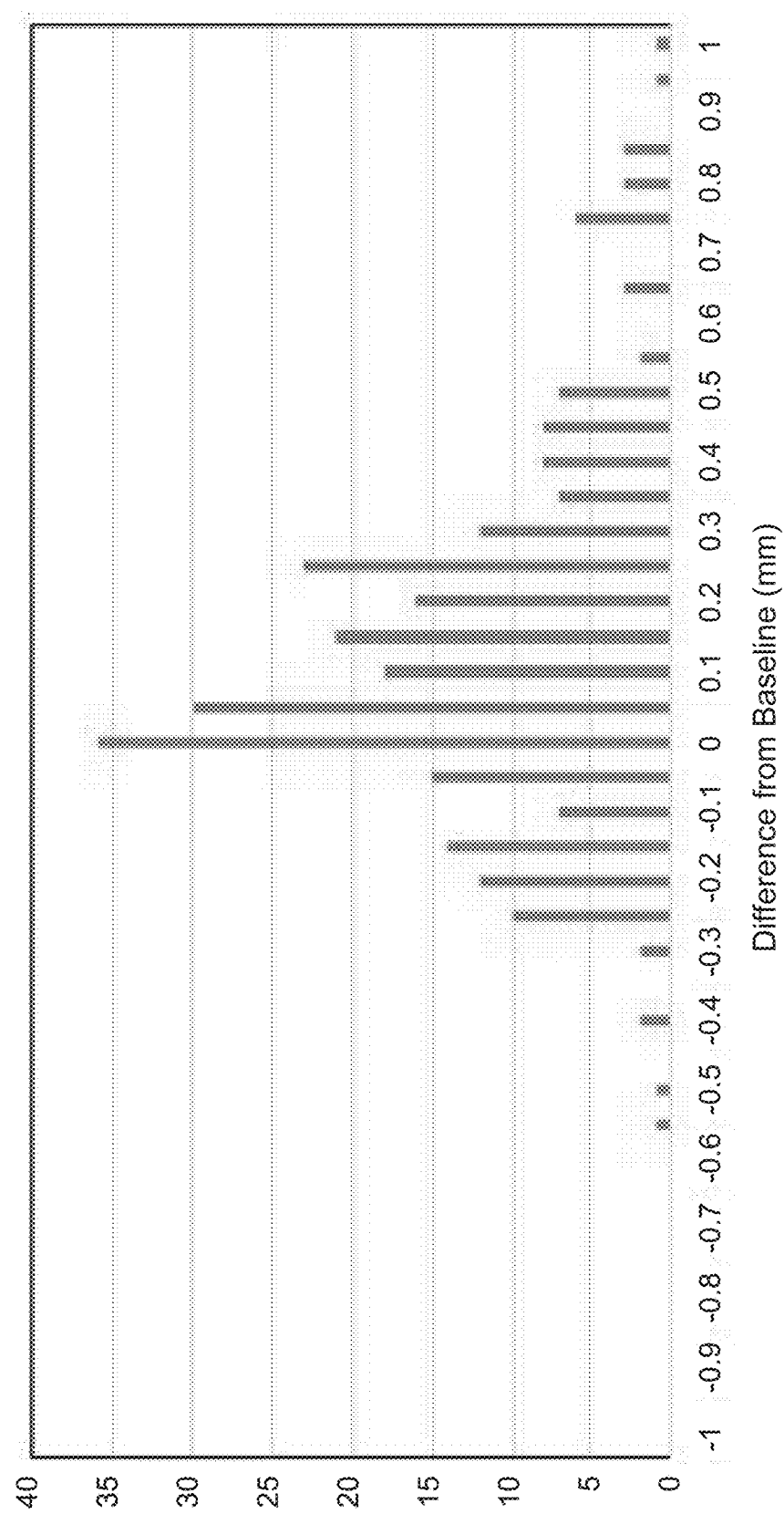
FIG. 4: Histogram of thigh skin thickness change in response to controlled epidermal cooling. Skin thickness measurements were obtained using 50 MHz ultrasound at 270 target sites across 20 human subjects by using the manufacturer's companion analysis software. Histogram shows the distribution of differences between baseline thickness and thickness 12 weeks after the final treatment across all 270 target sites.
Figure 5A:
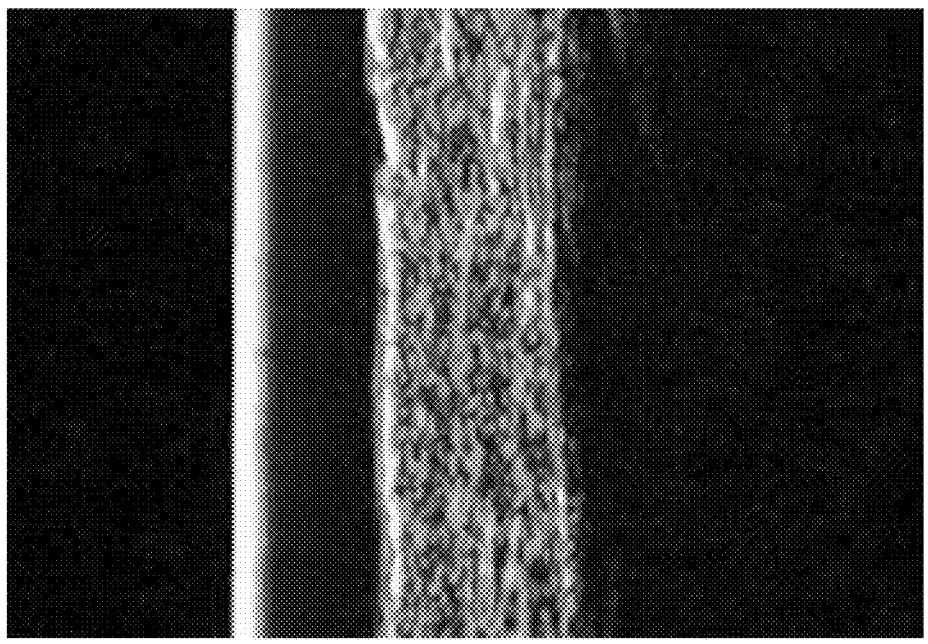
FIGS. 5A-5H: Representative images of the effect of controlled epidermal cooling on skin thickness in two subjects at two different sites. Skin is shown as a heterogeneous echogenic band at the center of the images, top bright layer is the ultrasound liner (thin hyperechoic band), and, coupling gel lies between skin and liner (markedly hypoechoic band). 5A: Subject 1, site 1, baseline (1.42 mm). 5B: Subject 1, site 1, 12 weeks after final treatment (2.05 mm). 5C: Subject 1, site 2, baseline (1.28 mm). 5D: Subject 1, site 2, 12 weeks after final treatment (1.77 mm). 5E: Subject 2, site 1, baseline (0.96 mm). 5F: Subject 2, site 1, 12 weeks after final treatment (1.19 mm). 5G: Subject 2, site 2, baseline (1.05 mm). 5H: Subject 2, site 2, 12 weeks after final treatment (1.23 mm).
Figure 5B:
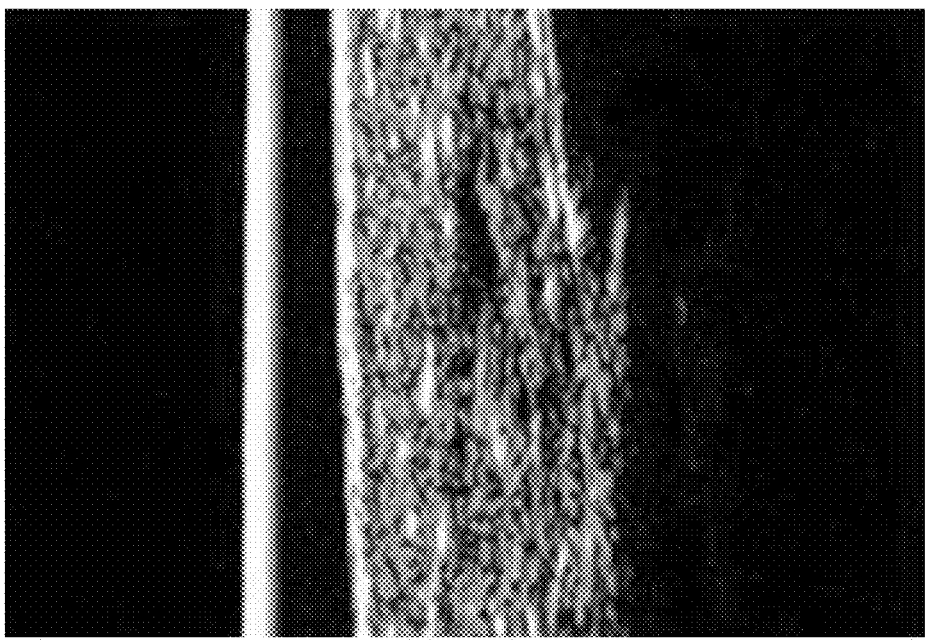
Figure 5C:
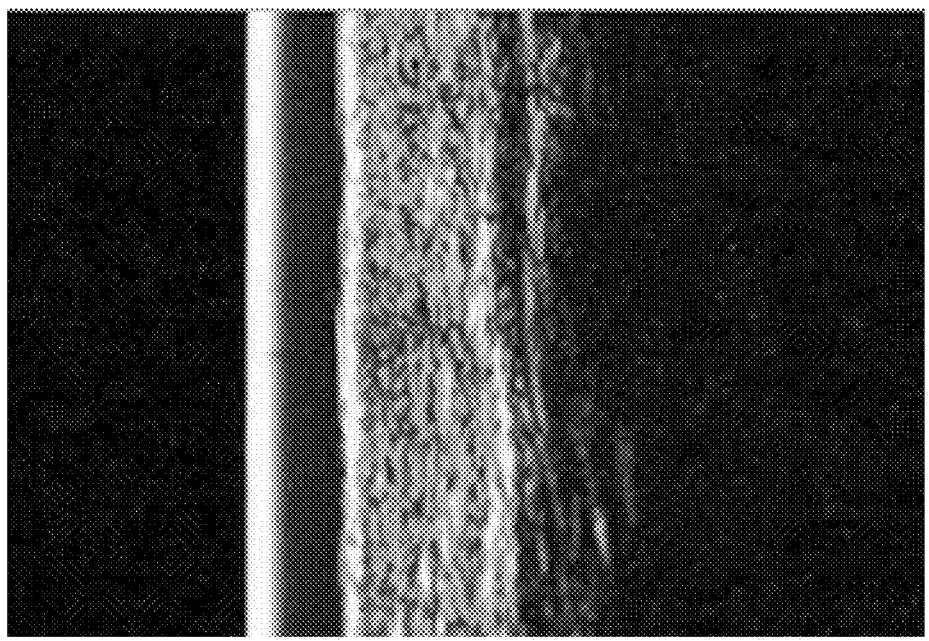
Figure 5D:
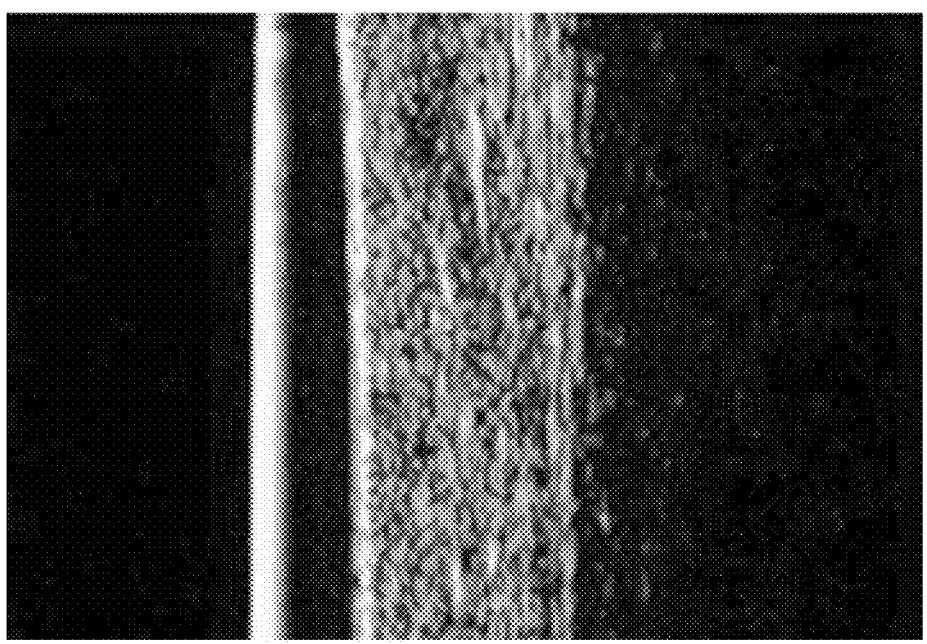
Figure 5E:
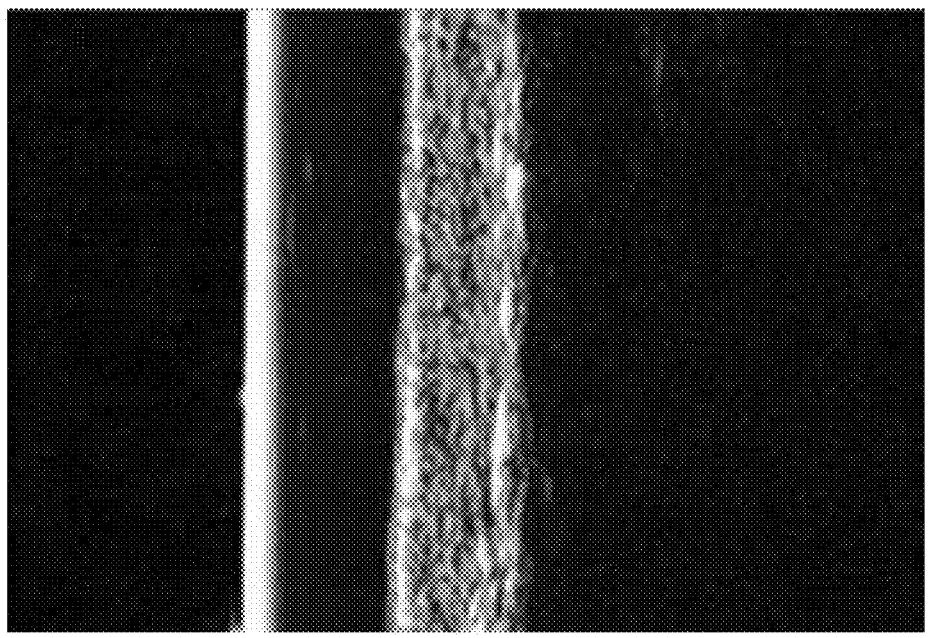
Figure 5F:
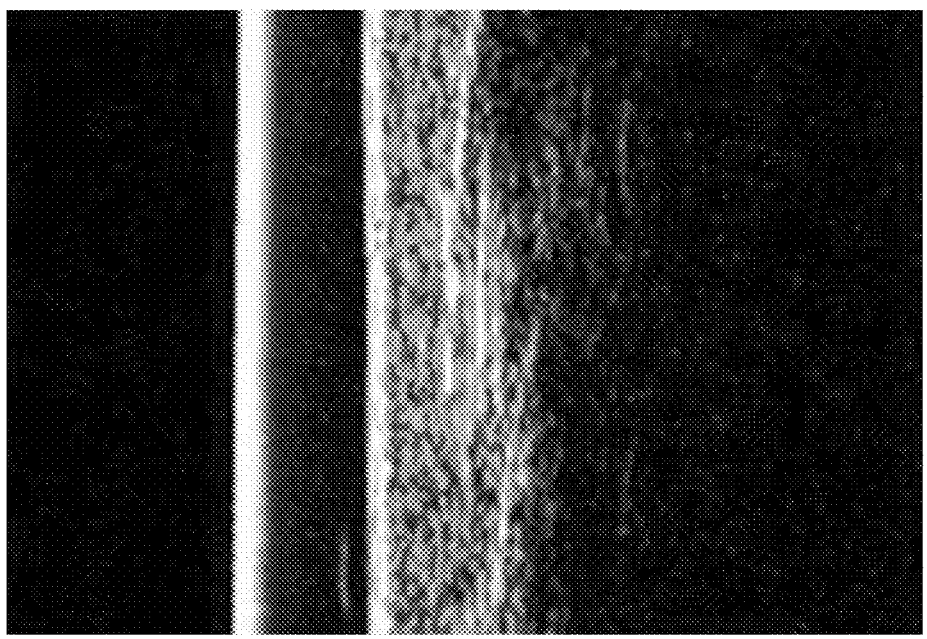
Figure 5G:
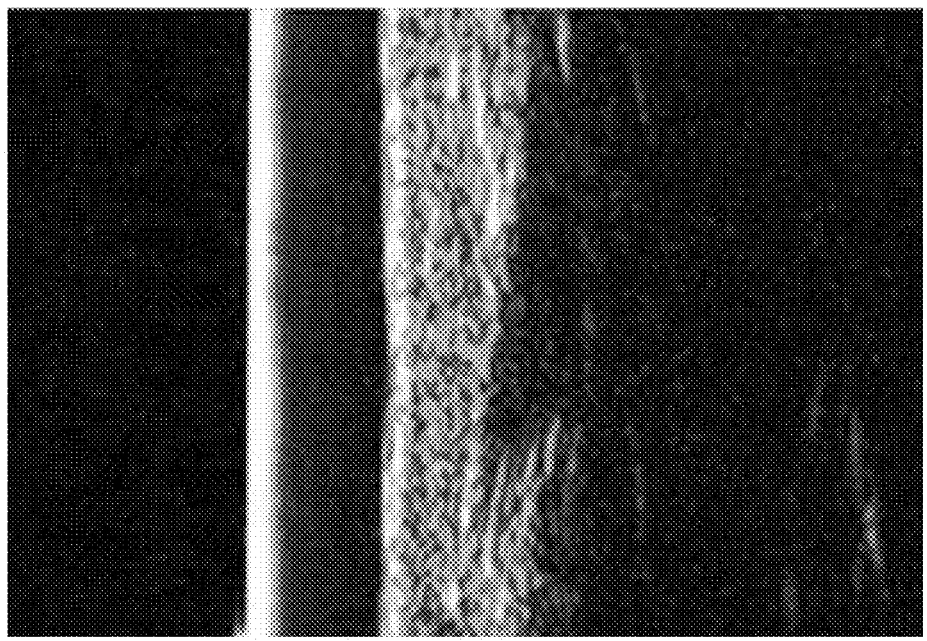
Figure 5H:

A total of 270 target sites were evaluated across the 20 subjects. Subjects exhibited a mean baseline thickness measurement of 1.45±0.29 mm. At 12 weeks post-treatment, the mean thickness measurement was 1.57±0.31 mm, with an overall mean increase from baseline of 0.11±0.27 mm. A histogram showing the distribution of skin thickness changes across all target sites is set forth in FIG. 4. Examples of the specific changes observed in two different subjects are illustrated in FIG. 5. Subject 1 exhibited a change from 1.42 mm at baseline to 2.05 mm 12 weeks post-treatment at a first site (compare FIGS. 5A vs. 5B), and a change from 1.28 mm to 1.77 mm at a second site (compare FIGS. 5C vs. 5D). Subject 2 exhibited a change from 0.96 mm at baseline to 1.19 mm 12 weeks post-treatment at a first site (compare FIGS. 5E vs. 5F), and a change from 1.05 mm to 1.23 mm at a second site (compare FIGS. 5G vs. 5H).

Example 4: Effect of Treatment Duration of Controlled Sub-Cryolipolytic Cooling on Signaling Depth in Target Site A CoolAdvantage Petite treatment unit set to −11° C. was applied proximal to a target site on human subjects' skin for treatment durations of 20, 35 and 60 minutes.

The effect of epidermal cooling on TGF-β mRNA expression in skin and fat layers was evaluated by RNA in situ hybridization (RNA-ISH) staining of formalin-fixed paraffin-embedded (FFPE) tissue samples using the Invitrogen viewRNA™ ISH assay protocol. The probe was human TGF-β1 gene (Thermofisher, # VA6-17264).

Figure 6A:
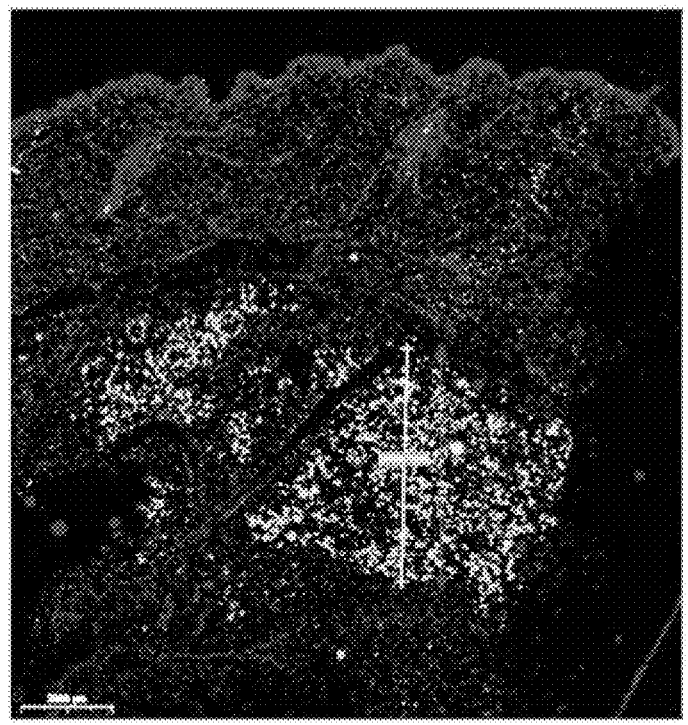
FIGS. 6A-6C: Representative tissue sections showing the effect of different treatment durations of controlled epidermal cooling in the signaling depth of TGF-β mRNA in skin and adipose tissue visualized by in situ hybridization. Fluorescence pseudocolor: TGF-β mRNA=Cy5, yellow. Nucleus=TRITC, blue. 6A: A site of a subject following treatment at −11° C. for 20 minutes with signaling depth into the fat about 5 millimeters (mm) of TGF-β mRNA. 6B: A site of a subject following treatment at −11° C. for 35 minutes with signaling depth into the fat about 9 millimeters (mm) of TGF-β mRNA. 6C: A site of a subject following treatment at −11° C. for 60 minutes with signaling depth into the fat about 14.5 millimeters (mm) of TGF-β mRNA.
Figure 6B:
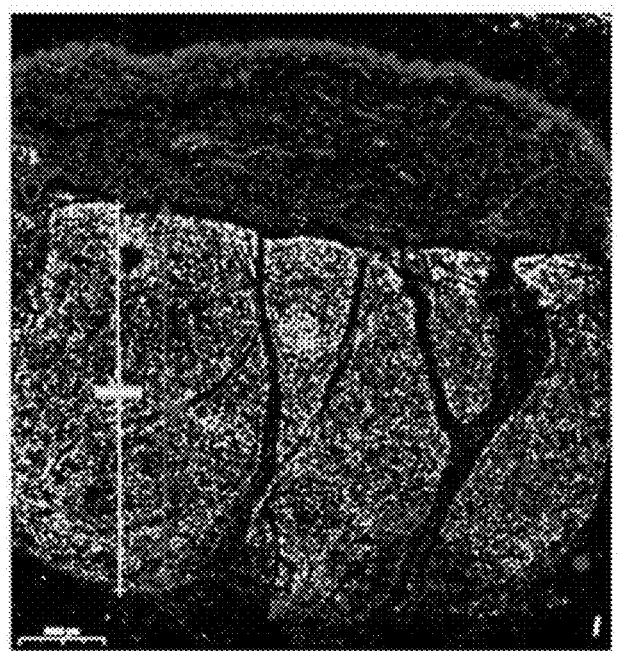
Figure 6C:
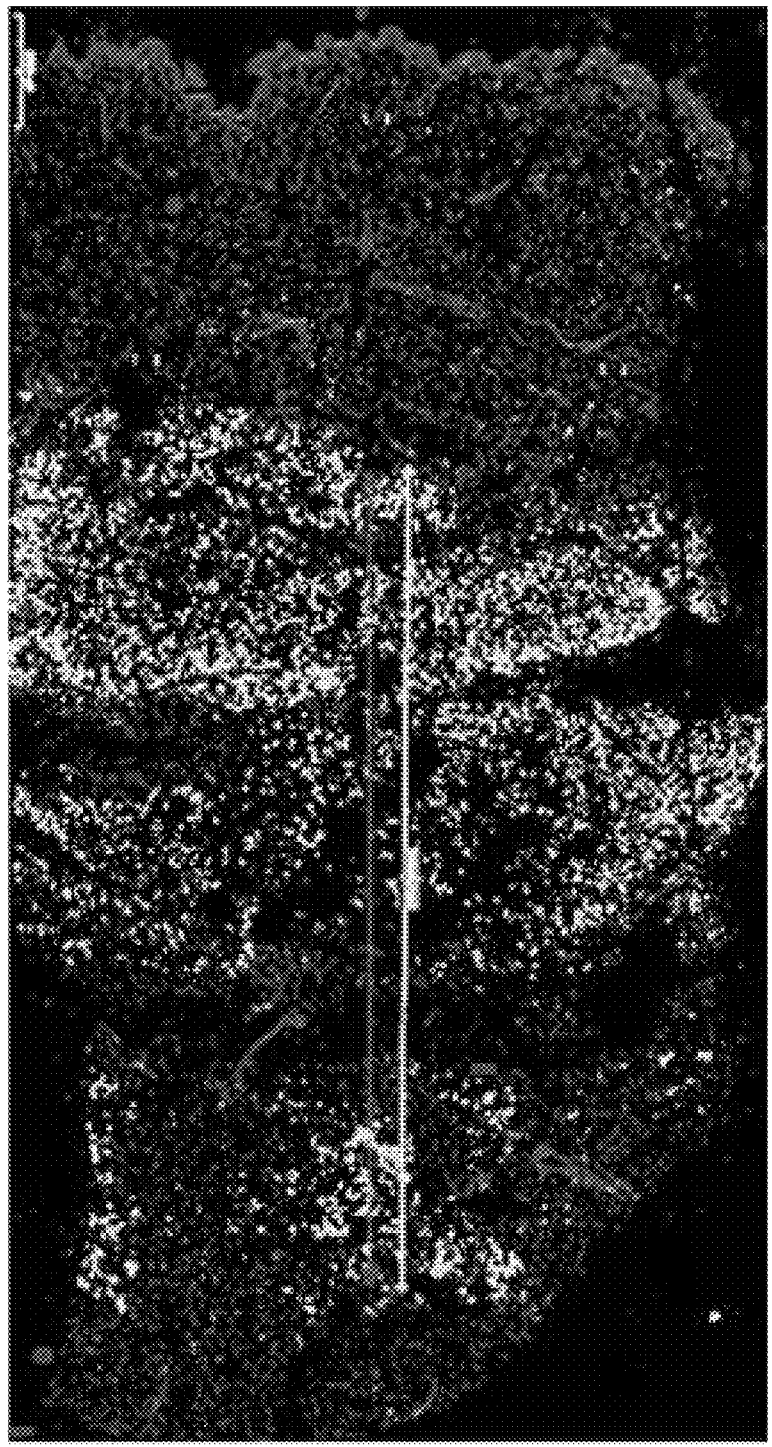

As shown in FIGS. 6A-6C, increasing the duration of treatment increases the depth of TGF-β mRNA expression into the subject's subcutaneous fat layer from about 5 mm (20-minute treatment in FIG. 6A), to about 9 mm (35-minute treatment in FIG. 6B), to about 14.5 mm (60-minute treatment in FIG. 6C).

Figure 7:
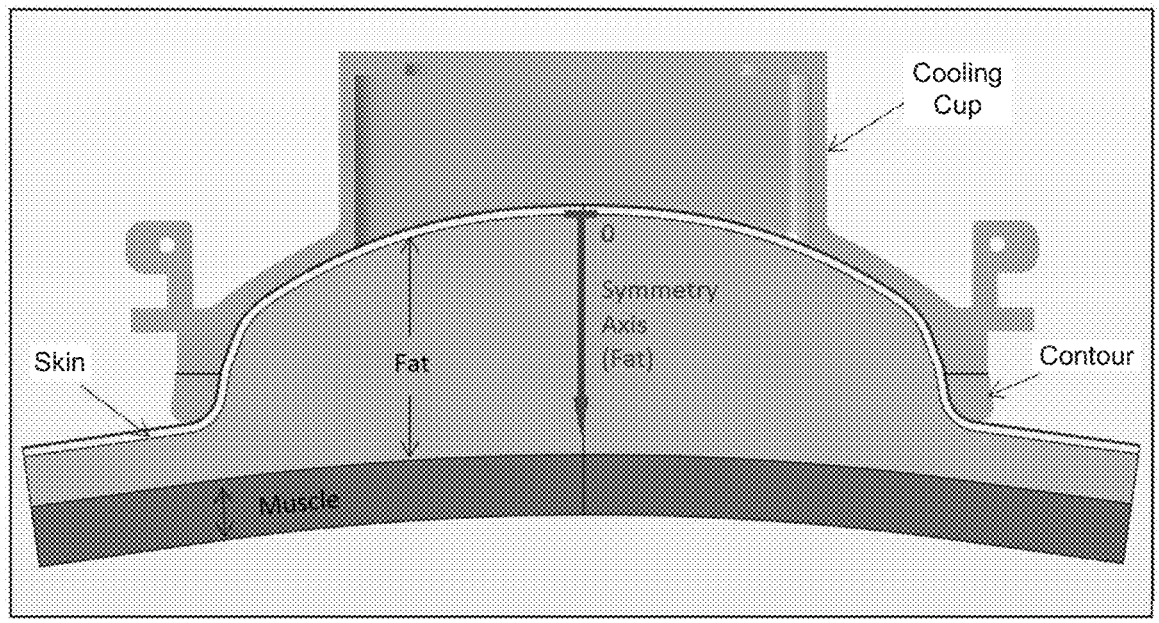
FIG. 7: Cross-sectional illustration of a computational bioheat transfer model for controlled cooling on a target treatment region showing the cooling cup, skin, adipose and muscle tissue layers.

Example 5: Effect of Controlled Sub-Cryolipolytic Cooling on Temperature Distribution and Signaling Depth in Target Site: Theoretical and Experimental A computational three-dimensional model of the CoolAdvantage Petite was created as shown in FIG. 7, all relevant physical boundary and initial conditions, as well as geometrical solid and tissue characteristics of the in vivo tests were included. Transient bioheat transfer modeling was performed using commercially available finite element analysis software (COMSOL Multiphysics v5.0 from COMSOL Inc., Burlington, MA). The bioheat transfer module was used to determine temperature distribution and depth relations as functions of cooling temperatures and treatment durations. Thermal properties and representative dimensions are shown in Table 1.

TABLE 1

Summary of Tissue Thermal Properties and Thicknesses

| Layer | Thickness [mm] | Density [kg/m^3] | Thermal conductivity [W/m K] | Specific Heat [J/kg K] |
|---|---|---|---|---|
| Skin | 2 | 1200 | 0.355 | 3350 |
| Fat | variable | 920 | 0.216 | 2280 |
| Muscle | 5 | 1270 | 0.5 | 3800 |
| Cup (Al) | variable | 2700 | 167 | 896 |

The data in Table 1 was adapted from Cohen, M L. Measurement of the thermal properties of human skin. A review. J. Invest. Dermatol., 69, pp. 333-338, 1977; Duck, F. A., Physical Properties of Tissues: A comprehensive Reference Book, Academic Press, 1990; and Jimenez Lozano, J. N., Vacas-Jacques, P., Anderson, R. R., Franco, W. Effect of fibrous septa in radiofrequency heating of cutaneous and subcutaneous tissues: Computational study, Lasers in Surgery and Medicine, 45 (5), pp. 326-338, 2013.

Figure 8:
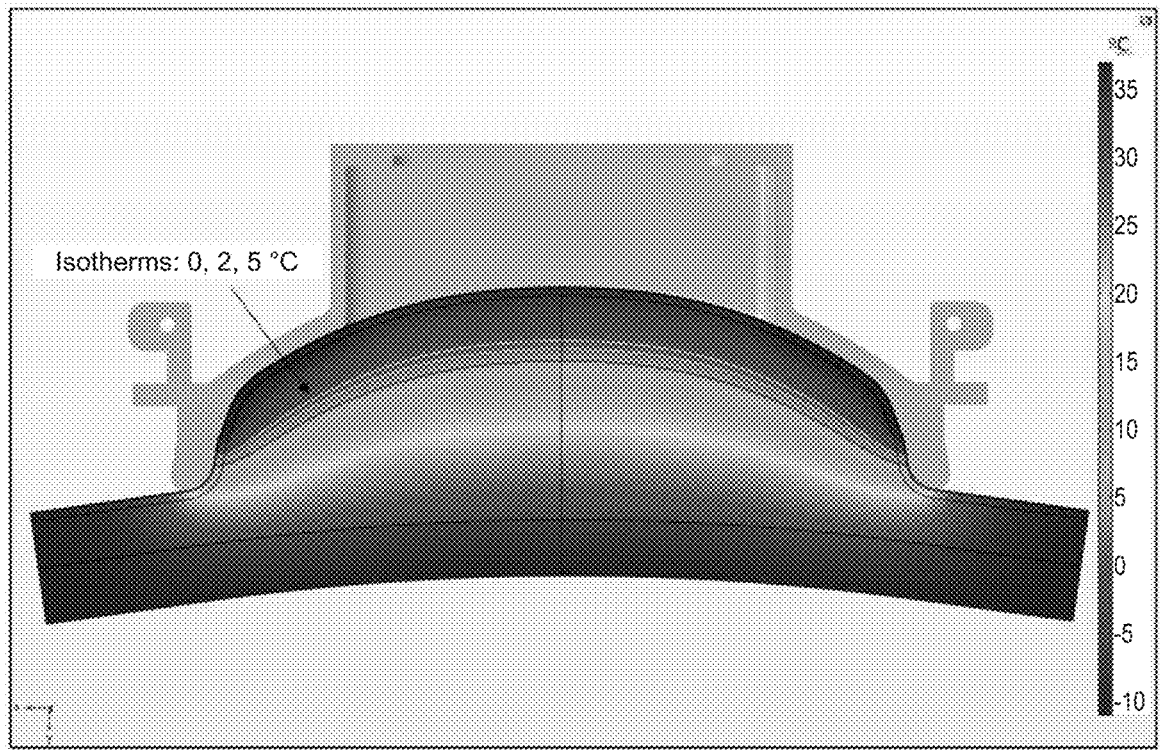
FIG. 8: Cross-sectional view of the temperature distribution within tissue for a controlled cooling treatment at −11° C. for 35 minutes (bioheat transfer model depicted in FIG. 7). Colorbar indicates the temperature range in degrees Celsius. Isotherms for 0, 2, and 5 degrees Celsius are included for reference of the cooled tissue extent. The transient bioheat transfer three-dimensional model was solved using commercially available finite element analysis software (COMSOL Multiphysics v 5.0, COMSOL Inc., Burlington, MA).
Figure 9A:
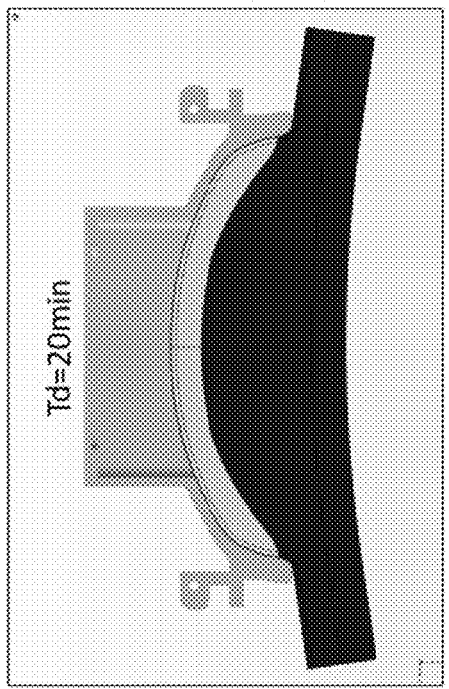
FIGS. 9A-9D: Cross-sectional view of a two-color (yellow-blue) map within tissue for a controlled cooling treatment at −11° C. Colormap is divided at a threshold temperature (Ts) of 5° C. such as yellow color represents tissue at a temperature, T≤5° C., and dark-blue represents tissue with T>5° C. Simulations for different treatments durations (Td) are presented in 9A: Td of 10 minutes. 9B: Td of 20 minutes. 9C: Td of 35 minutes. 9D: Td of 60 minutes.
Figure 9B:
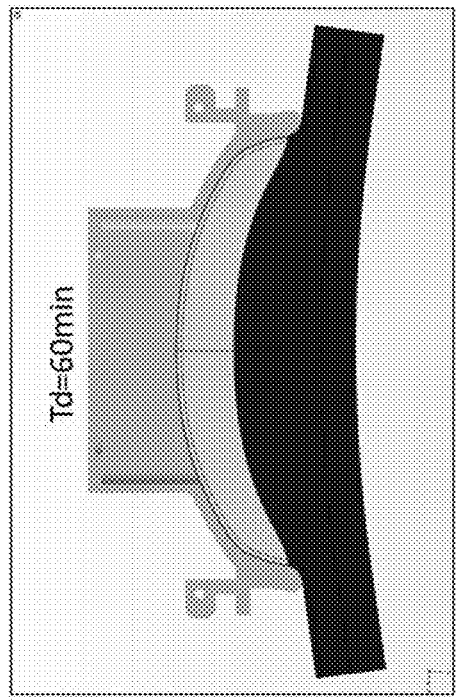
Figure 9C:
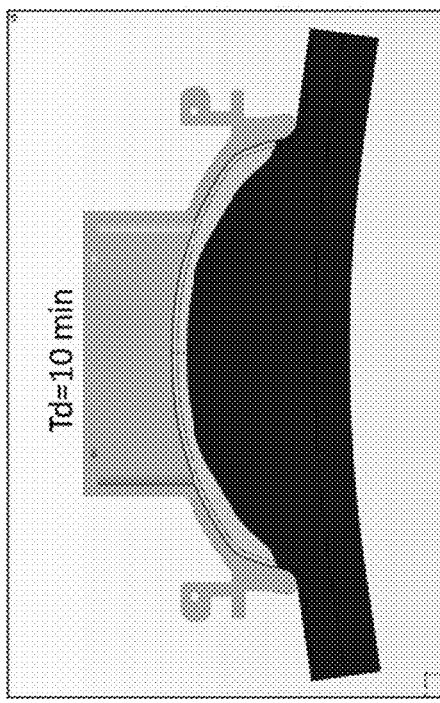
Figure 9D:
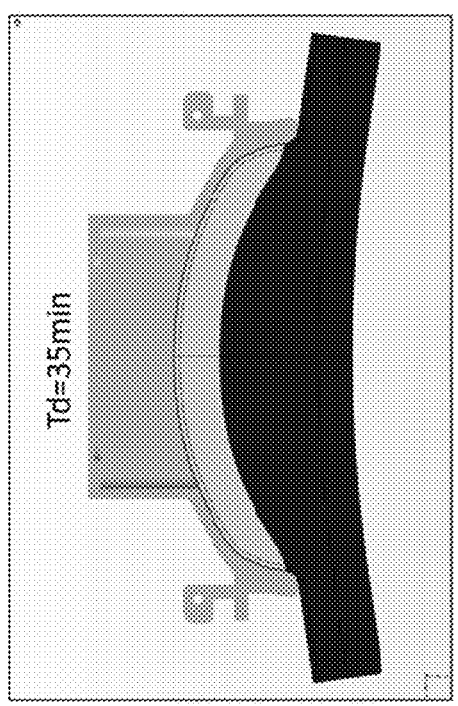

A cross-sectional view of the temperature distribution within tissue in a treatment site during application at −11° C. for 35 minutes is shown in FIG. 8. Isotherms at 0, 2 and 5° C. highlight the extent of the cooled tissue at temperatures at or below those specific temperatures. For reference, we can define a threshold temperature (Ts) as the limit temperature at which signaling events are triggered (e.g. increased expression of TGF-β and/or COL1A1 mRNA). By doing so, we can map the tissue domains that enclose signaling and non-signaling tissue. Temperature thresholds may change between different cell types, molecular content, and other biological characteristics. The effect of treatment duration (Td) in the volume extent of signaling within tissue at a threshold temperature of 5° C. is shown in FIGS. 9A-9D. As shown in FIGS. 9A-9D, the volume of tissue at Ts≤5° C. (tissue undergoing signaling) increases with the treatment duration, such as from 10 minutes (FIG. 9A), to 20 minutes (FIG. 9B), to 35 minutes (FIG. 9C), to 60 minutes (FIG. 9D) at a fixed cooling temperature (Tapp).

Figure 10A:
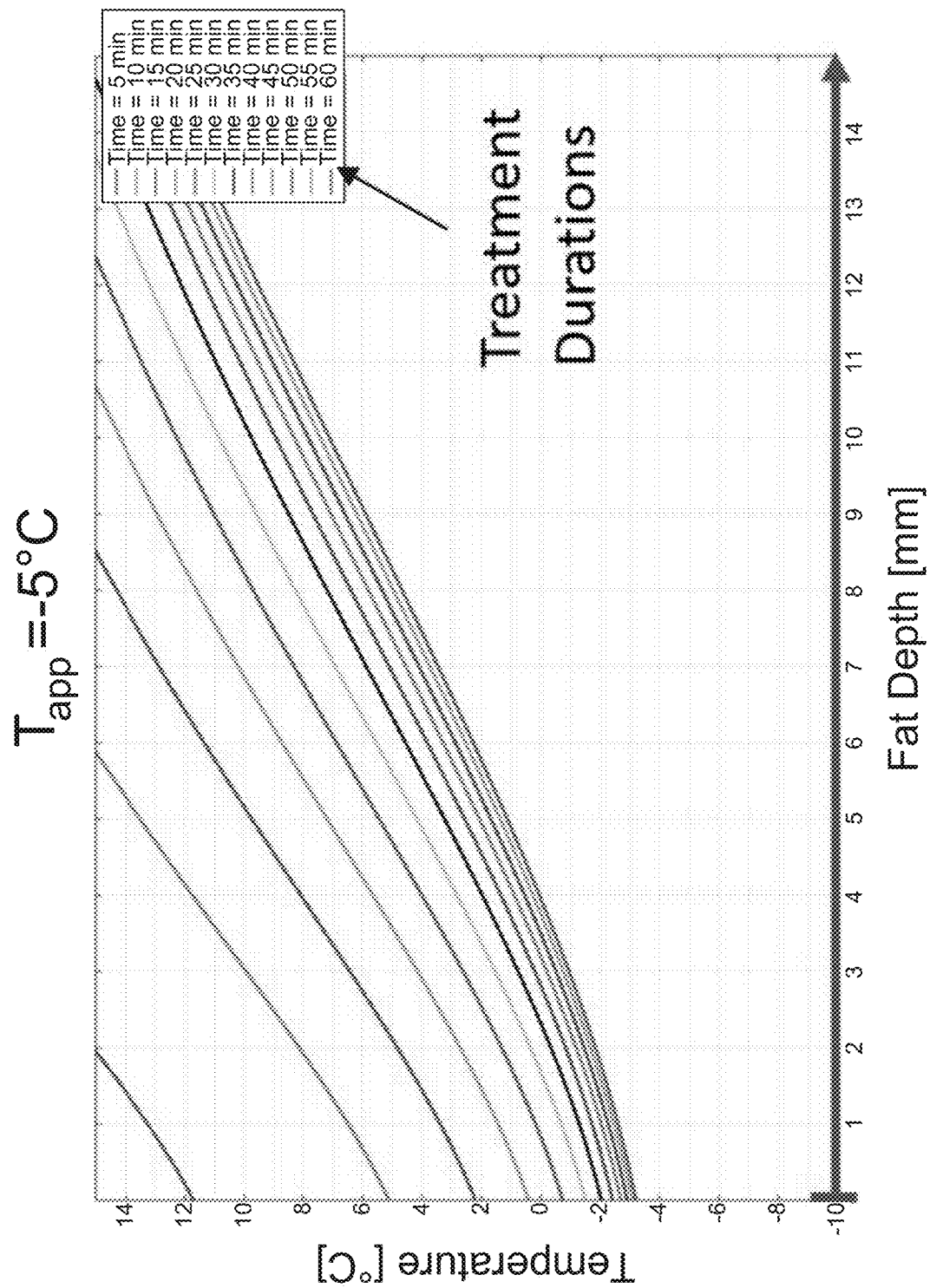
FIGS. 10A-10C: Temperature profiles along symmetry axis of the model within fat (See, FIG. 7) for different treatment durations (Td) and different applied controlled cooling temperatures (Tapp). 10A: Tapp of −5° C. 10B: Tapp of −11° C. 10C: Tapp of −15° C.
Figure 10B:
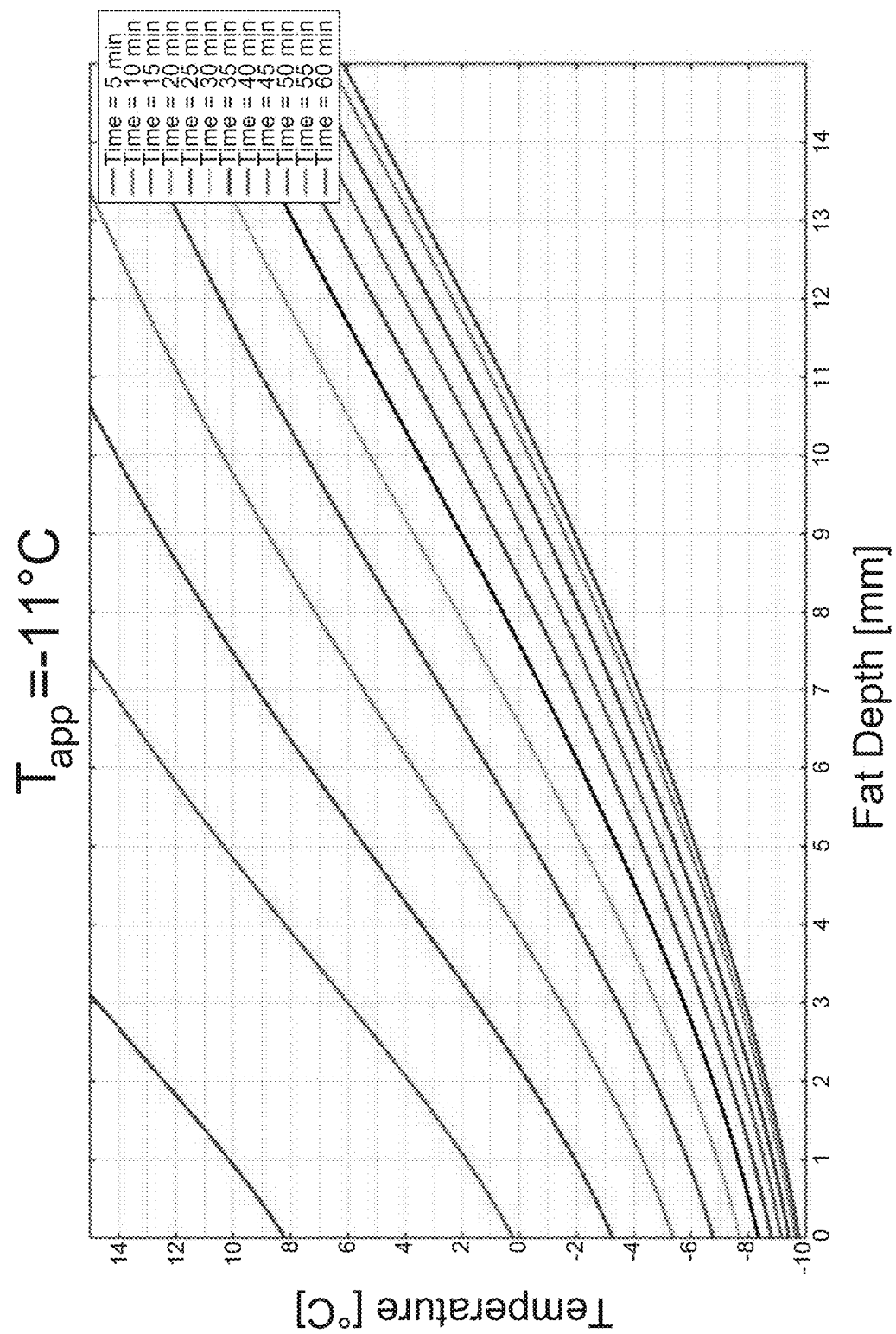
Figure 10C:
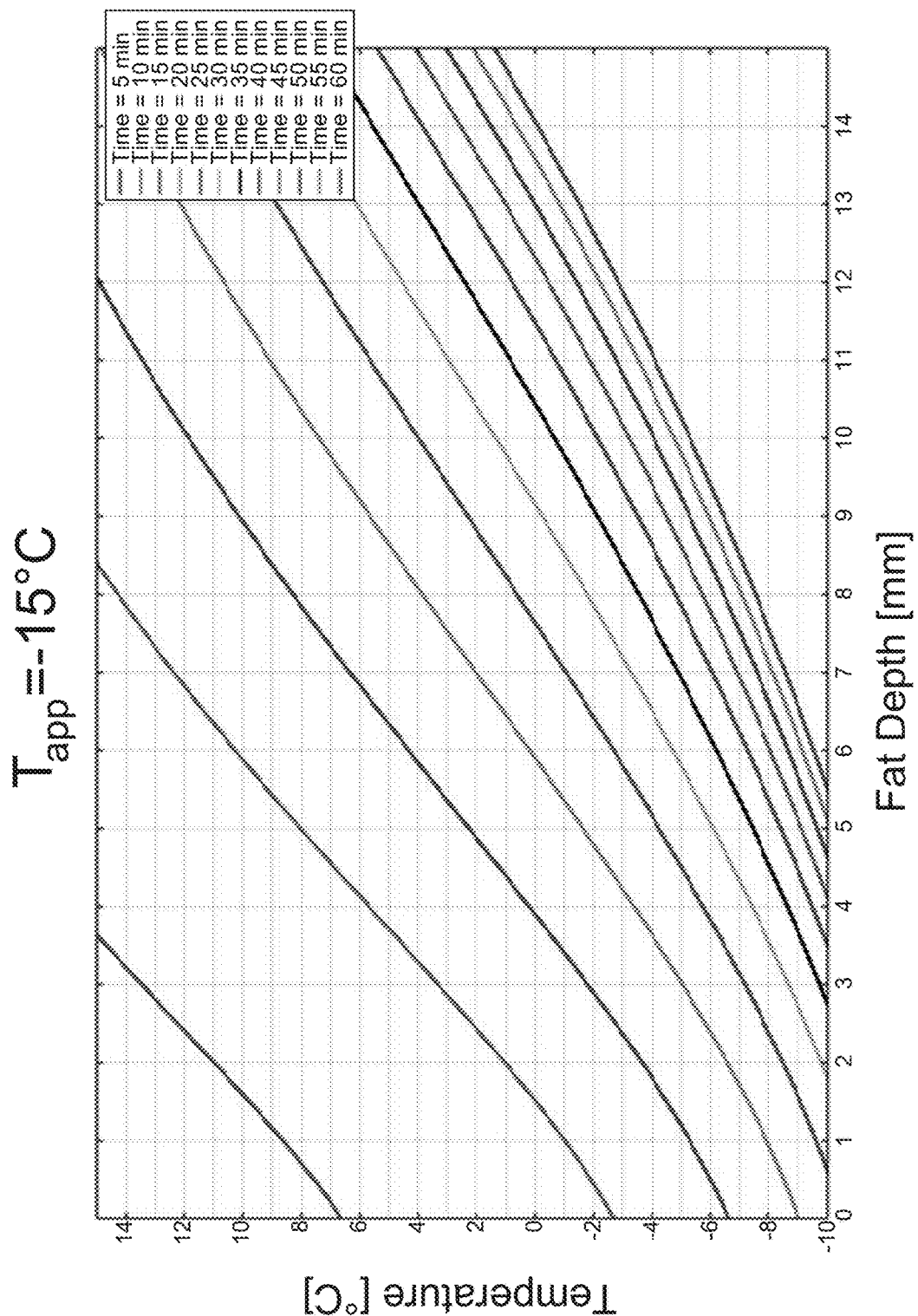

Similarly, changing Tapp can be used to vary the extent of signaling within tissue (compare FIGS. 10A-10C). These curves were calculated to quantify the maximum signaling depth into the fat (temperature profile at the symmetry line, see FIG. 7) and to inspect the variation of the signaling depth for changes in Td, Tapp and Ts. Temperature profiles for varying cooling temperatures are shown in FIG. 10A (Tapp=−5° C.), FIG. 10B (Tapp=−11° C.) and FIG. 10C (Tapp=−11° C.) where color curves represent specific treatment durations (Td).

Figure 11:
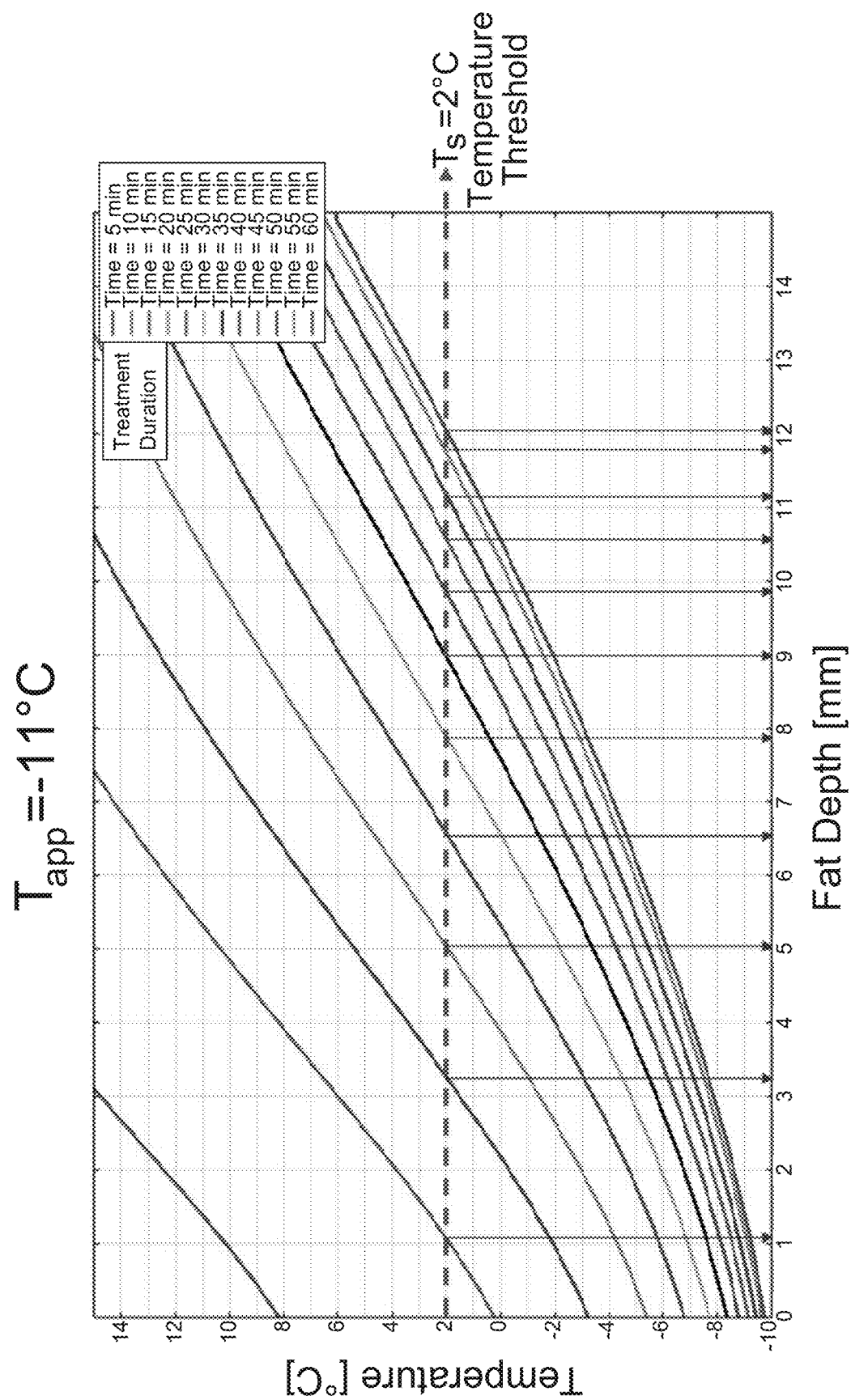
FIG. 11: Temperature profile along symmetry axis within fat for different treatment durations and a controlled cooling temperature, Tapp of −11° C. Curves were analyzed at a temperature threshold (Ts) of 2° C. (dashed line). Signaling depth was assessed for different time durations (Td), arrows.
Figure 12:
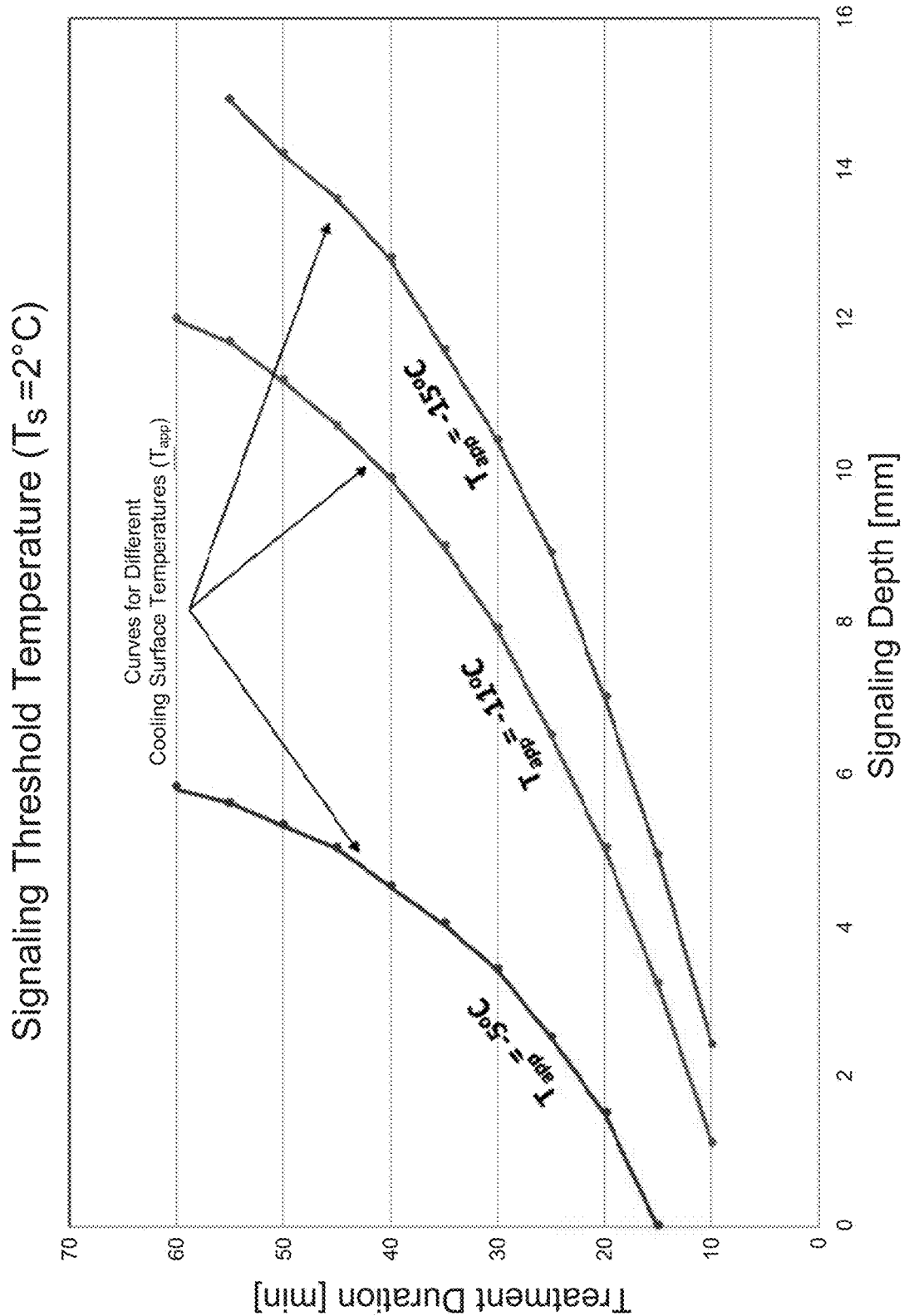
FIG. 12: Signaling depth curves at a threshold temperature of Ts of 2° C. for different controlled cooling temperatures: Tapp of −5° C., −11° C. (exemplary calculation shown in FIG. 11), and −15° C.
Figure 13:
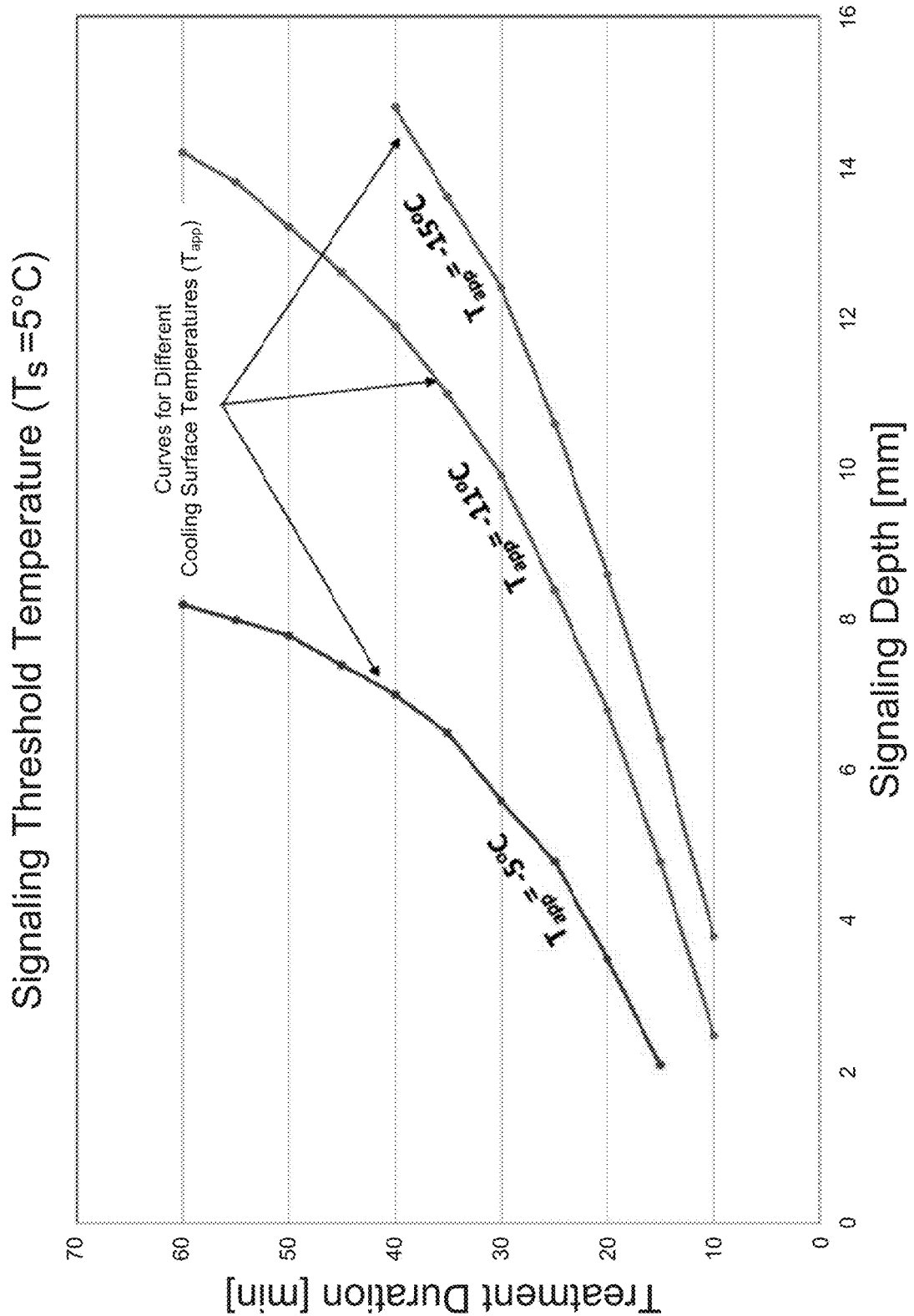
FIG. 13: Signaling depth curves at a threshold temperature of Ts of 5° C. for different controlled cooling temperatures: Tapp of −5° C., −11° C., and −15° C.).

For fixed conditions, for example, a cooling temperature (Tapp=−11° C.) and a specific threshold temperature (Ts=2° C.), the signaling depth can be evaluated for any treatment duration (Td) as shown in FIG. 11. Treatment durations of FIG. 11 were set from 5 to 60 minutes and signaling fat depths were assessed (arrows) for each curve. Similar curves can be created to inspect the effect of Tapp in signaling depth for specific treatment durations (Td) at specific threshold values Ts=2° C. (FIG. 12) and Ts=5° C. (FIG. 13).

Figure 14:
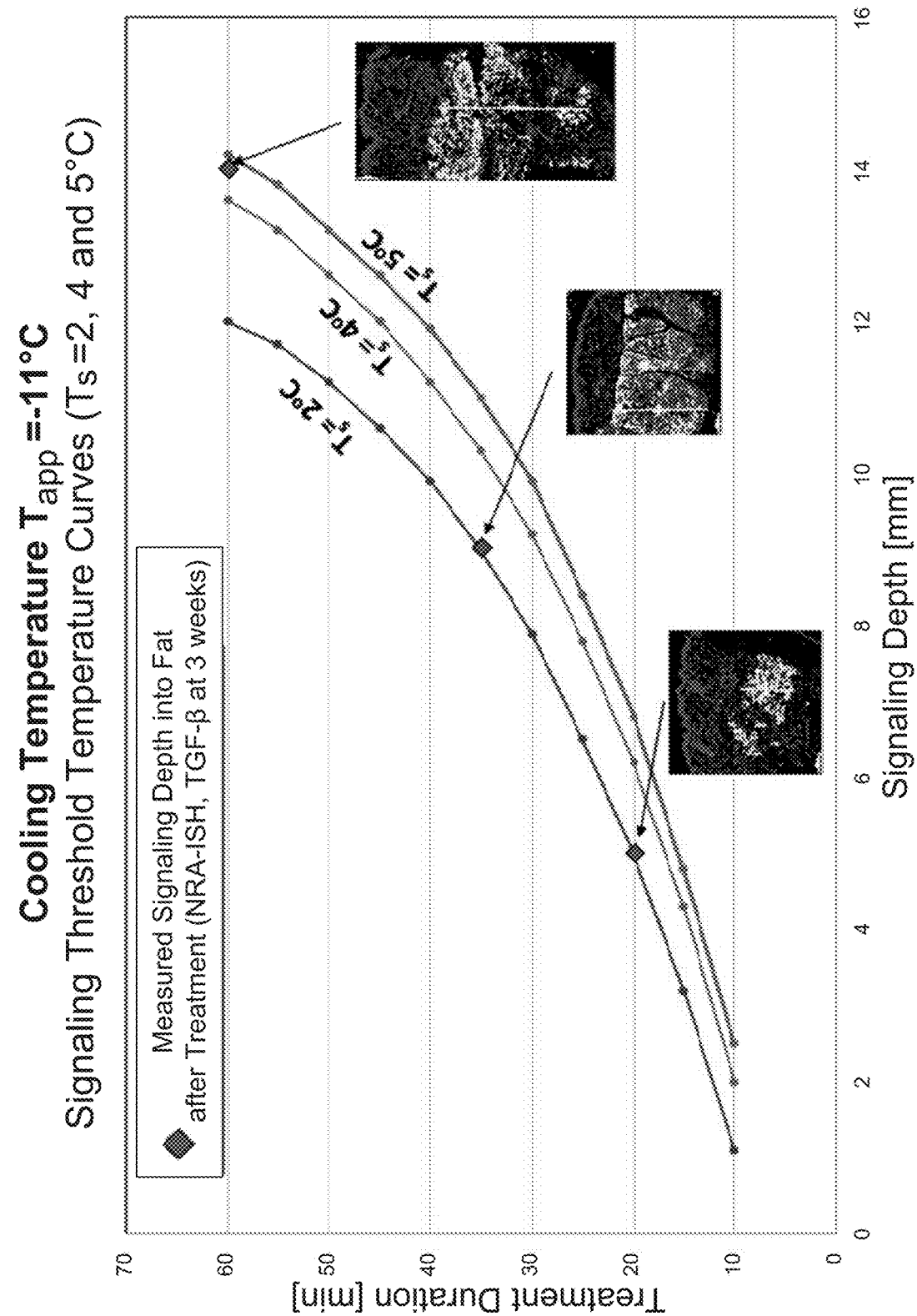
FIG. 14: Comparison of observed signaling depth (as measured in tissue sections from in vivo tests, see FIG. 6A-6C) and theoretical signaling depth curves (from bioheat transfer model) at a Tapp of −11° C. and Ts of 2° C., 4° C., and 5° C.

Comparison of signaling depth between theoretical values and in vivo tests are shown in FIG. 14 for a fixed cooling temperature (CoolAdvantage Petite, Tapp=−11° C.) and different treatment durations. Curves for threshold temperatures of 2, 4 and 5° C. were compared with the in vivo tests results presented in FIG. 6A-6C and showed a close correlation with increased expression of TGF-β1 mRNA. These outcomes represent supporting evidence that the signaling response can be controlled with the specific sub-cryolipolytic cooling conditions and methods presented herein.

As explained above, sub-cryolipolytic cooling can induce one or more signaling events in a subject; however, the parameters associated with sub-cryolipolytic cooling treatment protocols do not cause significant damage to the subject's subcutaneous layer (e.g., a volume of the subject's fat is not aesthetically decreased by at least about 20% as is observed with cryolipolytic cooling). While one or more signaling events are induced at about 2° C., about 3° C., or about 5° C., and aesthetic reduction in the subject's subcutaneous fat occurs at about 2° C., about 5° C., and about 10° C.; to achieve the aesthetic fat reduction, the subject's subcutaneous fat layer is treated (e.g., cooled to either 2° C., 5° C., or 10° C.) to at least about 10 mm below the surface of the subject's skin. In contrast, sub-cryolipolytic cooling is achieved by using temperatures and/or treatment times that do not significantly damage the fat in the subcutaneous layer more than about 7, 8, or 9 mm below the upper skin surface (e.g., deep subcutaneous layer fat is minimally affected).

Durations of treatment, applicator temperature, signaling threshold temperature, and thickness of the treatment area can be selected using the graphs, charts, and other illustrations as represented in FIGS. 10-14 to achieve sub-cryolipolytic cooling (e.g., induce one or more signaling events without significant destruction of subcutaneous fat). For example, if the applicator temperature is about −11° C. and the signaling temperature is about 2° C., the duration of treatment needed to achieve this signaling temperature at a desired depth into the subject's sub-cutaneous layer between 1 mm and 12 mm can be determined from FIG. 11. As another example, using FIGS. 14-18 and the principles therein, one can select an applicator temperature of about −5° C. to about −15° C. to achieve a signaling temperature of about 2, 4, or 5° C. Also, a desired depth into the subject's sub-cutaneous layer a signaling temperature is achieved and a duration of treatment of treatment necessary to achieve this signaling depth can be determined.

In addition, a thickness of the subject's subcutaneous layer (e.g., fat layer) to be damaged can be related to a thickness of the subject's skin layer (e.g., subject's having thicker skin layers may need to have a thicker layer of fat be damaged to result in adequate signaling so that the skin can be adequately affected). As such, the parameters selected for sub-cryolipolytic cooling could also consider the subject's skin layer thickness, such that signaling depths in the subject's subcutaneous layer can be chosen to be a factor of about 0.5 times, about 1 time, about 2 times, or about 3 times thicker than the subject's skin layer. The factor can depend on a duration of time that the one or more signaling events occur in the subject's sub-cutaneous layer. For example, an applicator temperature of about −25° C. can cool deeper into the subject's subcutaneous layer more rapidly than an applicator temperature of about −15° C., however, the duration of treatment could be longer at about −25° C. compared to about −15° C. if the one or more desired signaling events are not sufficiently otherwise induced.

ADDITIONAL EMBODIMENTS

Various embodiments of the technology are described above. It will be appreciated that details set forth above are provided to describe the embodiments in a manner sufficient to enable a person skilled in the relevant art to make and use the disclosed embodiments. Several of the details and advantages, however, may not be necessary to practice some embodiments. Additionally, some well-known structures or functions may not be shown or described in detail, so as to avoid unnecessarily obscuring the relevant description of the various embodiments. Although some embodiments may be within the scope of the technology, they may not be described in detail with respect to the Figures. Furthermore, features, structures, or characteristics of various embodiments may be combined in any suitable manner. Moreover, one skilled in the art will recognize that there are a number of other technologies that could be used to perform functions similar to those described above. While processes or blocks are presented in a given order, alternative embodiments may perform routines having stages, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel, or may be performed at different times. The headings provided herein are for convenience only and do not interpret the scope or meaning of the described technology.

The terminology used in the description is intended to be interpreted in its broadest reasonable manner, even though it is being used in conjunction with a detailed description of identified embodiments.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. Use of the word "or" in reference to a list of two or more items covers all of the following interpretations of the word: any of the items in the list, all of the items in the list, and any combination of the items in the list. Furthermore, the phrase "at least one of A, B, and C, etc." is intended in the sense that one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense that one having skill in the art would understand the convention (e.g., "a system having at least one of A, B, or C" would include but not be limited to systems that have A alone, B alone, C alone, A and B together, A and C together, B and C together, and/or A, B, and C together, etc.).

Some of the functional units described herein have been labeled as modules, in order to more particularly emphasize their implementation independence. For example, modules (e.g., modules discussed in connection with FIG. 20) may be implemented in software for execution by various types of processors. An identified module of executable code may, for instance, comprise one or more physical or logical blocks of computer instructions which may, for instance, be organized as an object, procedure, or function. The identified blocks of computer instructions need not be physically located together, but may comprise disparate instructions stored in different locations which, when joined logically together, comprise the module and achieve the stated purpose for the module.

A module may also be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

A module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

Any patents, applications and other references cited herein are incorporated herein by reference. Aspects of the described technology can be modified, if necessary, to employ the systems, functions, and concepts of the various references described above to provide yet further embodiments.

These and other changes can be made in light of the above Detailed Description. While the above description details certain embodiments and describes the best mode contemplated, no matter how detailed, various changes can be made. Implementation details may vary considerably, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated.

The foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

What is claimed is:

1. A method of decreasing skin laxity in a subject comprising:

cooling the subject's skin at a target site with a treatment unit to lower the temperature of the epidermis at the target site to about −15° Celsius (C) to about 5° C.; and discontinuing cooling before a subcutaneous fat layer 7 mm below the target site decreases below a temperature of about 3° C. such that adipocyte signaling is altered but less than 10% of subcutaneous lipid-rich cells are destroyed, wherein said alteration of adipocyte signaling decreases skin laxity of the subject's skin.

2. The method of claim 1, wherein less than 1%, 2%, 3%, 4%, 5%, or 7% of the subcutaneous lipid-rich cells are destroyed.

3. The method of claim 1, wherein said cooling does not produce any adverse skin effects.

4. The method of claim 3, wherein said adverse effects are selected from the group consisting of hyper-pigmentation, hypo-pigmentation, unwanted blistering, unwanted scarring, permanent undesirable alterations, and disfiguring scars.

5. The method of claim 1, wherein said alteration in adipocyte signaling results in an increase in expression of one or more cytokines selected from the group consisting of TGF-β, TNF-α, IL-1β, IL-6, MCP-1, leptin, adiponectin, resistin, acylation-stimulating protein, alpha 1 acid glycoprotein, pentraxin-3, IL-1 receptor antagonist, macrophage migration inhibitor factor, and SAA3.

6. The method of claim 5, wherein said increase in expression occurs in the dermal layer, the subcutaneous layer, or both.

7. The method of claim 1, wherein said alteration in adipocyte signaling results in an increase in one or more extracellular matrix components selected from the group consisting of collagen, elastin, proteoglycans (e.g., heparan sulfate, keratin sulfate, and chondroitin sulfate), fibrinogen, laminin, fibrin, fibronectin, hyaluronan, hyaluronic acid, versican, aggrecan, lumican, decorin, glypican, tenascins, syndecans, integrins, discoidin domain receptors, perlecan, N-CAM, ICAM, VCAM, focal adhesion kinases, matrix metalloproteases, and Rho-kinases.

8. The method of claim 7, wherein said increase in one or more extracellular matrix components occurs in the epidermal layer, dermal layer, the subcutaneous layer, or combinations thereof.

9. The method of claim 1, wherein said cooling is performed by applying a treatment unit proximal to the target site.

10. The method of claim 9, wherein the temperature of said treatment unit is about −18° C. to about 0° C.

11. The method of claim 1, wherein said cooling is discontinued when the temperature of the subcutaneous fat layer 7 mm below the target site decreases below about 3° C.

12. A method of decreasing skin laxity in a subject comprising:

applying a cooling element proximal to a target site on the subject's skin for a period of time sufficient to cool the epidermis at the target site to about −15° C. to about 5° C., wherein said cooling results in an alteration of one or more adipocyte signaling events; and removing the cooling element before the temperature of the subcutaneous fat layer about 7 mm below the target site decreases below a temperature of +3° C.

13. A method of decreasing skin laxity in a subject comprising:

applying a cooling element proximal to a target site on the subject's skin for a period of time sufficient to cool the epidermis at the target site to about −15° C. to about 5° C., wherein said cooling results in an alteration of one or more adipocyte signaling events; and removing the cooling element when the temperature of the epidermis at the target site has been at a temperature of about −15° C. to about 5° C. for about 10 minutes to about 25 minutes such that adipocyte signaling is altered but less than 10% of subcutaneous lipid-rich cells are destroyed.

14. The method of claim 13, wherein said target site is selected from the group consisting of: chin, cheeks, arms, pectoral areas, thighs, calves, buttocks, abdomen, "love handles", back, and breast.

15. The method of claim 14, wherein said target site is the chin.

* * * * *